United States Patent
Hur et al.

(10) Patent No.: US 11,302,871 B2
(45) Date of Patent: Apr. 12, 2022

(54) ORGANIC LIGHT-EMITTING DEVICE AND LIGHT-EMITTING APPARATUS INCLUDING THE SAME

(71) Applicant: Samsung Display Co., Ltd., Yongin-si (KR)

(72) Inventors: Jaeweon Hur, Yongin-si (KR); Soungwook Kim, Yongin-si (KR); Seulong Kim, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 379 days.

(21) Appl. No.: 16/556,715

(22) Filed: Aug. 30, 2019

(65) Prior Publication Data

US 2020/0266354 A1 Aug. 20, 2020

(30) Foreign Application Priority Data

Feb. 14, 2019 (KR) .................. 10-2019-0017400

(51) Int. Cl.
*H01L 51/00* (2006.01)
*C07D 209/88* (2006.01)
(Continued)

(52) U.S. Cl.
CPC ........ *H01L 51/0061* (2013.01); *C07D 209/88* (2013.01); *H01L 27/3248* (2013.01);
(Continued)

(58) Field of Classification Search
None
See application file for complete search history.

(56) References Cited

U.S. PATENT DOCUMENTS 5,855,994 A * 1/1999 Biebuyck ............ H01L 51/5253
428/209
7,375,462 B2 * 5/2008 Suh ..................... H01L 51/5048
313/504

(Continued)

FOREIGN PATENT DOCUMENTS

KR 10-2012-0139610 A 12/2012
KR 10-1565039 B1 11/2015
(Continued)

OTHER PUBLICATIONS

Kondakov, Denis Y. "Role of chemical reactions of arylamine hole transport materials in operational degradation of organic light-emitting diodes." Journal of Applied Physics 104, No. 8 (2008): 084520. (Year: 2008).*

(Continued)

*Primary Examiner* — Robert S Loewe
(74) *Attorney, Agent, or Firm* — Lewis Roca Rothgerber Christie LLP

(57) ABSTRACT

Provided are an organic light-emitting device including a capping layer including an amine-based compound represented by a set or predetermined formula and a radical scavenger, and a light-emitting apparatus including the organic light-emitting device. The organic light-emitting device includes: a first electrode; a second electrode facing the first electrode; an organic layer between the first electrode and the second electrode and including an emission layer a capping layer on the second electrode, wherein the capping layer includes the amine-based compound.

20 Claims, 11 Drawing Sheets

(51) Int. Cl.
*H01L 51/52* (2006.01)
*H01L 51/50* (2006.01)
*H01L 27/32* (2006.01)

(52) U.S. Cl.
CPC ........ *H01L 51/0072* (2013.01); *H01L 51/506* (2013.01); *H01L 51/5012* (2013.01); *H01L 51/5016* (2013.01); *H01L 51/5072* (2013.01); *H01L 51/5088* (2013.01); *H01L 51/5092* (2013.01); *H01L 51/5096* (2013.01); *H01L 51/5221* (2013.01)

(56) References Cited

U.S. PATENT DOCUMENTS

| | | | |
|---|---|---|---|
| 8,884,316 B2 | 11/2014 | Weaver et al. | |
| 2012/0050215 A1* | 3/2012 | Kim | G06F 3/045 345/174 |
| 2017/0068128 A1* | 3/2017 | Lim | G02F 1/133512 |
| 2017/0077416 A1* | 3/2017 | Kim | H05B 33/20 |
| 2017/0154698 A1* | 6/2017 | Kim | G06F 3/0412 |
| 2018/0261791 A1 | 9/2018 | Yoo et al. | |
| 2018/0370981 A1* | 12/2018 | Nishimae | C07D 495/06 |
| 2019/0019847 A1* | 1/2019 | Lim | C09K 11/025 |
| 2019/0044072 A1* | 2/2019 | Sim | C07F 9/5325 |
| 2019/0229290 A1* | 7/2019 | Kim | C07C 233/24 |
| 2021/0202911 A1* | 7/2021 | Kim | H01L 51/5259 |

FOREIGN PATENT DOCUMENTS

| | | |
|---|---|---|
| KR | 10-2018-0035000 A | 4/2018 |
| KR | 10-2018-0104258 A | 9/2018 |

OTHER PUBLICATIONS

Scholz et al. "Degradation mechanisms and reactions in organic light-emitting devices." Chemical reviews 115, No. 16 (2015): 8449-8503. (Year: 2015).*

* cited by examiner

ORGANIC LIGHT-EMITTING DEVICE AND LIGHT-EMITTING APPARATUS INCLUDING THE SAME

CROSS-REFERENCE TO RELATED APPLICATION

This application claims priority to and the benefit of Korean Patent Application No. 10-2019-0017400, filed on Feb. 14, 2019, in the Korean Intellectual Property Office, the entire content of which is incorporated herein by reference.

BACKGROUND

1. Field

One or more embodiments of the present disclosure relate to an organic light-emitting device and a light-emitting apparatus including the same.

2. Description of the Related Art

Organic light-emitting devices are self-emission devices that produce full-color images, and also have wide viewing angles, high contrast ratios, short response times, and excellent characteristics in terms of brightness, driving voltage, and response speed, as compared to other devices in the art.

An example of such organic light-emitting devices may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

One or more embodiments include an organic light-emitting device and a light-emitting apparatus including the same.

Additional aspects of embodiments will be set forth in part in the description which follows and, in part, will be apparent from the description, or may be learned by practice of the presented embodiments.

An aspect of an embodiment of the present disclosure provides an organic light-emitting device including:
a first electrode;
a second electrode facing the first electrode;
an organic layer between the first electrode and the second electrode and including an emission layer; and
a capping layer on the second electrode,
wherein the capping layer includes an amine-based compound represented by Formula 1 and a radical scavenger:

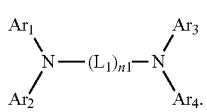

Formula 1

In Formula 1,
$L_1$ may be selected from a substituted or unsubstituted $C_5$-$C_{60}$ carbocyclic group, a substituted or unsubstituted $C_1$-$C_{60}$ heterocyclic group, a substituted or unsubstituted $C_1$-$C_{60}$ alkylene group, *—O—', *—N($R_1$)—', *—(C=O)—O—', and *—O—(C=O)—*', n1 may be an integer from 1 to 5, $Ar_1$ to $Ar_4$ may each independently be selected from groups represented by Formulae 2A to 2C, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $Ar_1$ to $Ara$ may be selected from groups represented by Formulae 2A to 2C:

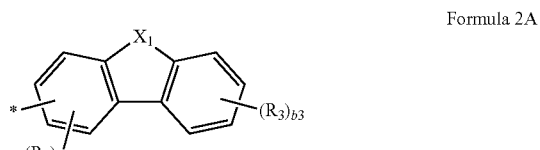

Formula 2A

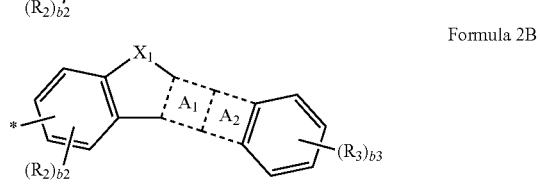

Formula 2B

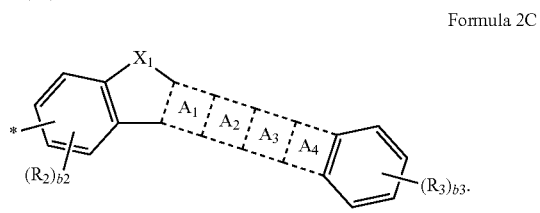

Formula 2C

In Formulae 2A to 2C,
$X_1$ may be selected from $C(R_4)(R_5)$, $Si(R_4)(R_5)$, $N(R_4)$, O, and S, ring $A_1$ and ring $A_3$ may each independently be a substituted or unsubstituted benzene ring, ring $A_1$ may be condensed with a neighboring 5-membered ring, and ring $A_3$ may be condensed with a neighboring 5-membered ring, and ring $A_2$ may be a 5-membered ring represented by Formula 3A, and ring $A_4$ may be a 5-membered ring represented by Formula 3B,

Formula 3A

Formula 3B

In Formulae 3A and 3B,
$X_2$ may be selected from $C(R_6)(R_7)$, $Si(R_6)(R_7)$, $N(R_6)$, O, and S, $X_3$ may be selected from $C(R_8)(R_9)$, $Si(R_8)(R_9)$, $N(R_8)$, O, and S, in Formulae 1, 2A to 2C, 3A, and 3B, $R_1$ to $R_9$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(a)(Q_2)$, —$B(Q_1)(Q_2)$, —$C(=O)(Q_1)$, —$S(=O)_2(Q_1)$, and —$P(=O)(Q_1)(Q_2)$, b2 may be an integer from 1 to 3, b3 may be an integer from 1 to 4, at least one substituent of the substituted $C_5$-$C_{60}$ carbocyclic group, the substituted $C_1$-$C_{60}$ heterocyclic group, the substituted $C_1$-$C_{60}$ alkylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $01$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_5$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

Another aspect of an embodiment of the present disclosure provides a light-emitting apparatus including: a transistor including a source, electrode, a drain electrode, a gate electrode, and an active layer; and the organic light-emitting device, wherein the first electrode of the organic light-emitting device is electrically coupled to one of the source electrode and the drain electrode of the transistor.

BRIEF DESCRIPTION OF THE DRAWINGS

These and/or other aspects of embodiments will become apparent and more readily appreciated from the following description of the embodiments, taken in conjunction with the accompanying drawings in which.

DETAILED DESCRIPTION

Figure 1:
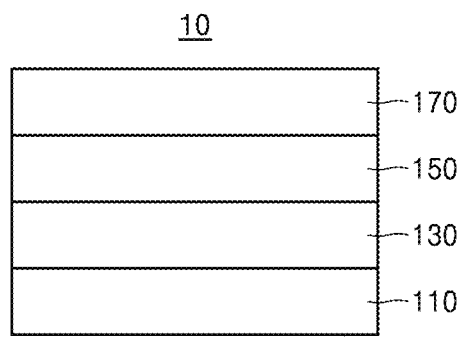
FIG. 1 is a schematic cross-sectional view of an organic light-emitting device according to an embodiment.

Hereinafter, embodiments are described in more detail by referring to the attached drawings, and in the drawings, like reference numerals denote like elements, and a redundant explanation thereof will not be repeated. In the drawings, thicknesses of layers and sizes of regions may be exaggerated for clarity.

It will be understood that although the terms "first", "second", etc. may be used herein to describe various components, these components should not be limited by these terms. These terms are only used to distinguish one component from another.

As used herein, the singular forms "a," "an" and "the" are intended to include the plural forms as well, unless the context clearly indicates otherwise.

It will be further understood that the terms "comprises" and/or "comprising" as used herein specify the presence of stated features or components, but do not preclude the presence or addition of one or more other features or components.

It will be understood that when a layer, region, or component is referred to as being "formed on," another layer, region, or component, it can be directly or indirectly formed on the other layer, region, or component. For example, intervening layers, regions, or components may be present.

An organic light-emitting device according to an embodiment includes: a first electrode; a second electrode facing the first electrode; an organic layer between the first electrode and the second electrode and including an emission layer; and a capping layer on the second electrode, wherein the capping layer includes an amine-based compound represented by Formula 1 and a radical scavenger:

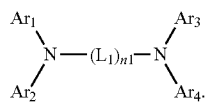

Formula 1

In Formula 1, $L_1$ may be selected from a substituted or unsubstituted $C_5$-$C_{60}$ carbocyclic group, a substituted or unsubstituted $C_1$-$C_{60}$ heterocyclic group, a substituted or unsubstituted $C_1$-$C_{60}$ alkylene group, *—O—*', *—N($R_1$)—*', *—(C=O)—O—*', and *—O—(C=O)—*', n1 may be an integer from 1 to 5, $Ar_1$ to $Ar_4$ may each independently be selected from groups represented by Formulae 2A to 2C, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $Ar_1$ to $Ar_4$ may be selected from groups represented by Formulae 2A to 2C:

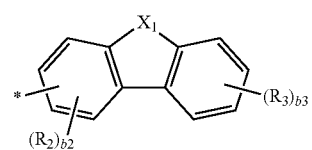

Formula 2A

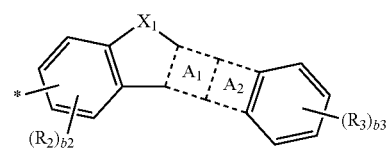

Formula 2B

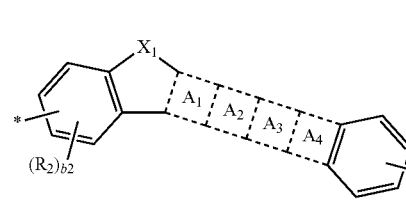

Formula 2C

In Formulae 2A to 2C, $X_1$ may be selected from $C(R_4)(R_5)$, $Si(R_4)(R_5)$, $N(R_4)$, O, and S, ring $A_1$ and ring $A_3$ may each independently be a substituted or unsubstituted benzene ring, ring $A_1$ may be condensed with (e.g., combined with) a neighboring 5-membered ring, and ring $A_3$ may be condensed with (e.g., combined with) a neighboring 5-membered ring, and ring $A_2$ may be a 5-membered ring represented by Formula 3A, and ring $A_4$ may be a 5-membered ring represented by Formula 3B:

Formula 3A

Formula 3B

In Formulae 3A and 3B, $X_2$ may be selected from $C(R_6)(R_7)$, $Si(R_6)(R_7)$, $N(R_6)$, O, and S, and $X_3$ may be selected from $C(R_8)(R_9)$, $Si(R_8)(R_9)$, $N(R_6)$, O, and S.

In Formulae 1, 2A to 2C, 3A, and 3B, $R_1$ to $R_9$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted cycloalkyl group, a substituted or unsubstituted heterocycloalkyl group, a substituted or unsubstituted cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b2 may be an integer from 1 to 3, b3 may be an integer from 1 to 4, and at least one substituent of the substituted $C_6$-$C_{60}$ carbocyclic group, the substituted $C_1$-$C_{60}$ heterocyclic group, the substituted $C_1$-$C_{60}$ alkylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

In one embodiment, $L_1$ in Formula 1 may be selected from:

a cyclobutylene group, a cyclopentylene group, a cyclohexylene group, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, and a dibenzosilolylene group;

a cyclobutylene group, a cyclopentylene group, a cyclohexylene group, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pyridinylene group, a pyrazinylene group, a pyrimidinylene group, a quinolinylene group, an isoquinolinylene group, a benzoquinolinylene group, a naphthyridinylene group, a quinoxalinylene group, a quinazolinylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, and a dibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$); and a substituted or unsubstituted $C_1$-$C_{60}$ alkylene group, *—O—*', *—N($R_1$)—*', *—(C=O)—O—*', and *—O—(C=O)—*', and $Q_{31}$ to $Q_{33}$ and $R_1$ may each independently be selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one or more embodiments, $L_1$ in Formula 1 may be selected from groups represented by Formulae 4-1 to 4-26, a substituted or unsubstituted $C_1$-$C_{20}$ alkylene group, *—O—*', *—(C=O)—O—*', and *—O—(C=O)—*':

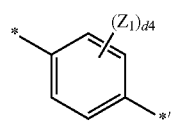

4-1

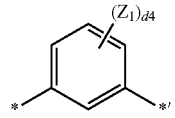

4-2

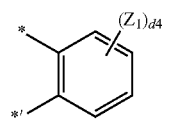

4-3

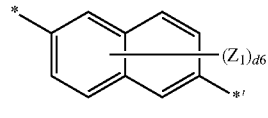

4-4

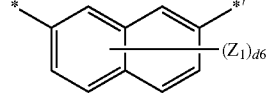

4-5

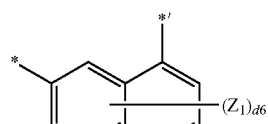

4-6

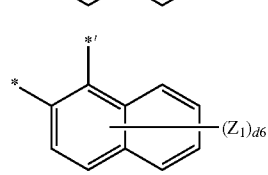

4-7

-continued

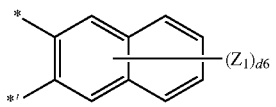

4-8

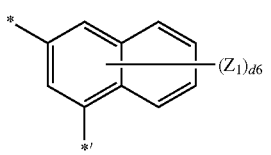

4-9

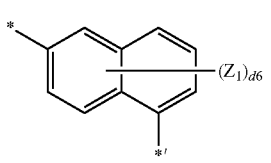

4-10

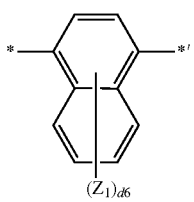

4-11

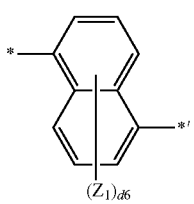

4-12

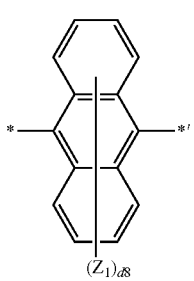

4-13

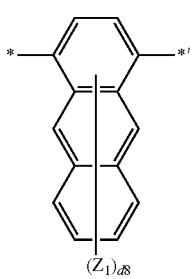

4-14

-continued

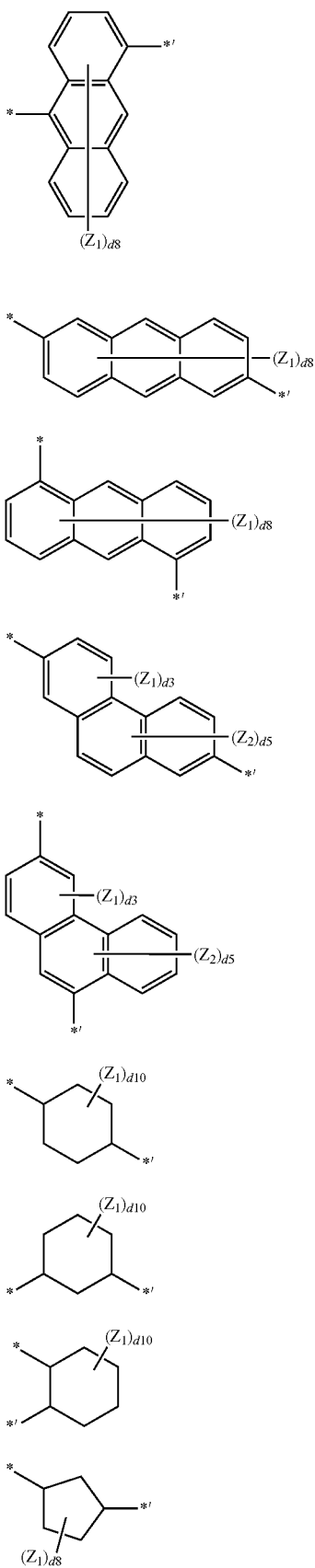

4-15

4-16

4-17

4-18

4-19

4-20

4-21

4-22

4-23

-continued

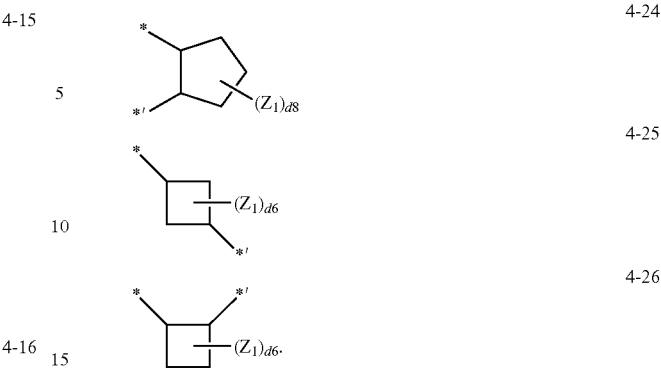

4-24

4-25

4-26

In Formulae 4-1 to 4-26, $Z_1$ and $Z_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a dibenzofuranyl group, a dibenzothiophenyl group, —Si$(Q_{31})(Q_{32})(Q_{33})$, —N$(Q_{31})(Q_{32})$, and —B$(Q_{31})(Q_{32})$, d3 may be an integer from 1 to 3,
d4 may be an integer from 1 to 4,
d5 may be an integer from 1 to 5,
d6 may be an integer from 1 to 6,
d8 may be an integer from 1 to 8,
d10 may be an integer from 1 to 10, $Q_{31}$ to $Q_{33}$ may each independently be selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

In one embodiment, $L_1$ in Formula 1 may be a group represented by Formula 4-1.

In one embodiment, n1 in Formula 1 may be an integer from 1 to 3, and for example, may be 1 or 2.

In one embodiment, $Ar_1$ to $Ar_4$ in Formula 1 may each independently be selected from groups represented by Formulae 2A to 2C, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a banzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, —Si$(Q_{31})(Q_{32})(Q_{33})$, —N$(Q_{31})(Q_{32})$, and —B$(Q_{31})(Q_{32})$ $Q_{31}$ to $Q_{33}$ may each independently be selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one embodiment, in Formula 1, $Ar_1$ and $Ar_3$ may each independently be selected from groups represented by Formulae 2A to 2C, and $Ar_2$ and $Ar_4$ may each independently be selected from:

a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, —Si$(Q_{31})(Q_{32})(Q_{33})$, —N$(Q_{31})(Q_{32})$, and —B$(Q_{31})(Q_{32})$.

In one embodiment, in Formula 1, at least one selected from $Ar_1$ to $Ar_4$ may be selected from groups represented by Formulae 2A, 2B-1 to 2B-6, and 2C-1 to 2C-36:

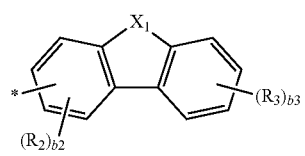

2A

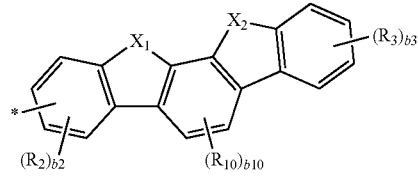

2B-1

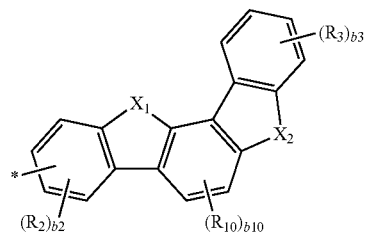

2B-2

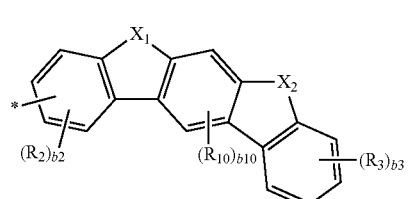

2B-3

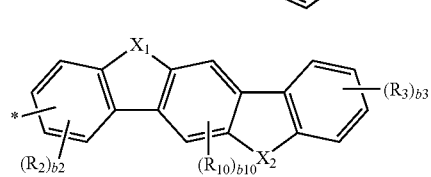

2B-4

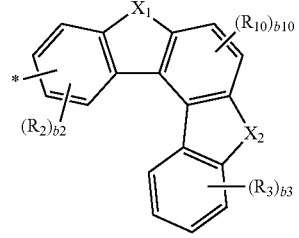

2B-5

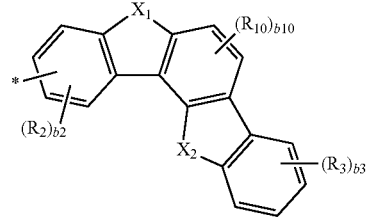

2B-6

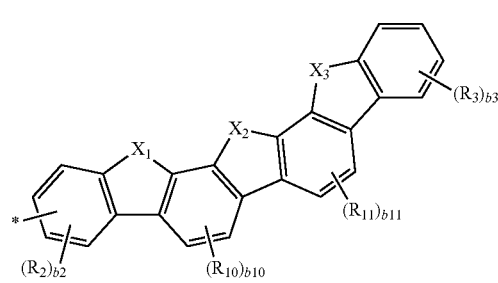

2C-1

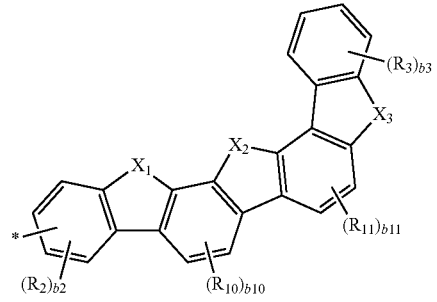

2C-2

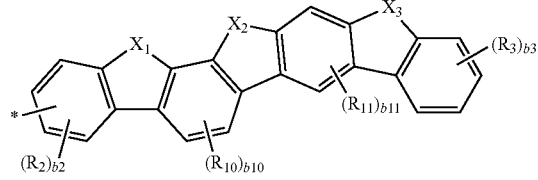

2C-3

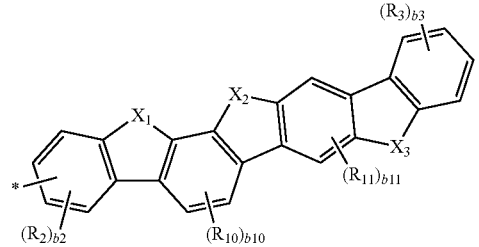

2C-4

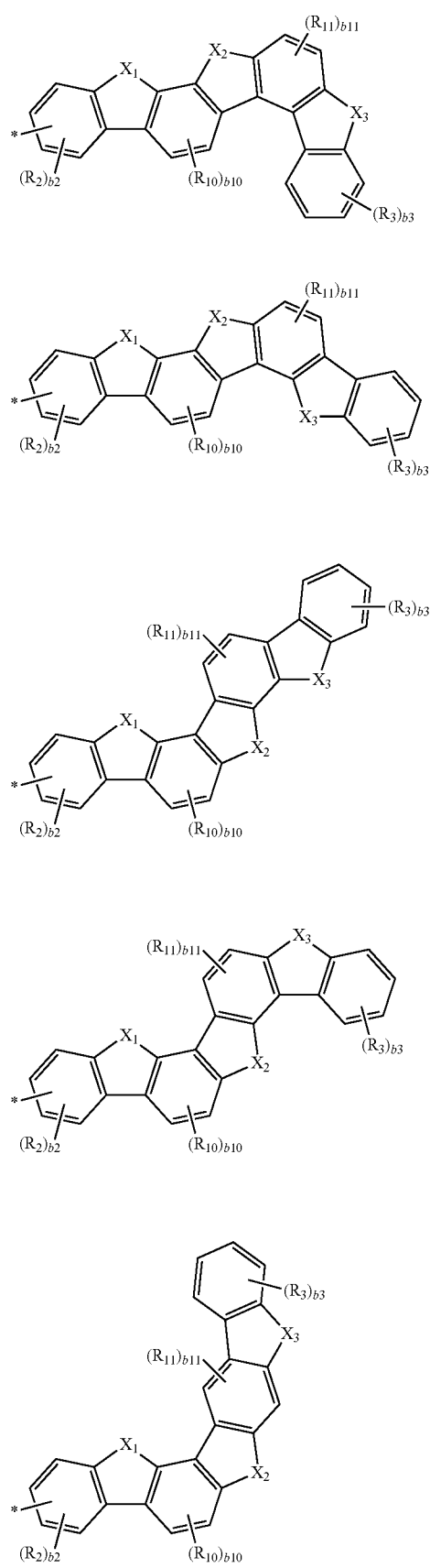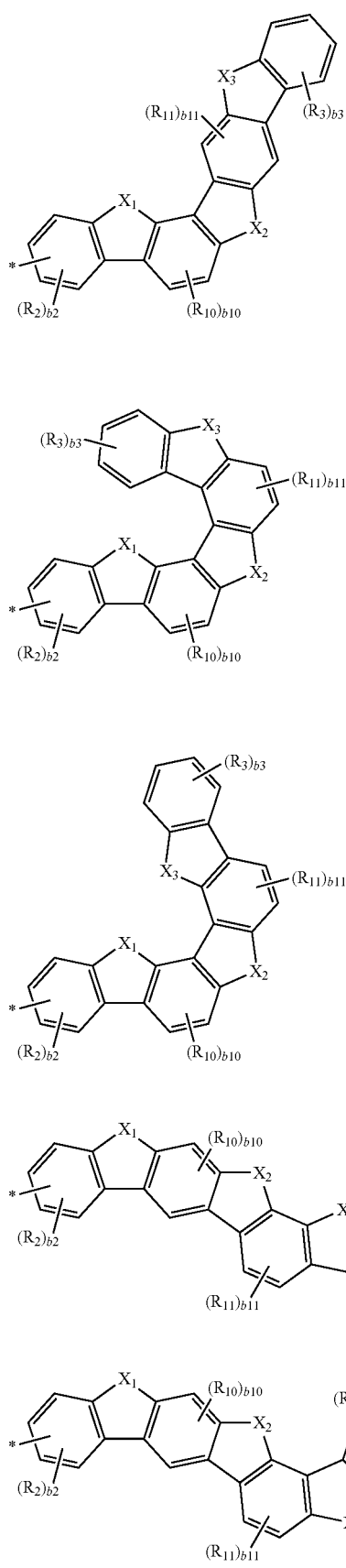

-continued
2C-15
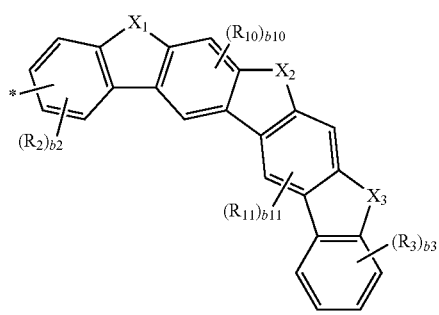
2C-16
2C-17
2C-18
2C-19
-continued
2C-20
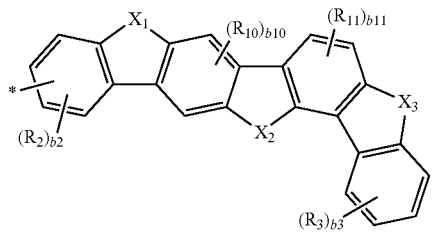
2C-21
2C-22
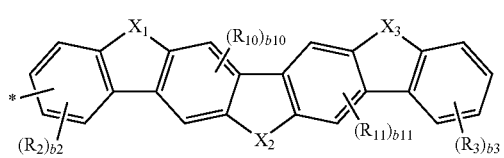
2C-23
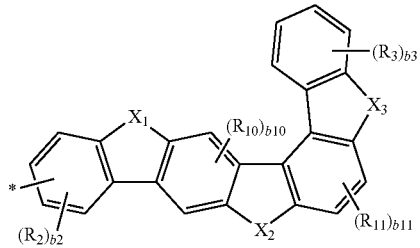
2C-24
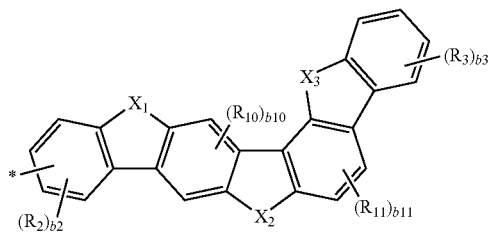
2C-25
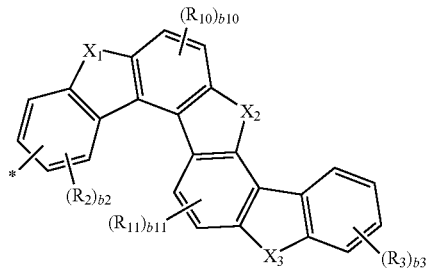

-continued
2C-26
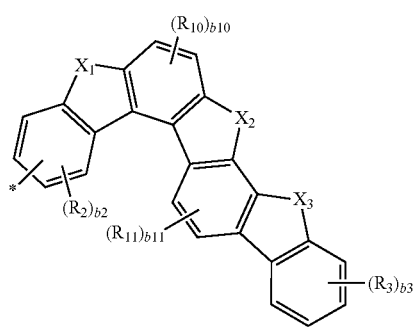
2C-27
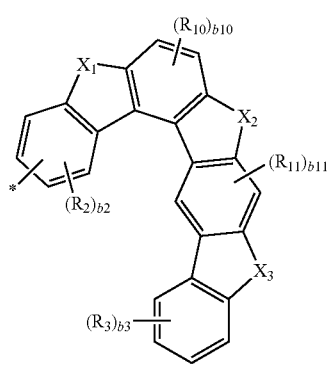
2C-28
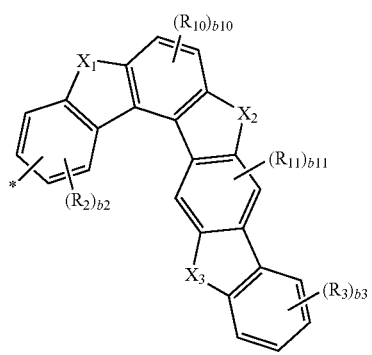
2C-29
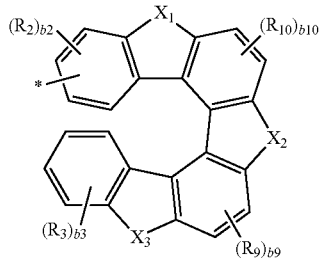
2C-30
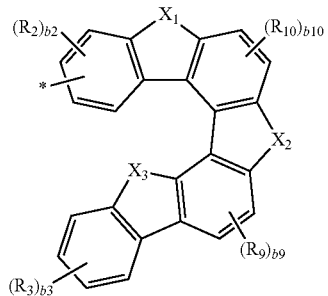
-continued
2C-31
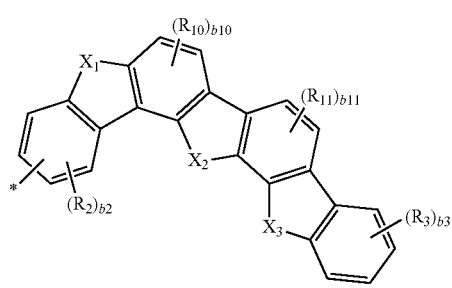
2C-32
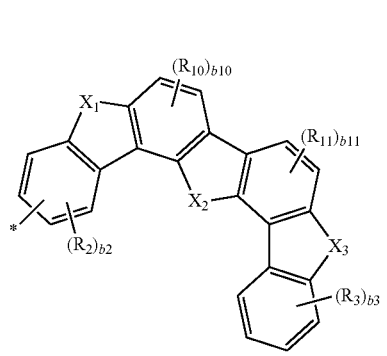
2C-33
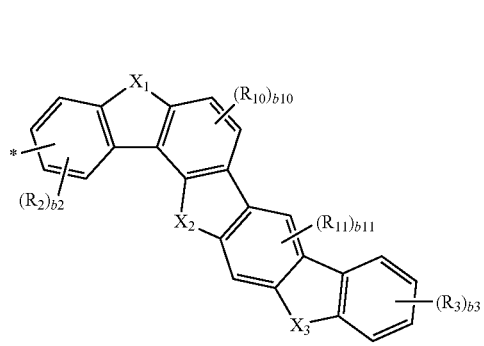
2C-34
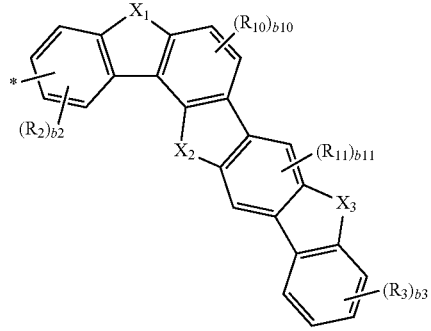
2C-35
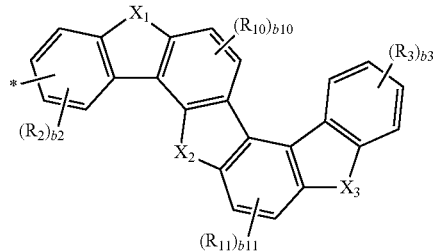

2C-36

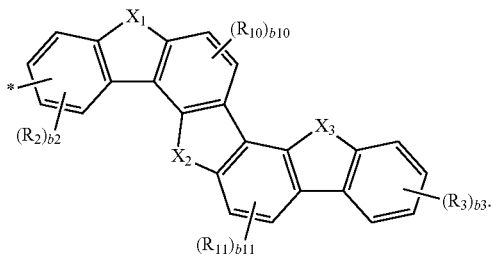

In Formulae 2A, 2B-1 to 2B-6, and 2C-1 to 2C-36, $R_{10}$ and $R_{11}$ may each independently be the same as defined in connection with $R_1$, b10 and b11 may each independently be 1 or 2, $X_1$ to $X_3$, $R_2$, $R_3$, b2, and b3 may each independently be the same as described in Formulae 2A to 2C.

In one embodiment, in Formulae 2A, 2B-1 to 2B-6, and 2C-1 to 2C-36, $X_1$ may be selected from $N(R_4)$, O, and S, $X_2$ may be selected from $C(R_6)(R_7)$, $N(R_6)$, O, and S, $X_3$ may be selected from $C(R_8)(R_9)$, $N(R_8)$, O, and S. For example, $X_1$ may be selected from $N(R_4)$ and S, $X_2$ may be selected from $C(R_6)(R_7)$ and O, and $X_3$ may be selected from $C(R_8)(R_9)$ and $N(R_8)$.

In one embodiment, in Formulae 2A, 2B-1 to 2B-6, and 2C-1 to 2C-36, $R_{10}$ and $R_{11}$ may each independently be selected from hydrogen, —F, —Cl, —Br, —I, a cyano group, a methyl group, an ethyl group, a propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, a hexyl group, a phenyl group, a biphenyl group, a naphthyl group, and a phenalenyl group.

For example, $R_{10}$ and $R_{11}$ may each independently be selected from hydrogen, —F, a cyano group, a tert-butyl group, and a phenyl group.

In one embodiment, at least one selected from $Ar_1$ to $Ar_4$ may be selected from a group represented by Formula 2A, a group represented by Formula 2B-6, and a group represented by Formula 2C-35.

In one embodiment, in Formulae 2A to 2C, $X_1$ may be selected from $N(R_4)$, O, and S, $X_2$ may be selected from $C(R_6)(R_7)$, $N(R_6)$, O, and S, and $X_3$ may be selected from $C(R_8)(R_9)$, $N(R_8)$, O, and S. For example, $X_1$ may be selected from $N(R_4)$ and S, $X_2$ may be selected from $C(R_6)(R_7)$ and O, and $X_3$ may be selected from $C(R_8)(R_9)$ and $N(R_8)$.

In one embodiment, the amine-based compound represented by Formula 1 may be selected from the following compounds:

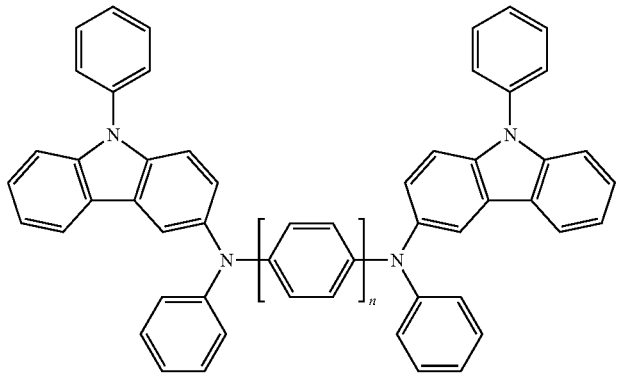

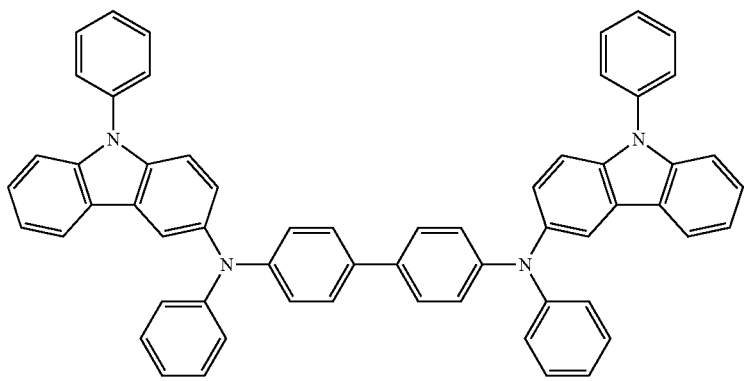

-continued
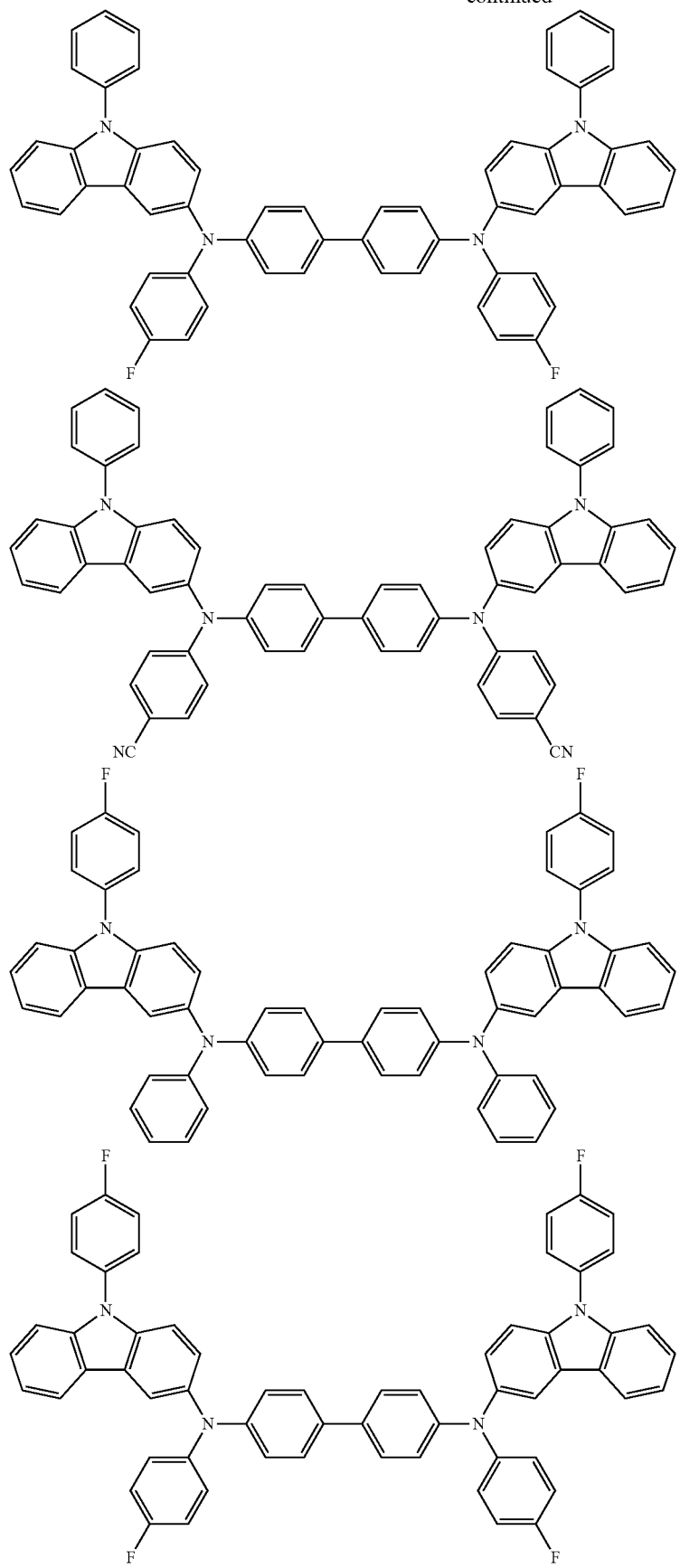

-continued
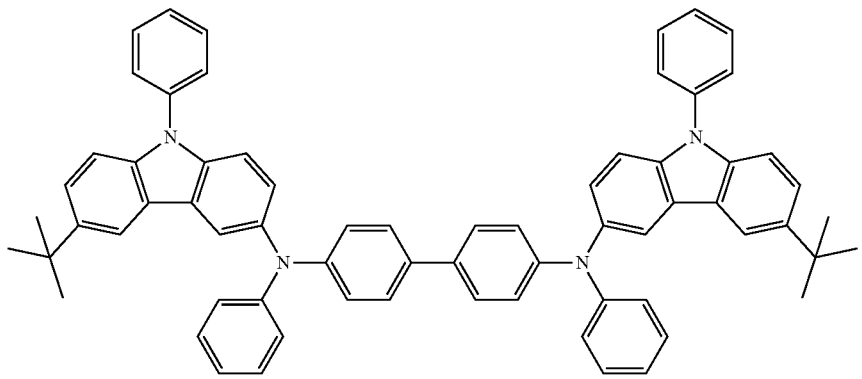
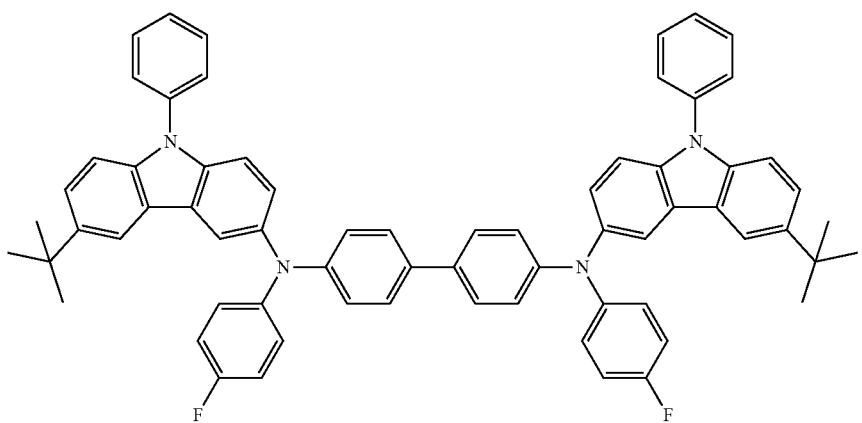
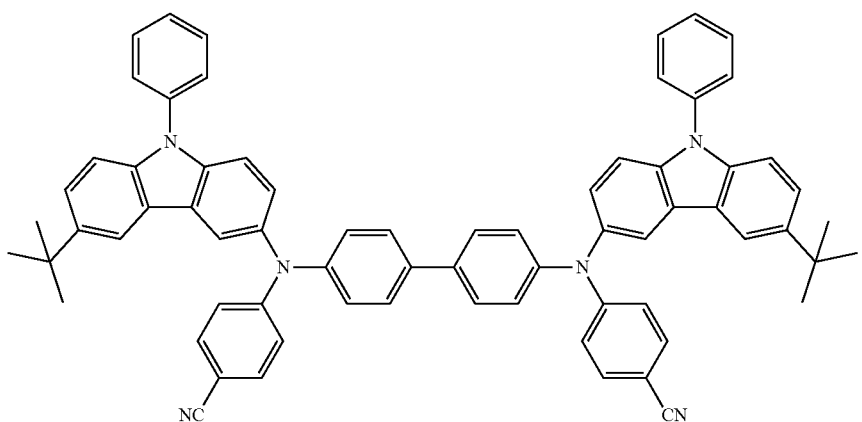
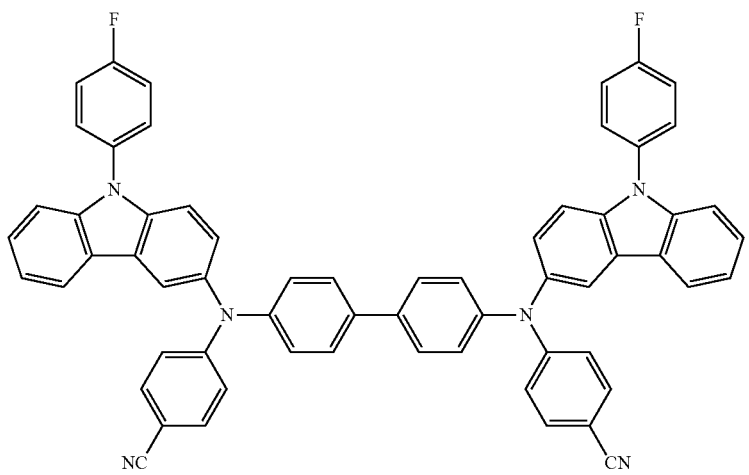

-continued
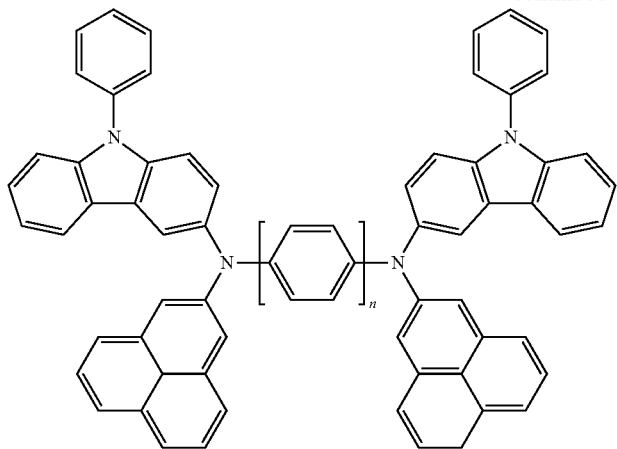
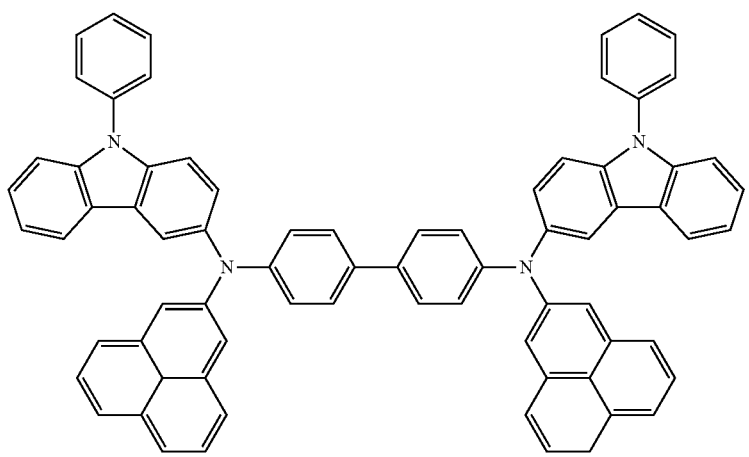
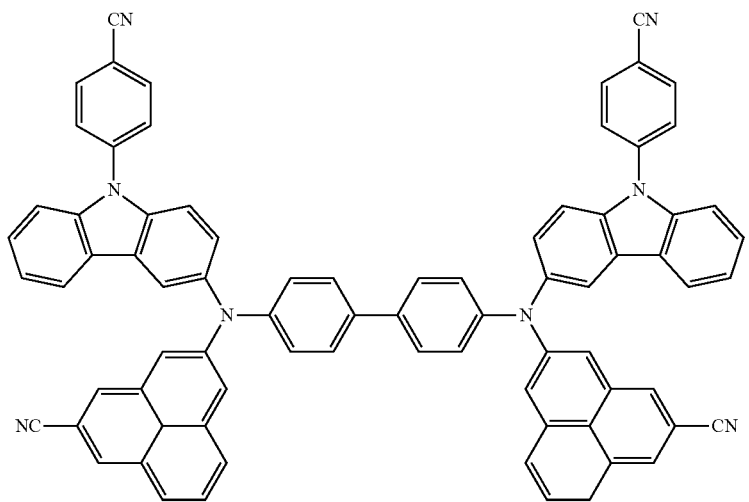

-continued
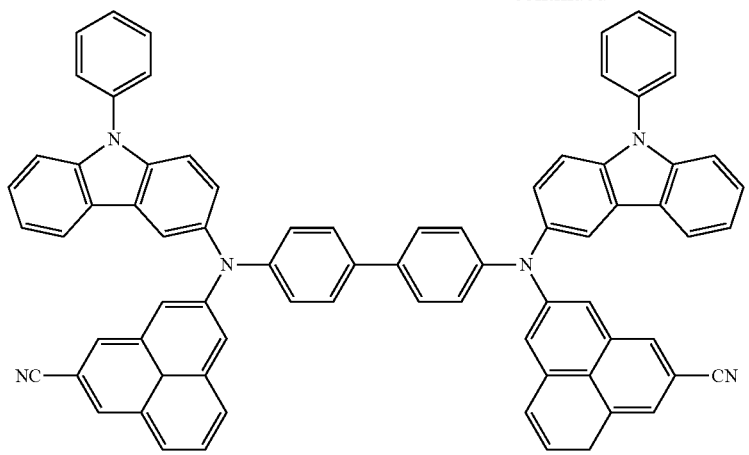
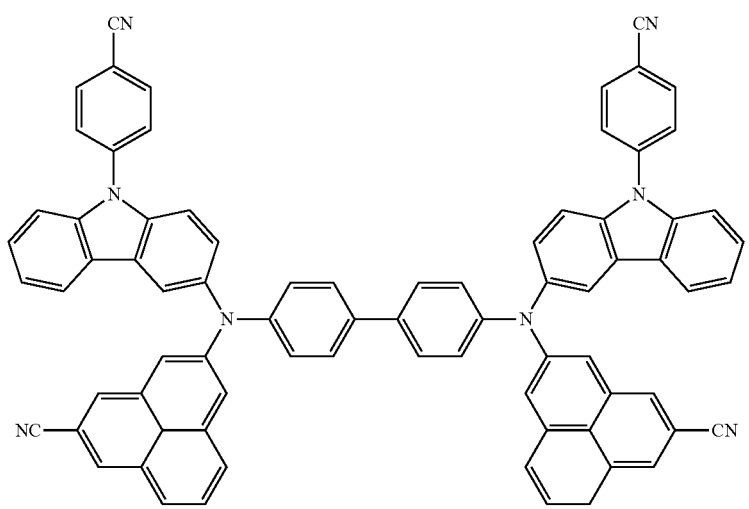
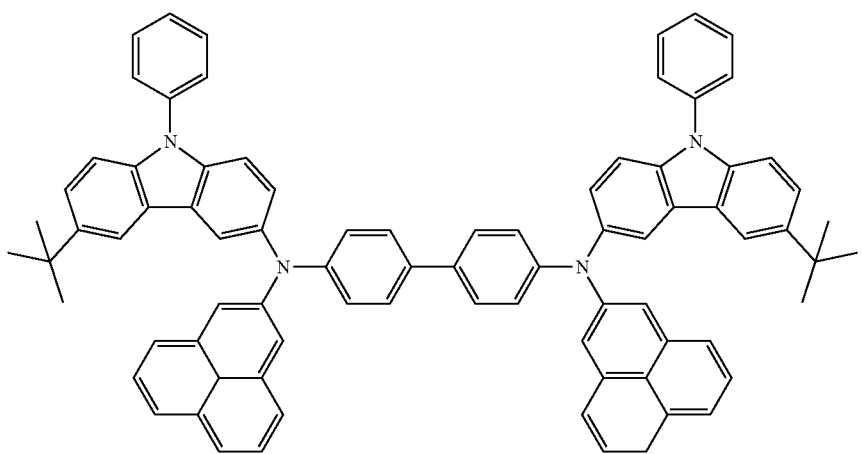

-continued
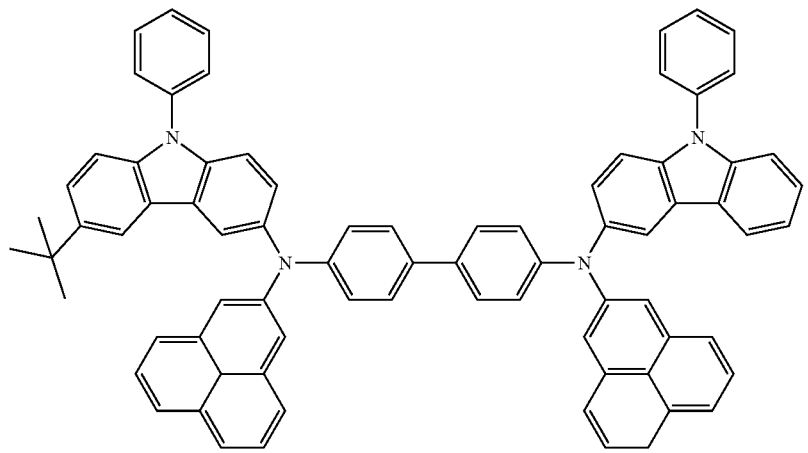
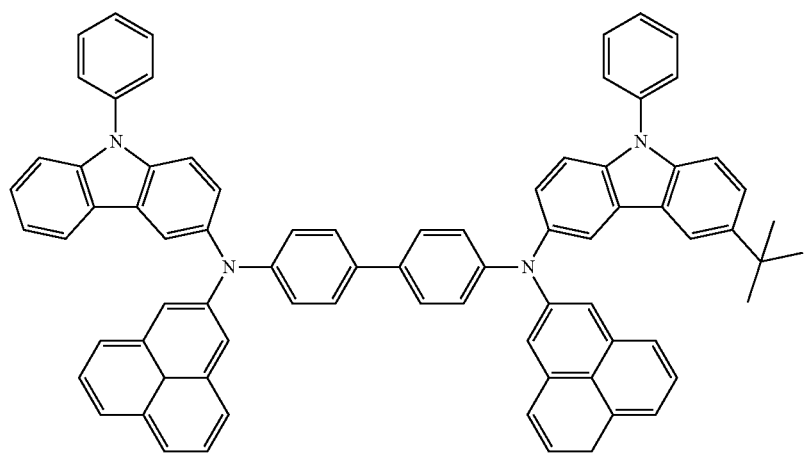
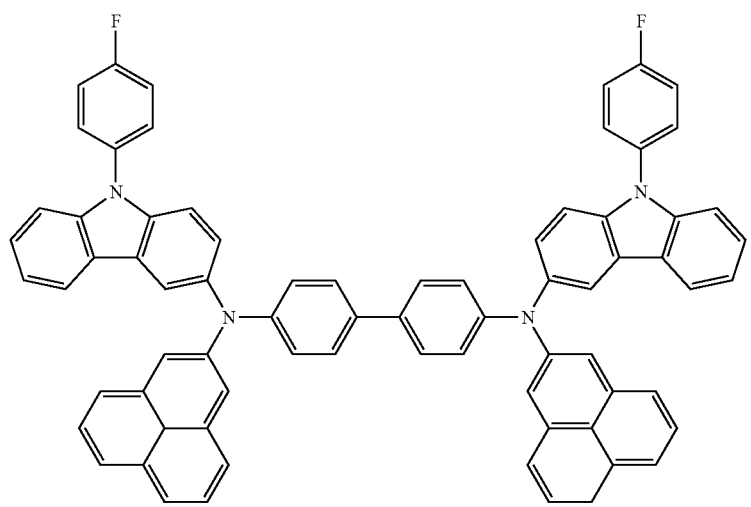

-continued
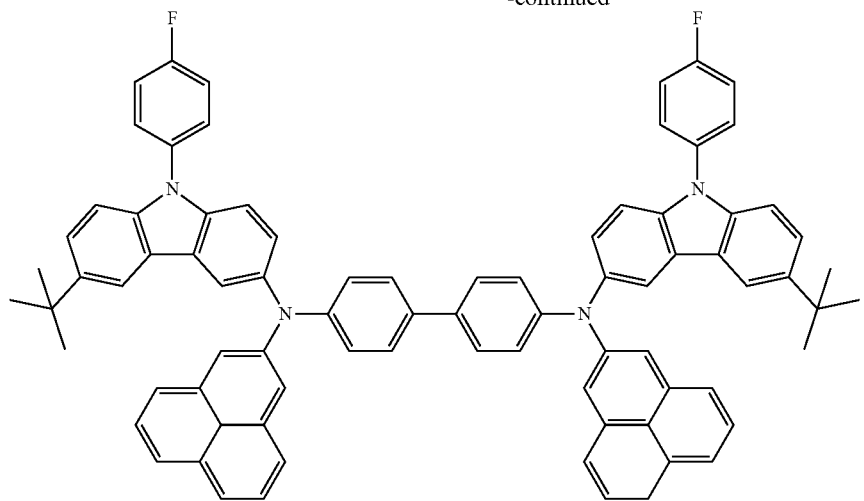
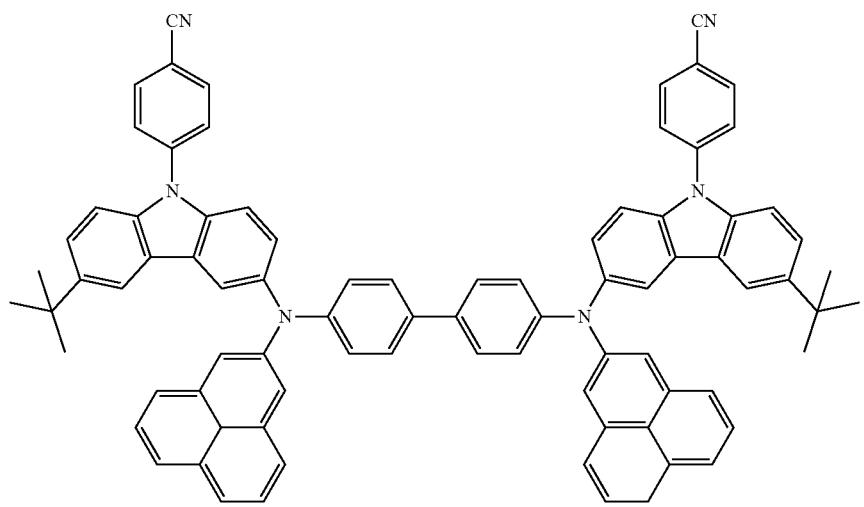
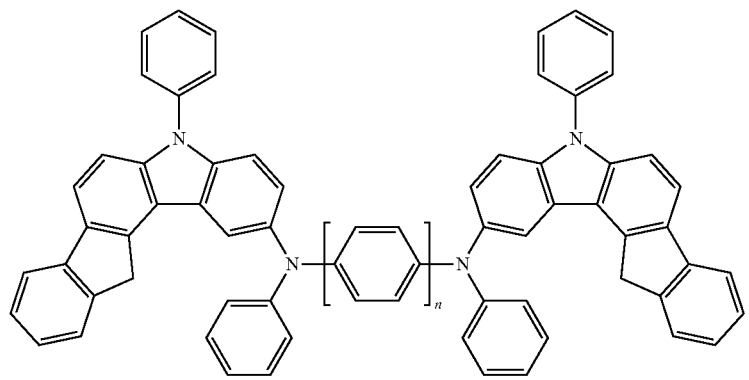

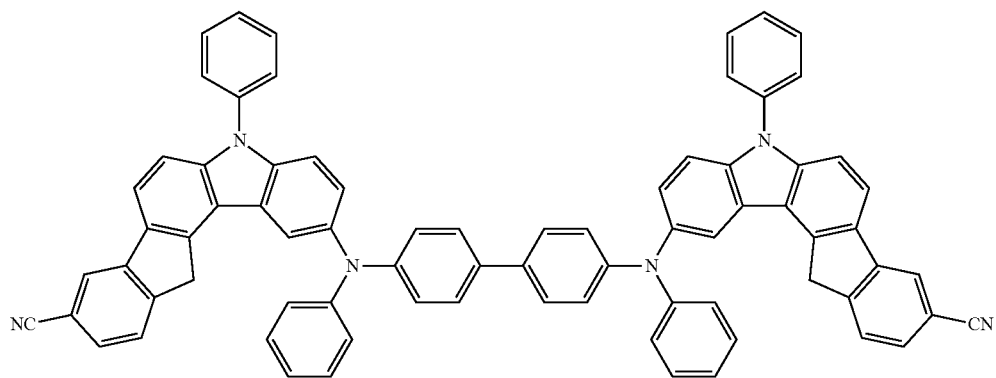
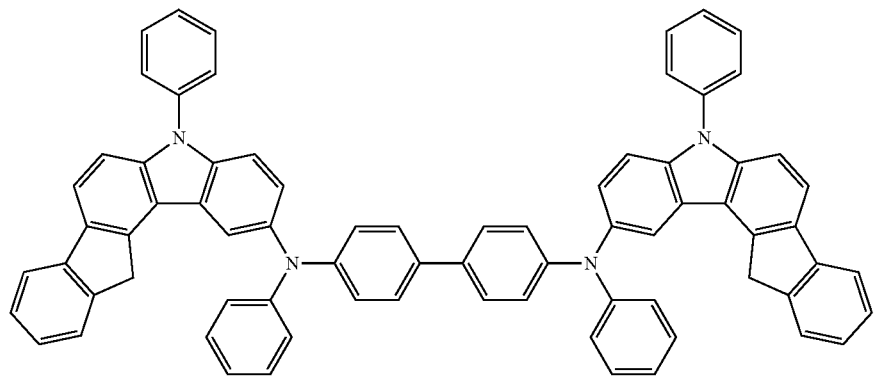
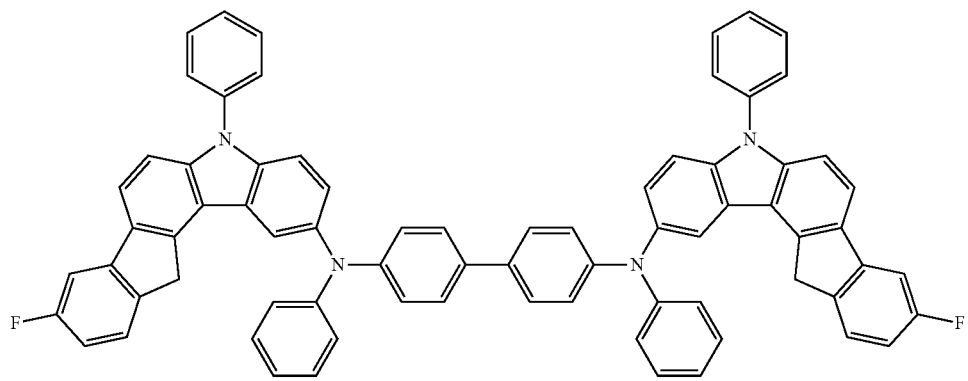
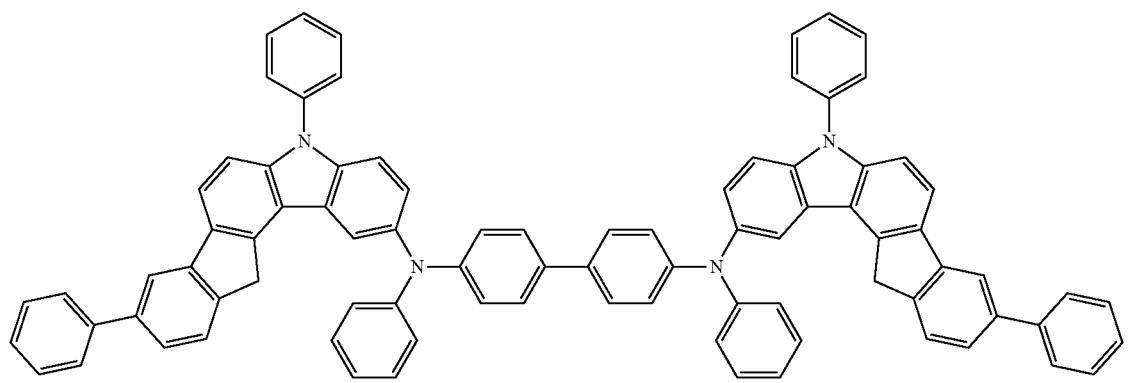

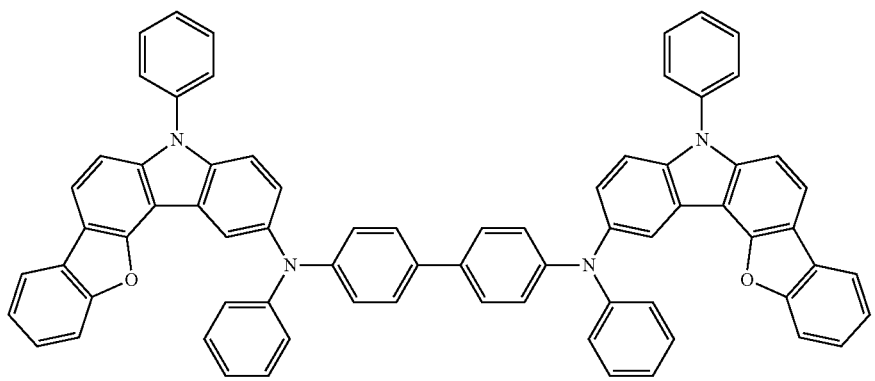
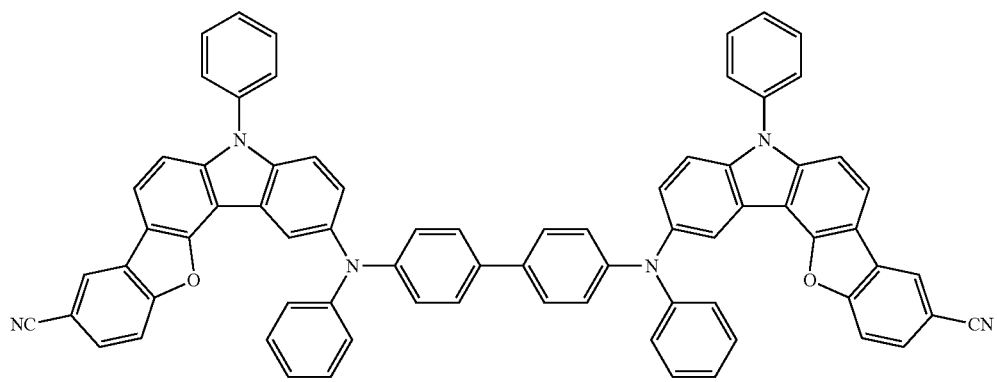
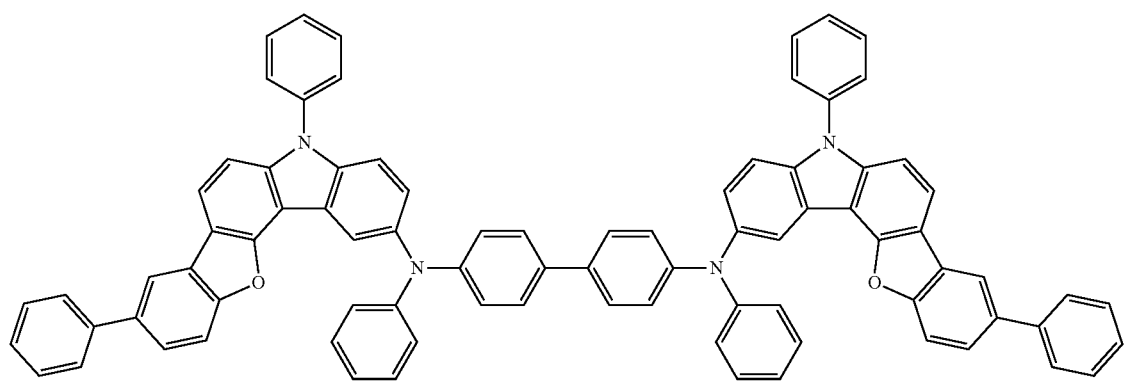
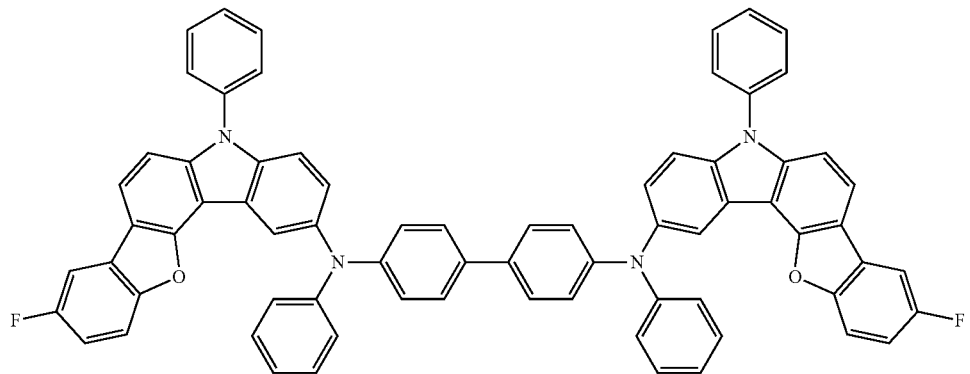

-continued
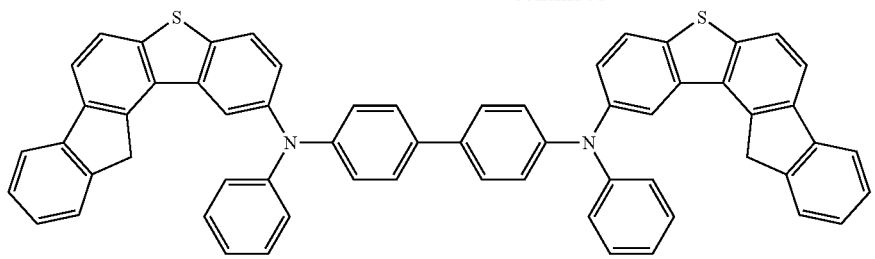
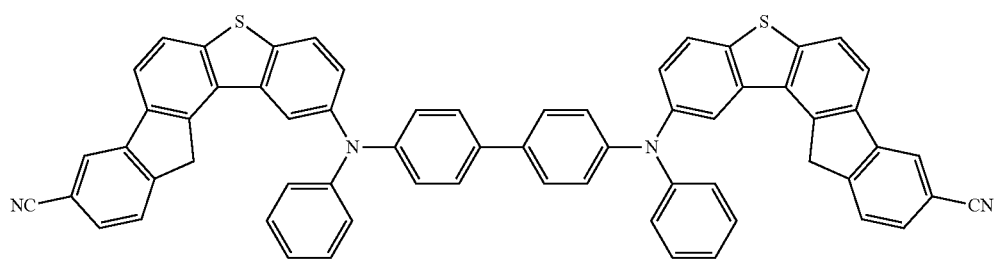
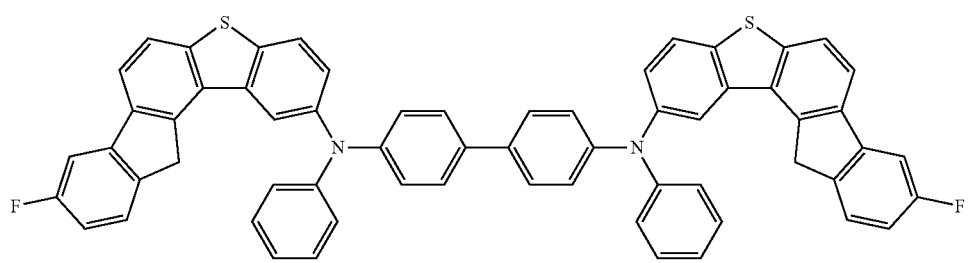
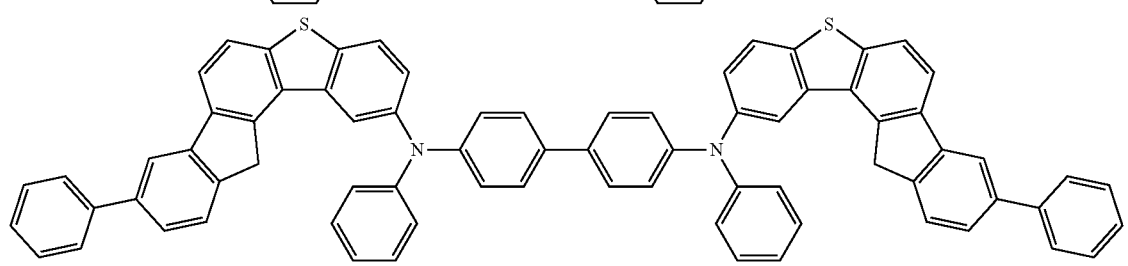
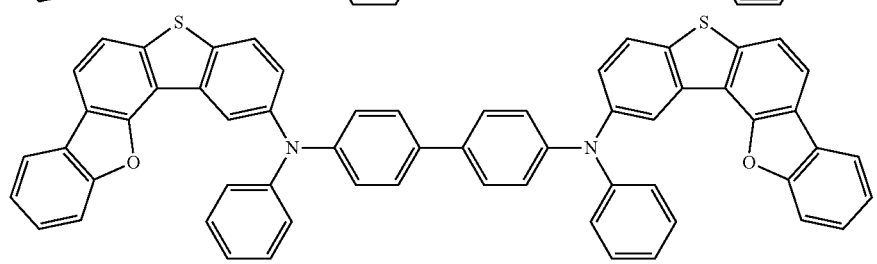
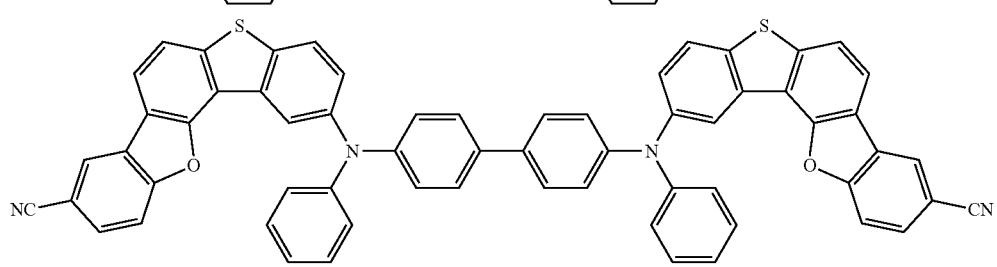

-continued
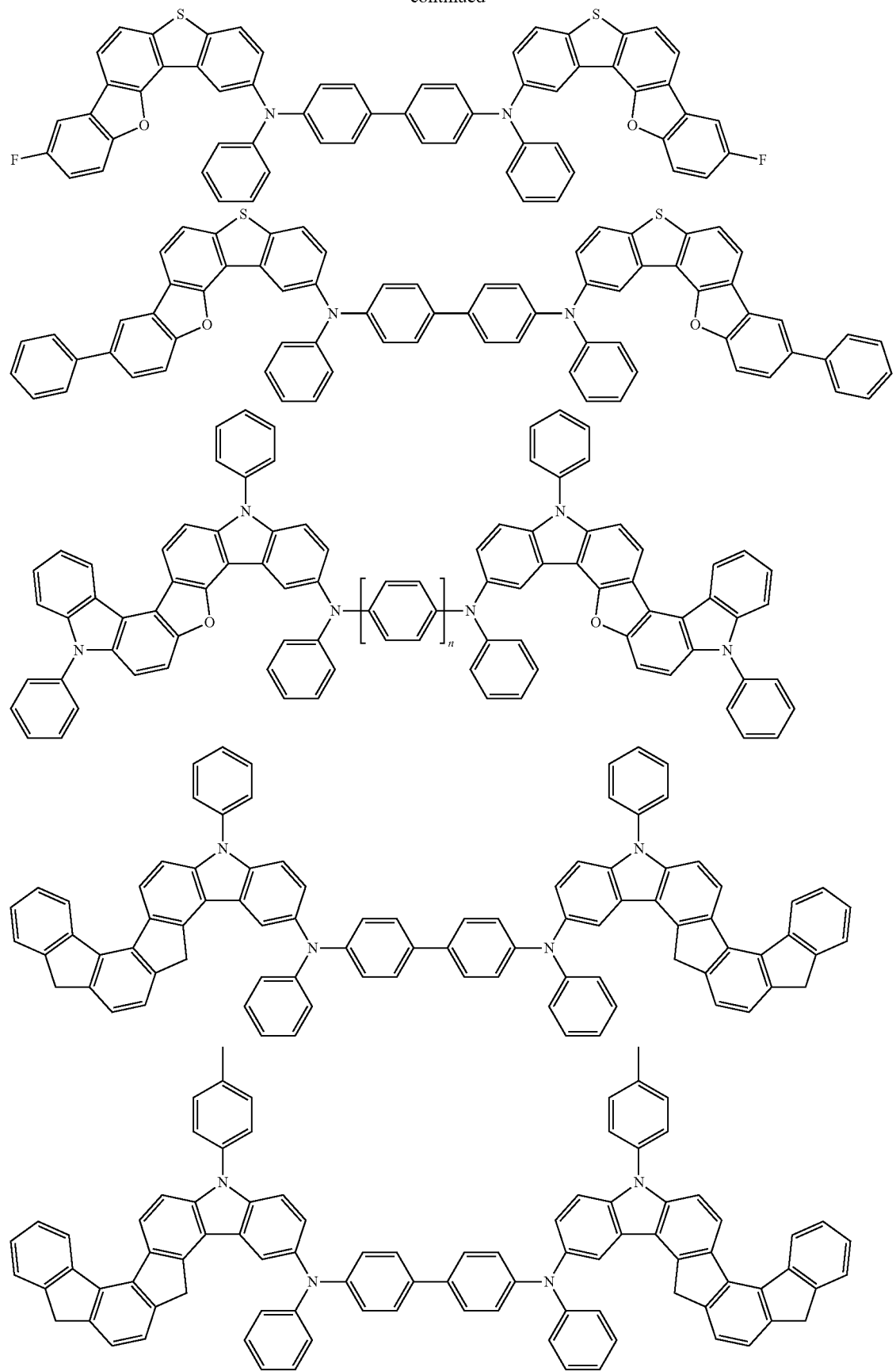

-continued
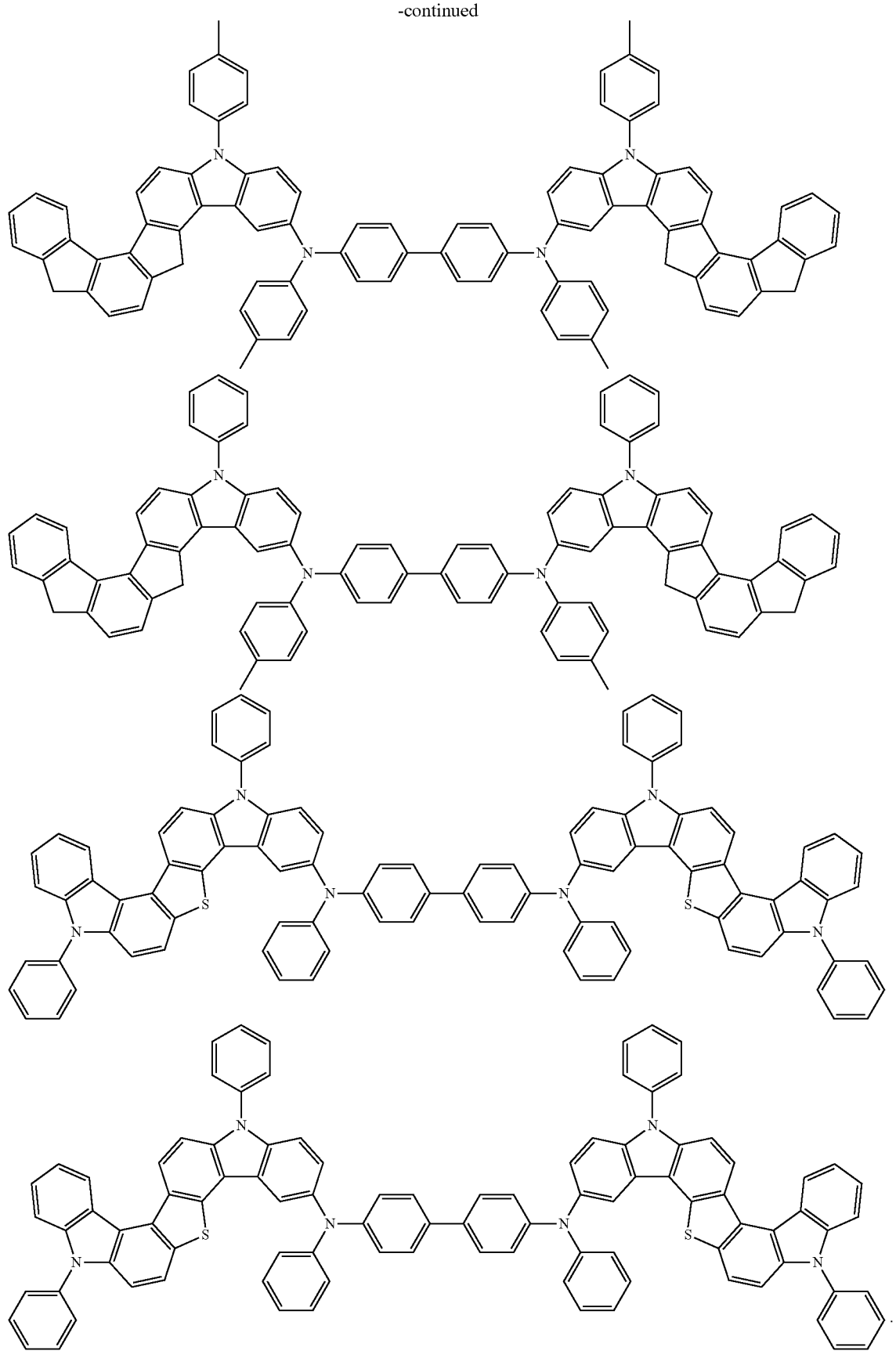

In the compounds, n may be an integer from 1 to 5.

In one embodiment, the radical scavenger may include at least one selected from a first compound represented by Formula 10A and a second compound represented by Formula 10B:

Formula 10A

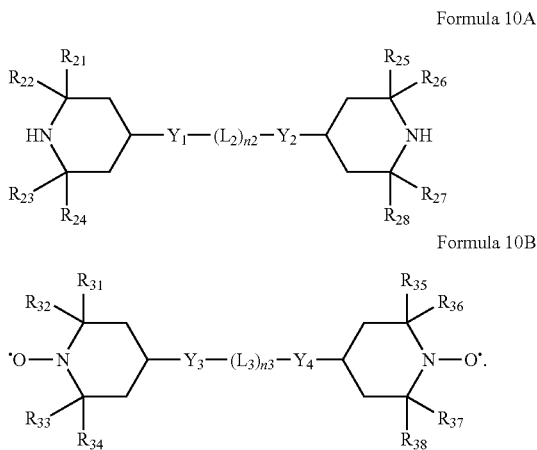

Formula 10B

In Formulae 10A and 10B, $L_2$ and $L_3$ may each independently be selected from a substituted or unsubstituted $C_5$-$C_{60}$ carbocyclic group, a substituted or unsubstituted $C_1$-$C_{60}$ heterocyclic group, a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, *—O—*', *—N($R_{39}$)—*', *—(C=O)—O—*', and *—O—(C=O)—*', n2 and n3 may each independently be an integer from 1 to 5, $Y_1$ to $Y_4$ may each independently be selected from *—O—*', *—(C=O)—O—*', *—O—(C=O)—*', and *—O—(C=O)—O—*', $R_{21}$ to $R_{28}$ and $R_{31}$ to $R_{39}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B(a)($Q_2$), —C(=O)($Q_1$), —S(=O)$_2$(a), and —P(=O)($Q_1$)($Q_2$), at least one substituent of the substituted $C_5$-$C_{60}$ carbocyclic group, the substituted $C_1$-$C_{60}$ heterocyclic group, the substituted $C_1$-$C_{60}$ alkylene group, the substituted $C_2$-$C_{60}$ alkenylene group, the substituted $C_3$-$C_{10}$ cycloalkylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-Coo alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-Coo heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, O' indicates an oxygen radical, and

* and *' each indicate a binding site to a neighboring atom.

In one embodiment, in Formulae 10A and 10B, $L_2$ and $L_3$ may each independently be selected from groups represented by Formulae 4-1 to 4-26, a substituted or unsubstituted $C_1$-$C_{20}$ alkylene group, *—O—*', *—N($R_{39}$)—*', *—(C=O)—O—*', and *—O—(C=O)—*'.

In one or more embodiments, in Formulae 10A and 10B, $L_2$ and $L_3$ may each independently be selected from a $C_1$-$C_{10}$ alkylene group and a $C_1$-$C_{10}$ alkylene group substituted with at least one selected from —F, —Cl, —Br, —I, a cyano group, a Ci-$O_5$ alkyl group, and a $C_1$-$C_5$ alkoxy group.

In one embodiment, in Formulae 10A and 10B, $Y_1$ to $Y_4$ may each independently be selected from *—(C=O)—O—*' and *—O—(C=O)—*'.

In one embodiment, in Formulae 10A and 10B, $R_{21}$ to $R_{28}$ and $R_{31}$ to $R_{39}$ may each independently be selected from hydrogen, a substituted or unsubstituted $C_1$-$C_{60}$ alkyl group, and a substituted or unsubstituted $C_1$-$C_{60}$ alkoxy group.

In one or more embodiments, in Formulae 10A and 10B, $R_{21}$ to $R_{28}$ and $R_{31}$ to $R_{39}$ may each independently be selected from a —$C_1$C alkyl $_{10}$group and a —$C_1C_{10}$ alkyl group substituted with at least one selected from —F, —Cl, —Br, —I, a cyano group, a $C_1$-$C_5$ alkyl group, and a $C_1$-$C_5$ alkoxy group.

In one or more embodiments, in Formulae 10A and 10B, $R_{21}$ to $R_{28}$ and $R_{31}$ to $R_{39}$ may each independently be selected from a methyl group and a methyl group substituted with at least one selected from —F, —Cl, —Br, —I, and a cyano group. For example, each of $R_{21}$ to $R_{28}$ and $R_{31}$ to $R_{39}$ may be a methyl group.

In one embodiment, in Formulae 10A and 10B, $L_2$ and $L_3$ may each independently be selected from a $C_1$-$C_{10}$ alkylene group and a $C_1$-$C_{10}$ alkylene group substituted with at least one selected from —F, —Cl, —Br, —I, a cyano group, a $C_1$-$C_5$ alkyl group, and a $C_1$-$C_5$ alkoxy group, $Y_1$ to $Y_4$ may each independently be selected from *—(C=O)—O—*' and *—O—(C=O)—*', and $R_{21}$ to $R_{28}$ and $R_{31}$ to $R_{38}$ may each independently be selected from a —$C_1C_{10}$ alkyl group and a —$C_1$C alkyl $_{10}$ group substituted with at least one selected from —F, —Cl, —Br, —I, a cyano group, a $C_1$-$C_5$ alkyl group, and a $C_1$-$C_8$ alkoxy group.

In one embodiment, the first compound may be represented by Formula 10A-1, and the second compound may be represented by Formula 10B-1:

Formula 10A-1

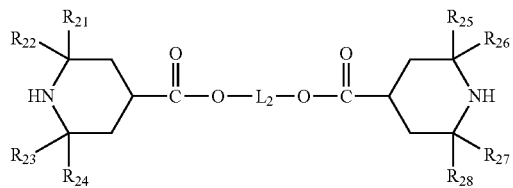

Formula 10B-1

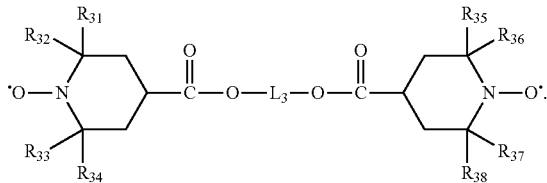

In Formulae 10A-1 and 10B-1, $L_2$, $L_3$, $R_{21}$ to $R_{28}$, and $R_{31}$ to $R_{38}$ may each independently be the same as described in Formulae 10A and 10B.

In one embodiment, in Formulae 10A-1 and 10B-1, $L_2$ and $L_3$ may each independently be selected from a $C_1$-$C_{10}$ alkylene group and a $C_1$-$C_{10}$ alkylene group substituted with at least one selected from —F, —Cl, —Br, —I, a cyano group, a $C_1$-$C_5$ alkyl group, and a $C_1$-$C_8$ alkoxy group, and $R_{21}$ to $R_{28}$ and $R_{31}$ to $R_{38}$ may each independently be selected from a methyl group and a methyl group substituted with at least one selected from —F, —Cl, —Br, —I, and a cyano group.

In one or more embodiments, in Formulae 10A-1 and 10B-1, $L_2$ and $L_3$ may each independently be selected from a $C_1$-$C_{10}$ alkylene group and a $C_1$-$C_{10}$ alkylene group substituted with at least one selected from —F, —Cl, —Br, —I, a cyano group, a $C_1$-$C_5$ alkyl group, and a $C_1$-$C_5$ alkoxy group, and each of $R_{21}$ to $R_{28}$ and $R_{31}$ to $R_{38}$ may be a methyl group.

In one or more embodiments, in Formulae 10A-1 and 10B-1, $L_2$ and $L_3$ may each independently be selected from a $C_2$-$C_5$ alkylene group and a $C_2$-$C_8$ alkylene group substituted with at least one selected from —F, —Cl, —Br, —I, a cyano group, a $C_1$-$C_5$ alkyl group, and a $C_1$-$C_5$ alkoxy group, and each of $R_{21}$ to $R_{28}$ and $R_{31}$ to $R_{38}$ may be a methyl group.

In one embodiment, i) the radical scavenger may include only the first compound;

ii) the radical scavenger may include only the second compound; or iii) the radical scavenger may include the first compound and the second compound at a weight ratio of about 1:9 to about 9:1.

In one embodiment, an amount of the radical scavenger may be in a range of about 0.01 parts by weight to about 5 parts by weight based on 100 parts by weight of the capping layer.

Because the capping layer included in the organic light-emitting device includes the radical scavenger, it is possible to reduce the amount of radicals formed by application of UV light to the organic light-emitting device or the light-emitting apparatus including the organic light-emitting device.

For example, when the UV light is applied to the light-emitting apparatus, out-gassing occurs in an organic layer (for example, a pixel defining layer) of the light-emitting apparatus, and radicals may be generated by components that are out-gassed. Because the radicals generated in the organic layer cause the oxidation of the second electrode, the pixel shrinkage of the organic light-emitting device may occur (e.g., as a result of the out-gassing).

For example, due to the exposure to the UV light, the radical concentration in the light-emitting apparatus may be increased by a mechanism such as the Reaction Scheme 1 below. However, the Reaction Scheme 1 is merely an example of a process in which the radical concentration in the light-emitting apparatus is increased, and the process of generating the radicals due to the exposure to the UV light is not limited to this mechanism.

Reaction Scheme 1

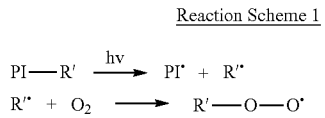

Referring to the Reaction Scheme 1, when a pixel defining layer to be described herein below is a polyimide (PO-based organic layer, a polyimide resin is exposed to UV light and a primary radical source is formed. For example, Pl-R' may be a polyimide chain, and Pl- and R'. may be radicals of a polyimide chain fragment formed by decomposing the polyimide chain. The primary radical source may react with oxygen, which is at least one of components of the outgassing generated in the light-emitting apparatus by the irradiation of the UV light, to thereby form secondary radicals.

Because the organic light-emitting device includes a material capable of removing or reducing the concentration of the radicals, it is possible to minimize or reduce the influence of the UV light on the organic light-emitting device and prevent or reduce the pixel shrinkage of the emission region due to the UV light.

For example, the radical scavenger may react with the radicals in the light-emitting apparatus. For example, the radical scavenger may prevent or reduce sequential generation of radicals through the Denisov cycle (illustrated below).

During the removal (or reduction in the concentration) of the radicals through the circulation process called the Denisov cycle, the radical component is converted to a non-radical product by reaction with the radical scavenger, and the radical scavenger is regenerated.

In one embodiment, the capping layer of the organic light-emitting device may contact (e.g., physically contact) the second electrode.

In one embodiment, the first electrode may be an anode, the second electrode may be a cathode, and the capping layer may contact (e.g., physically contact) the cathode.

In one embodiment, the first electrode may be an anode, and the second electrode may be a cathode, and the organic layer may further include a hole transport region between the first electrode and the emission layer and an electron transport region between the emission layer and the second electrode, and the hole transport region may include a hole injection layer, a hole transport layer, an emission auxiliary layer, an electron blocking layer, or any combination thereof, and the electron transport region includes a buffer layer, a hole blocking layer, an electron control layer, an electron transport layer, an electron injection layer, or any combination thereof.

In one embodiment, the hole transport region of the organic light-emitting device may further include a p-dopant having a lowest unoccupied molecular orbital (LUMO) energy level of −3.5 eV or less.

In one embodiment, the electron transport region of the organic light-emitting device may include a metal-containing material, and the metal-containing material may be a $L_1$ complex. For example, the $L_1$ complex may be a phosphorescent dopant.

In one embodiment, the organic light-emitting device may satisfy Equation 1:

$$\Delta CT = |CT_1 - CT_2| \leq 400 \text{ K}.$$

In Equation 1, $CT_1$ is a color temperature measured before irradiation of UV light on the organic light-emitting device, and $CT_2$ is a color temperature measured after irradiation of UV light on the organic light-emitting device.

The term "organic layer," as used herein, refers to a single layer and/or a plurality of layers between the first electrode and the second electrode of the organic light-emitting device. A material included in the "organic layer" is not limited to an organic material. For example, the "organic layer" may include an inorganic material.

Description of FIG. 1

FIG. 1 is a schematic cross-sectional view of an organic light-emitting device 10 according to an embodiment. The organic light-emitting device 10 includes a first electrode 110, an organic layer 130, a second electrode 150, and a capping layer 170.

Hereinafter, the structure of the organic light-emitting device 10 according to an embodiment and a method of manufacturing the organic light-emitting device 10 will be described in connection with FIG. 1.

First Electrode 110

A substrate may be additionally under the first electrode 110. The substrate may be a glass substrate or a plastic substrate, each having excellent mechanical strength, thermal stability, transparency, surface smoothness, ease of handling, and water resistance.

The first electrode 110 may be formed by, for example, depositing or sputtering a material for forming the first electrode 110 on the substrate. When the first electrode 110

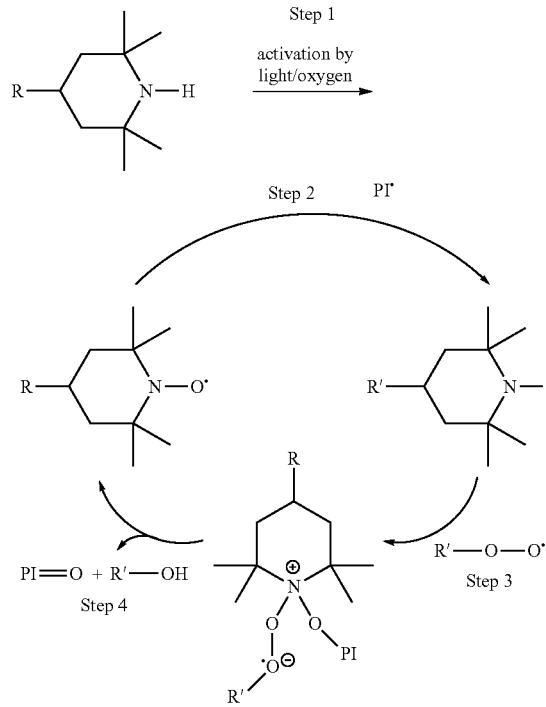

is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 130

The organic layer 130 may be on the first electrode 110. The organic layer 130 may include an emission layer.

The organic layer 130 may further include a hole transport region between the first electrode 110 and the emission layer and an electron transport region between the emission layer and the second electrode 150.

Hole Transport Region in Organic Layer 130

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), p-NPB, TPD, Spiro-TPD, Spiro-NPB, methylated-NPB, TAPC, HMTPD, 4,4', 4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202.

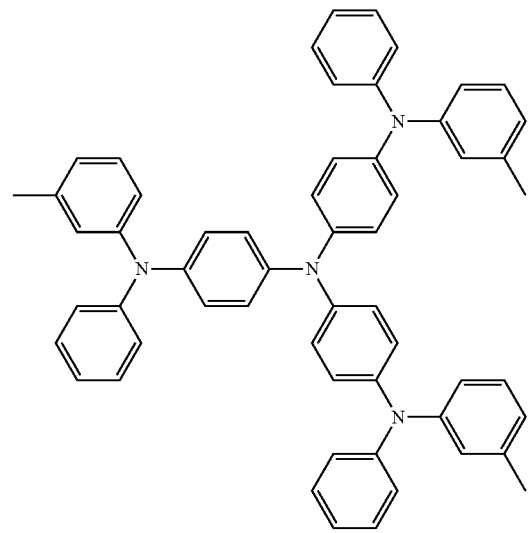

m-MTDATA

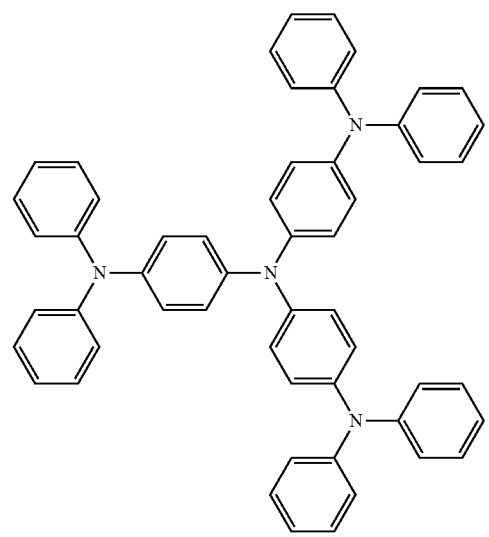

TDATA

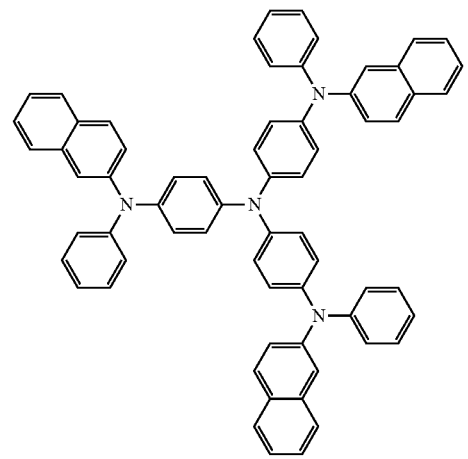

2-TNATA

-continued

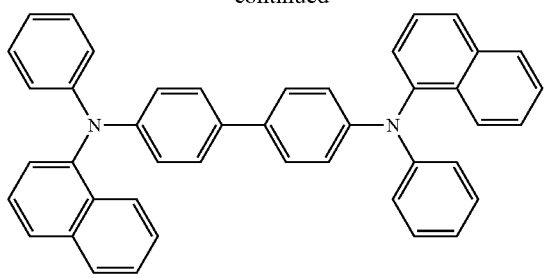

NPB

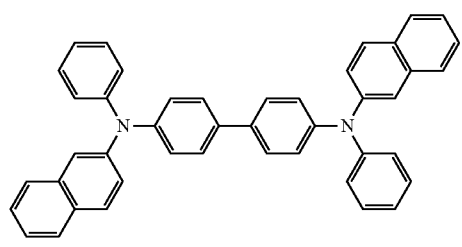

β-NPB

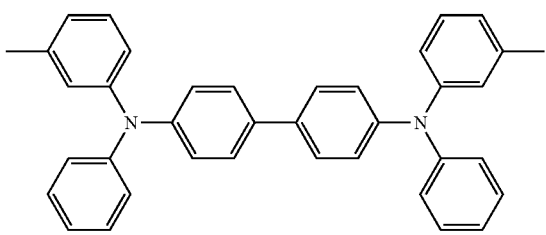

TPD

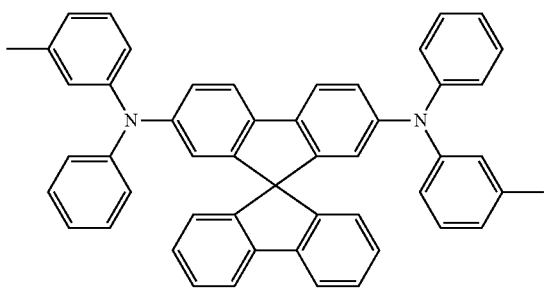

Spiro-TPD

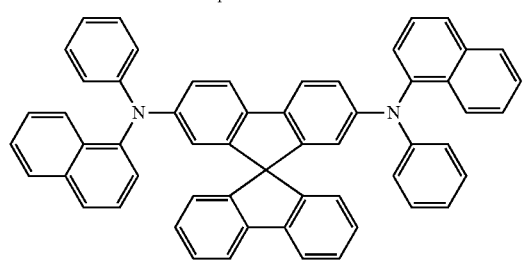

Spiro-NPB

-continued

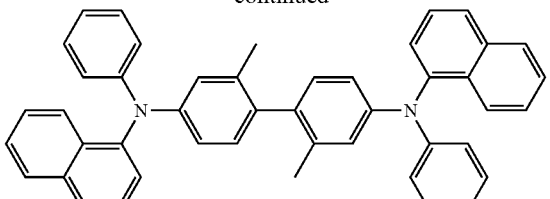

methylated NPB

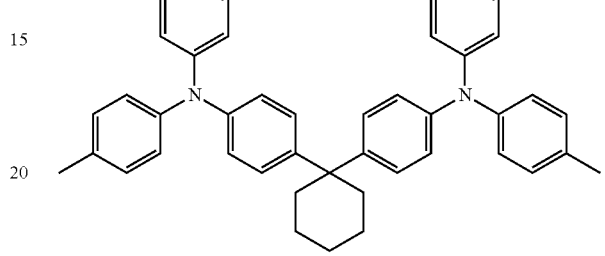

TAPC

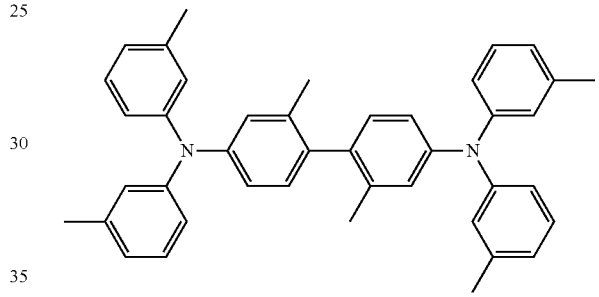

HMTPD

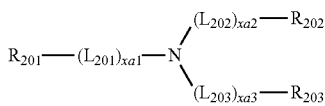

Formula 201

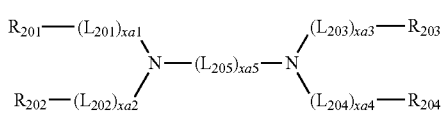

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)—*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-m ethylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, -a phenyl group substituted with a $C_1$Calkyl group $_{10}$, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, and —$N(Q_{31})(Q_{32})$, and $Q_{31}$ to $Q_{33}$ may each independently be selected from a —$C_1C$ alkyl $_{10}$group, a alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, -a phenyl group substituted with a $C_1C$alkyl $_{10}$ group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, and —$N(Q_{31})(Q_{32})$, and $Q_{31}$ to $Q_{33}$ are the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, -a phenyl group substituted with a $C_1C$alkyl group $_{10}$, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl-group substituted with a $CiC$alkyl group 10, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

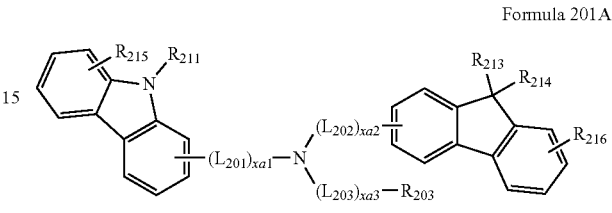

Formula 201A

For example, the compound represented by Formula 201 may be represented by Formula 201A(1), but embodiments of the present disclosure are not limited thereto:

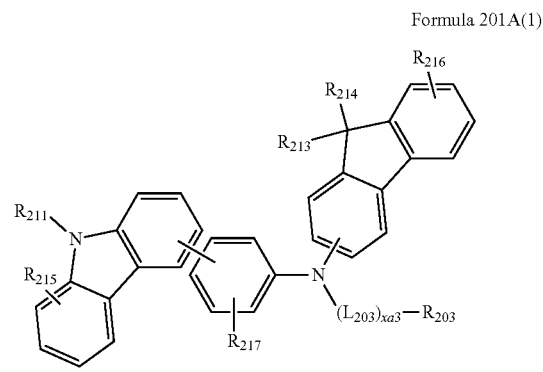

Formula 201A(1)

In one embodiment, the compound represented by Formula 201 may be represented by Formula 201A-1, but embodiments of the present disclosure are not limited thereto:

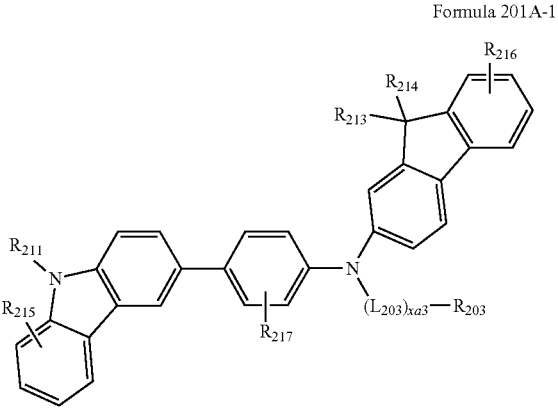

Formula 201A-1

In one embodiment, the compound represented by Formula 202 may be represented by Formula 202A:

Formula 202A

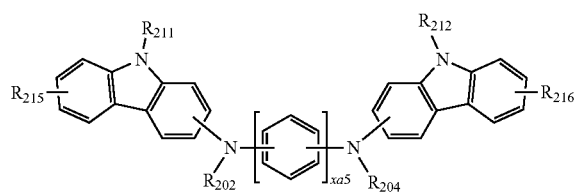

In one embodiment, the compound represented by Formula 202 may be represented by Formula 202A-1:

Formula 202A-1

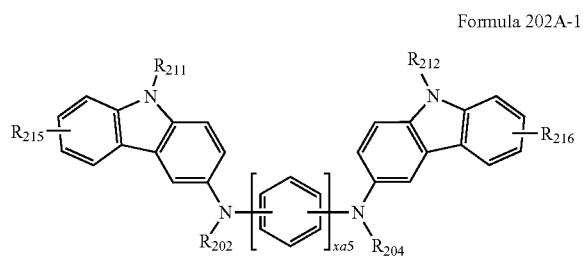

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may each independently be the same as defined in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl-group substituted with a $C_1$Calkyl group $_{10}$, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

HT1

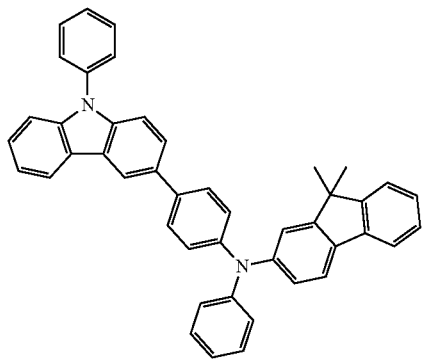

HT2

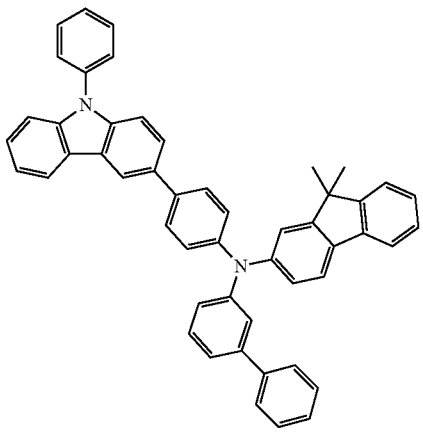

HT3

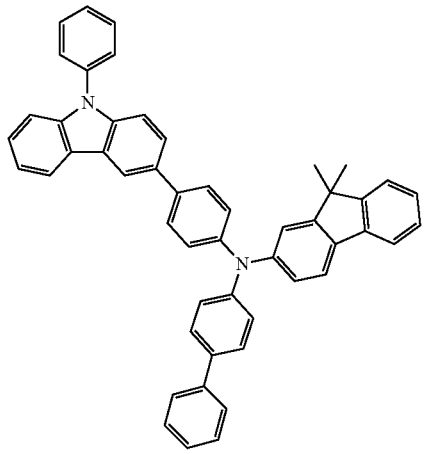

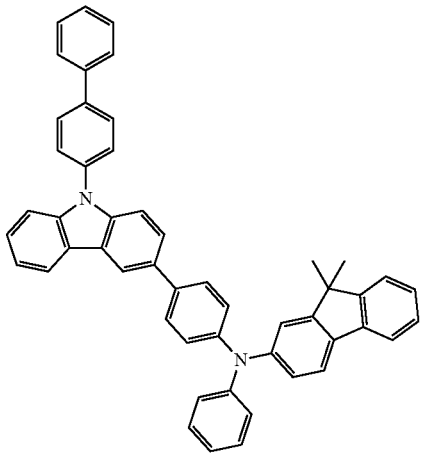

-continued
| HT5 | HT6 |
|---|---|
| 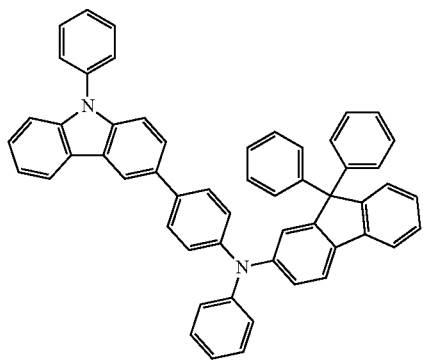 | 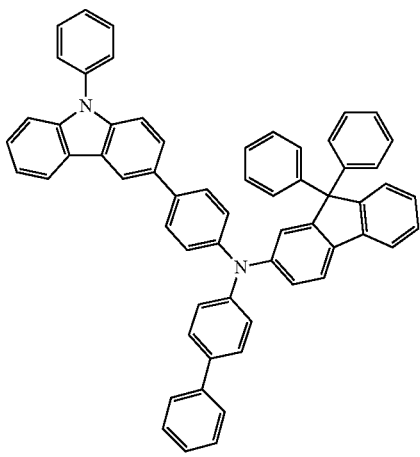 |
| HT7 | HT8 |
| 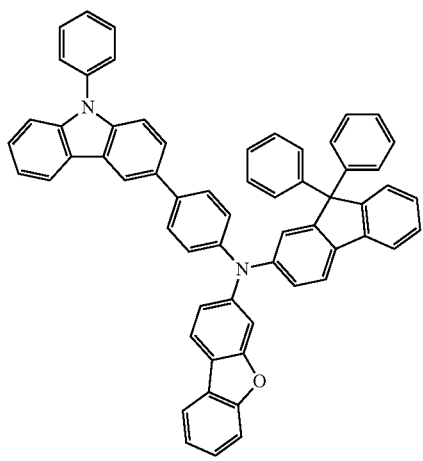 | 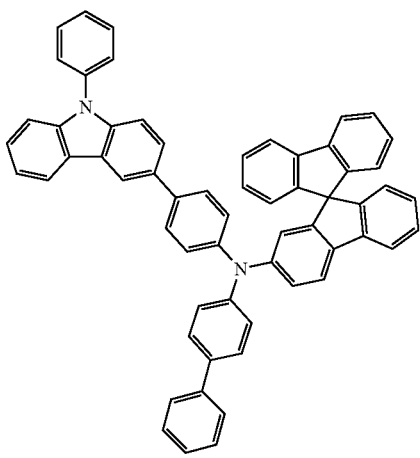 |
| HT9 | HT10 |
| 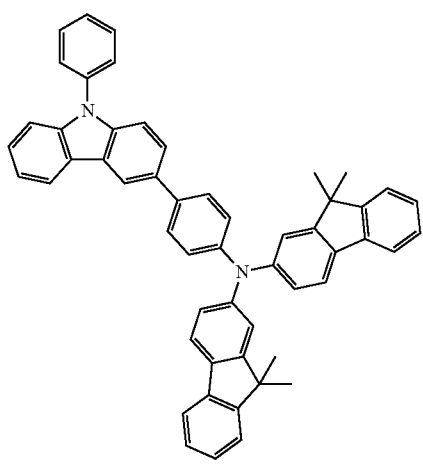 | 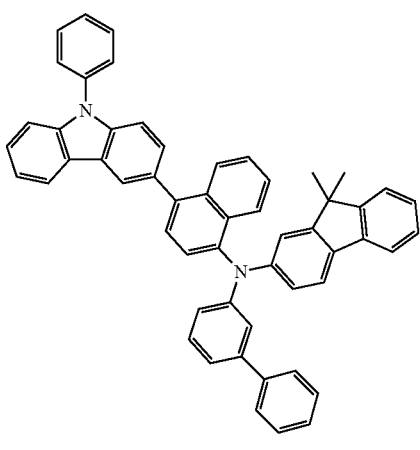 |

-continued
HT11
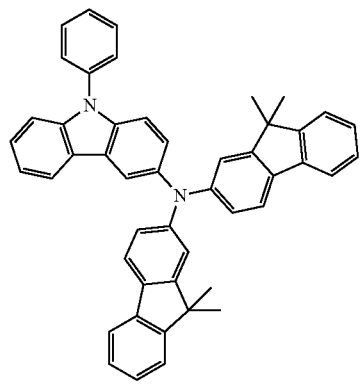
HT12
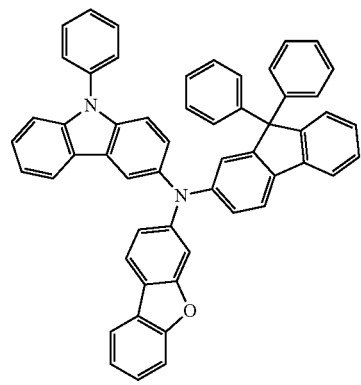
HT13
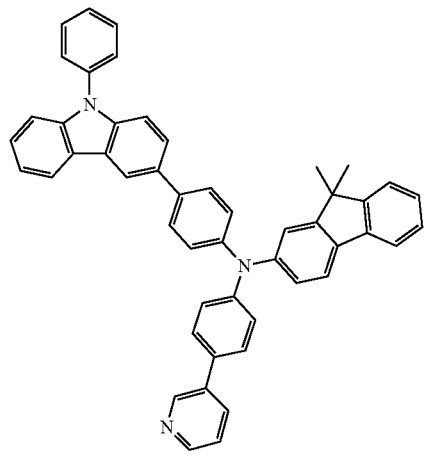
HT14
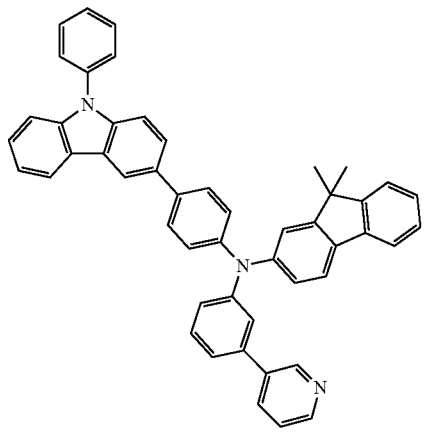
HT15
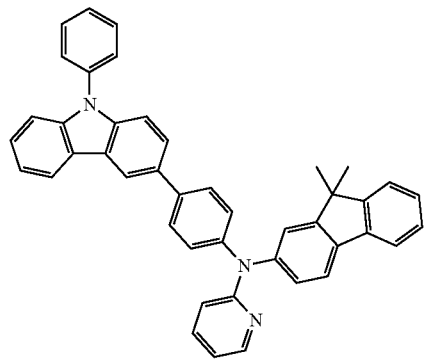
HT16
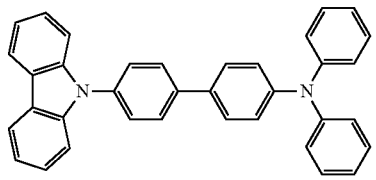
HT17
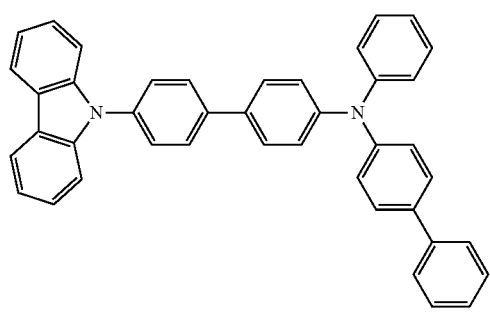
HT18
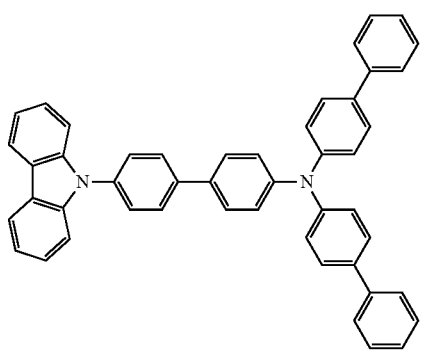

-continued
HT19
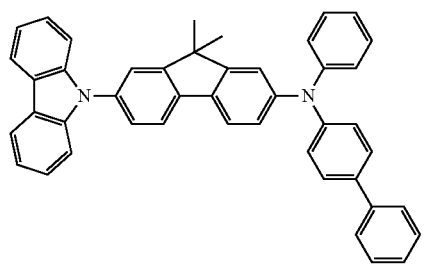
HT20
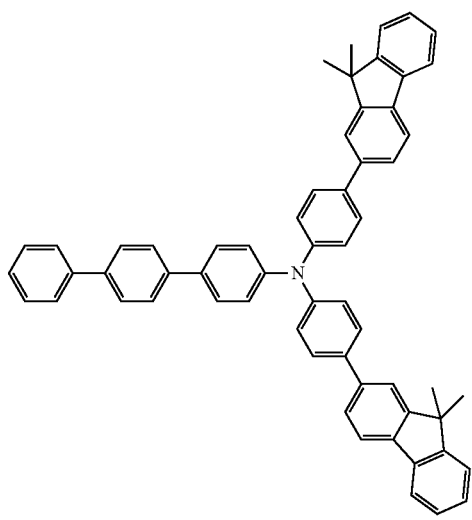
HT21
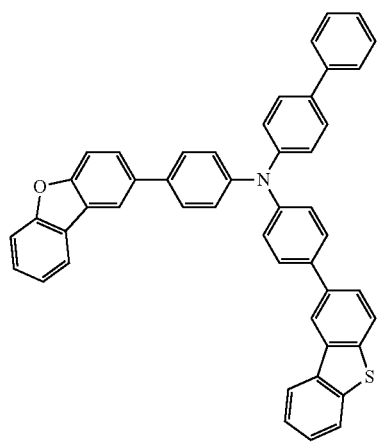
HT22
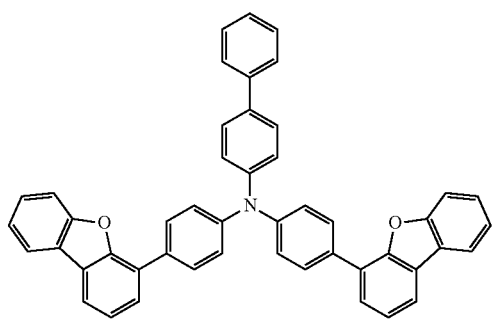
HT23
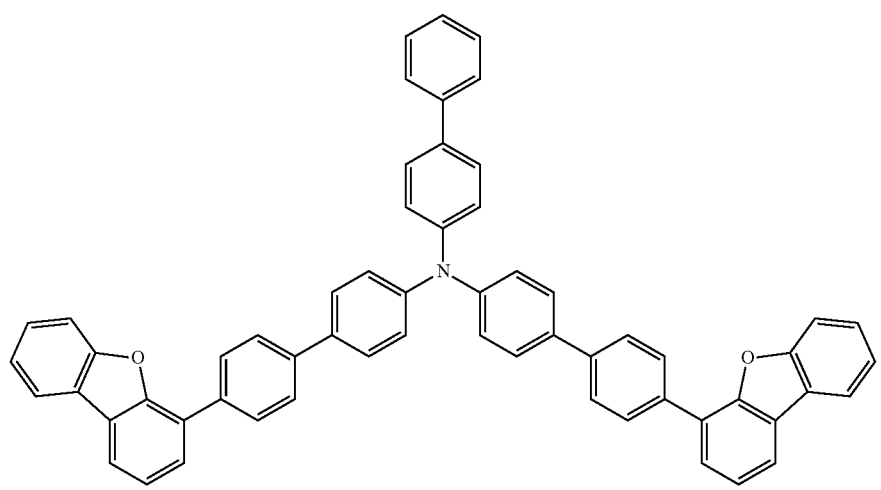

-continued
HT24
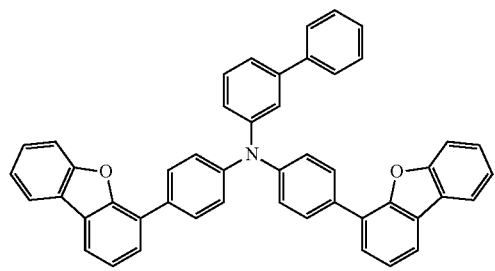
HT25
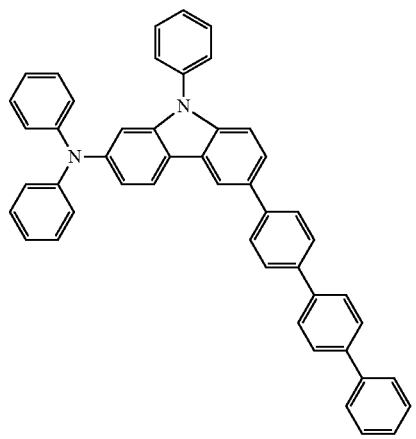
HT26
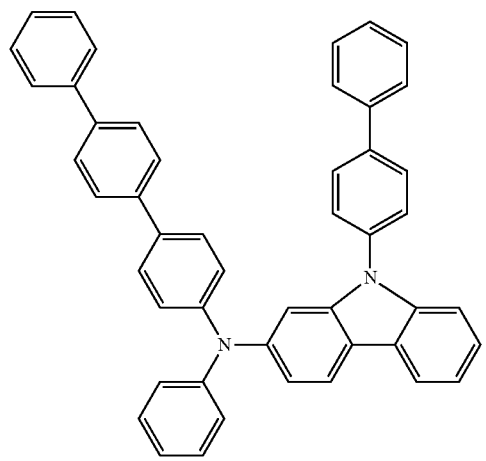
HT27
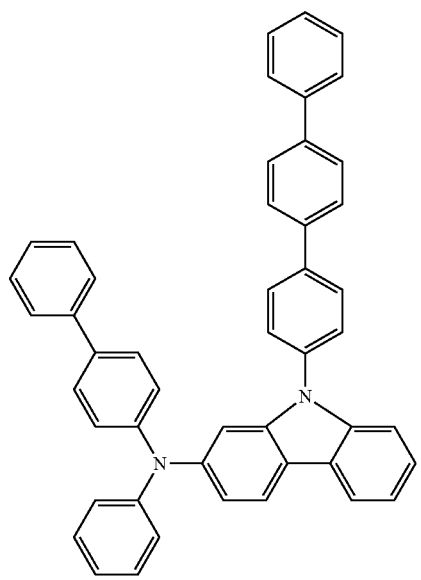
HT28
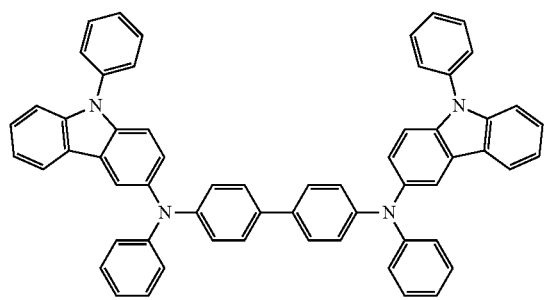
HT29
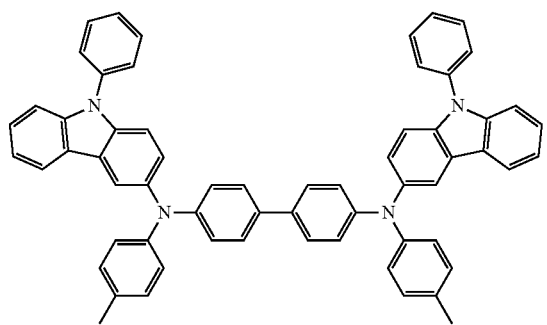

-continued
HT30
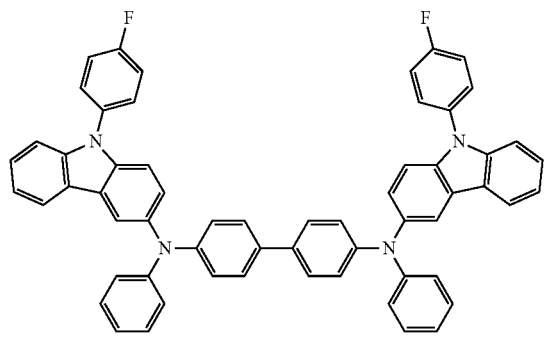
HT31
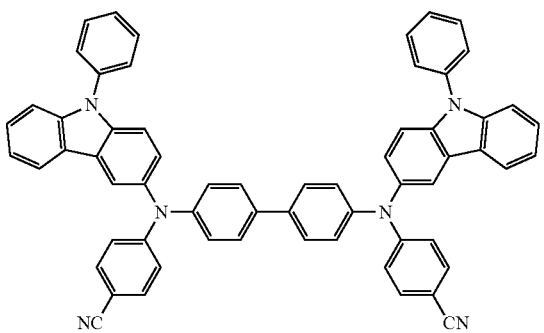
HT32
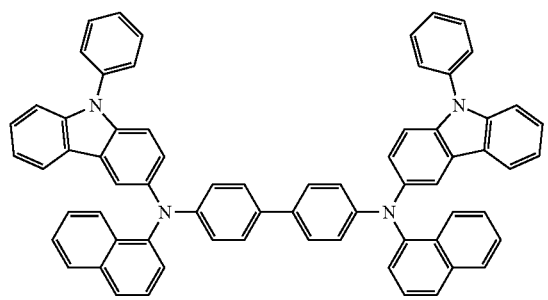
HT33
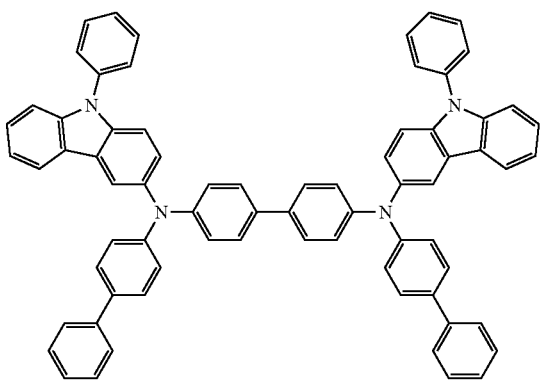
HT34
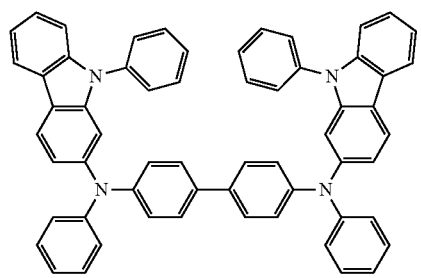
HT35
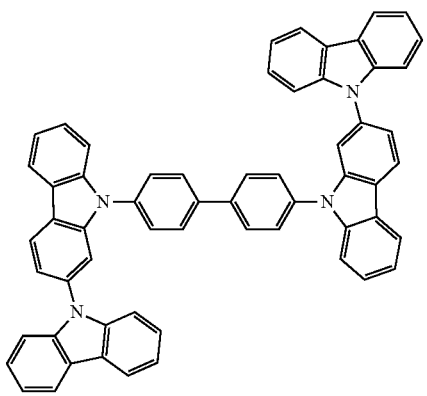
HT36
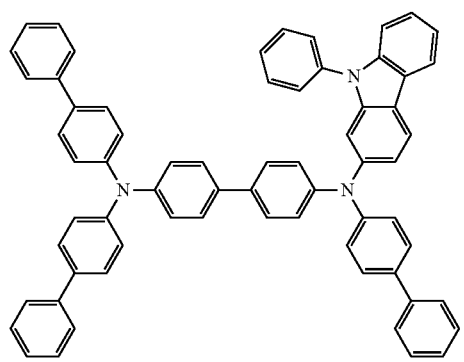
HT37
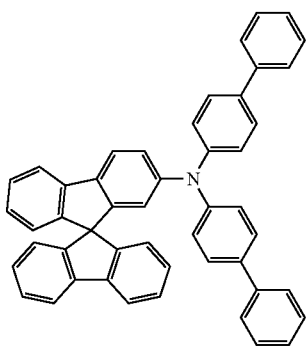

HT38

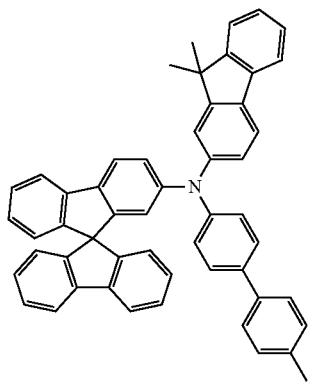

HT39

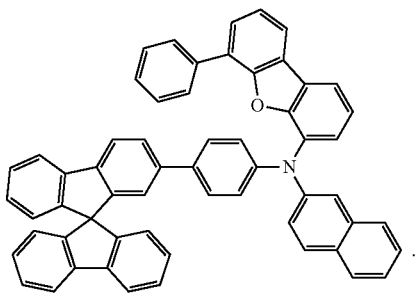

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a LUMO energy level of −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,12-hexaazatriphenylene-hexacarbonitrile (HAT-CN); and a compound represented by Formula 221, but embodiments of the present disclosure are not limited thereto:

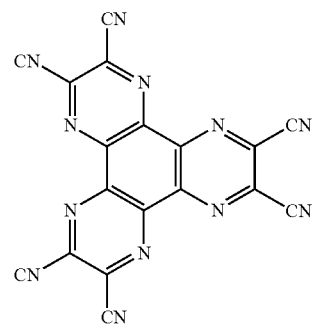

HAT-CN

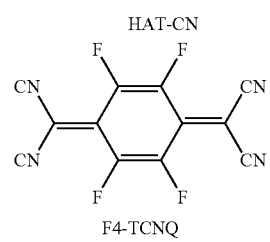

F4-TCNQ

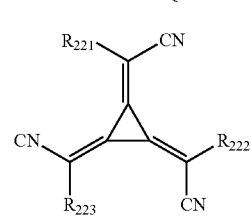

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$alkyl group substituted with —F, a $C_1$-$C_{20}$ alkyl group substituted with —Cl, a $C_1$-$C_{20}$alkyl group substituted with —Br and a $C_1$-$C_{20}$ alkyl group substituted with —I.

Emission Layer in Organic Layer 130

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact (e.g., physically contact) each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may include a compound represented by Formula 301:

$$[Ar_{301}]_{xb11}-[(L_{301})_{xb1}-R_{301}]_{xb21} \qquad \text{Formula 301}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_{301})(Q_{302})(Q_{303})$, —N$(Q_{301})(Q_{302})$, —B$(Q_{301})(Q_{302})$, —C(=O)$(Q_{301})$, —S(=O)$_2(Q_{301})$, and —P(=O)$(Q_{301})(Q_{302})$, xb21 may be an integer from 1 to 5, and $Q_{301}$ to $Q_{303}$ may each independently be selected from a —$C_1C$ alkyl $_{10}$group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si$(Q_{31})(Q_{32})(Q_{33})$, —N$(Q_{31})(Q_{32})$, —B$(Q_{31})(Q_{32})$, —C(=O)$(Q_{31})$, —B(=O)$_2(Q_{31})$, and —P(=O)$(Q_{31})(Q_{32})$, and $Q_{31}$ to $Q_{33}$ may each independently be selected from a —$C_1C$ alkyl $_{10}$group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more $Ar_{301}$(s) may be linked via a single bond.

In one or more embodiments the compound represented by Formula 301 may be represented by Formula 301-1 or 301-2:

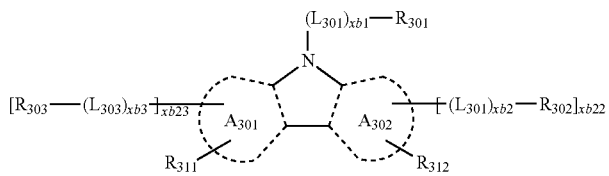

Formula 301-1

-continued

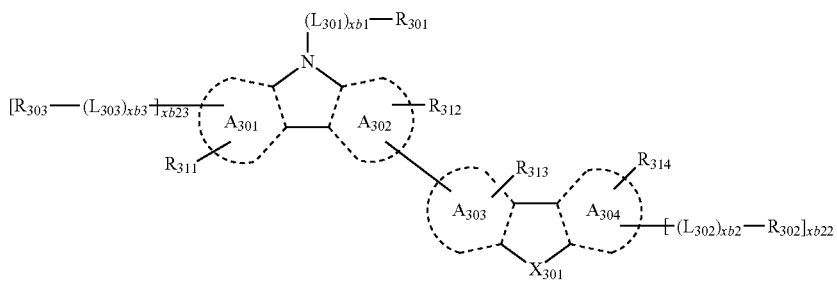

Formula 301-2

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[$(L_{304})_{xb4}$-$R_{304}$], $R_{311}$ to $R_{314}$ each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ are the same as described above, $L_{302}$ to $L_{304}$ may each independently be the same as defined in connection with $L_{301}$, xb2 to xb4 may each independently be the same as defined in connection with xb1, and $R_{302}$ to $R_{304}$ may each independently be the same as defined in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are the same as described above.

In one embodiment, in Formulae 301, 301-1, and 301-2, 8301 to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

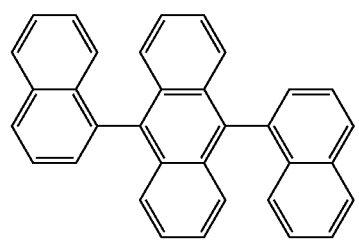

H1

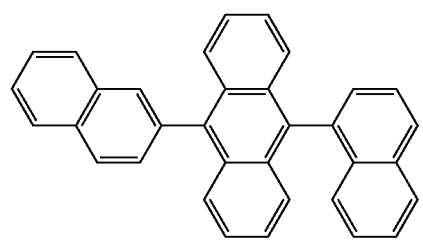

H2

H3
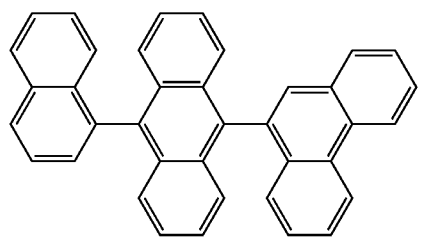
H4
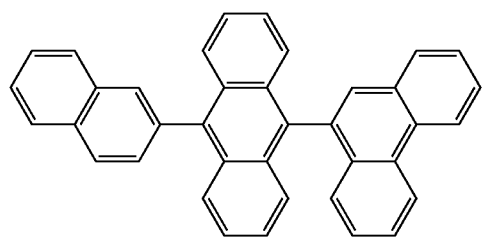
H5
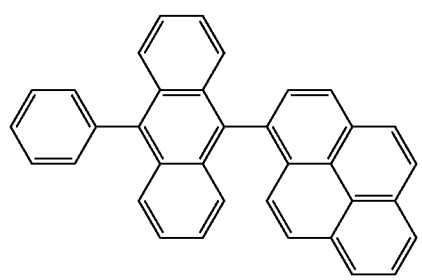
H6
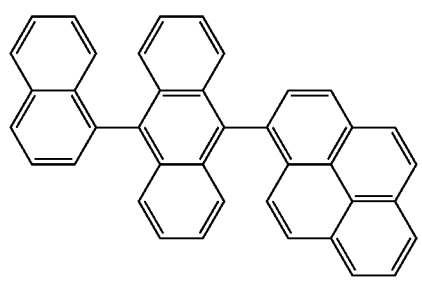
H7
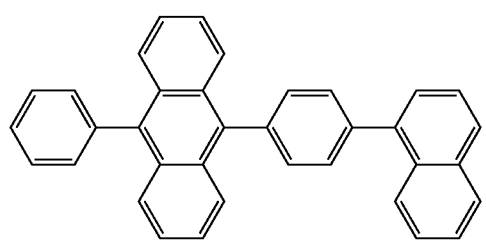
H8
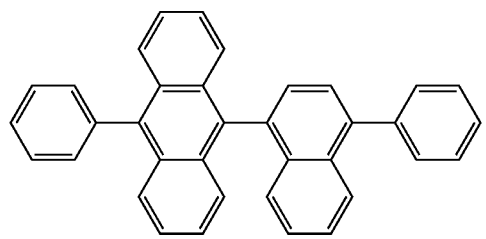
H9
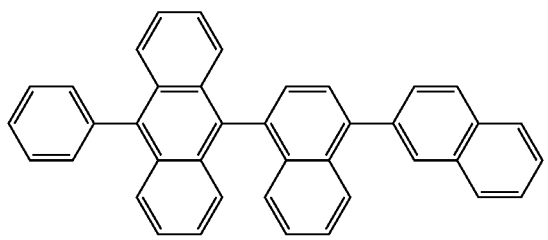
H10
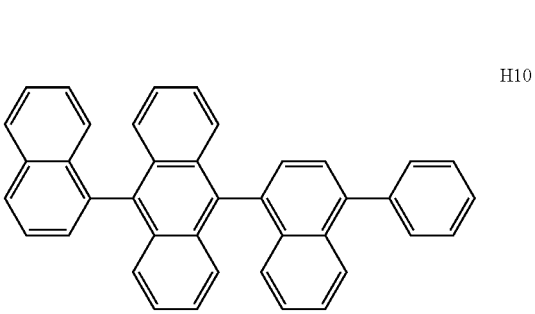
H11
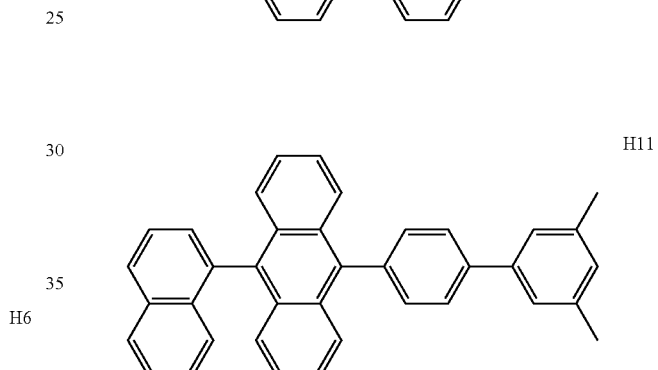
H12
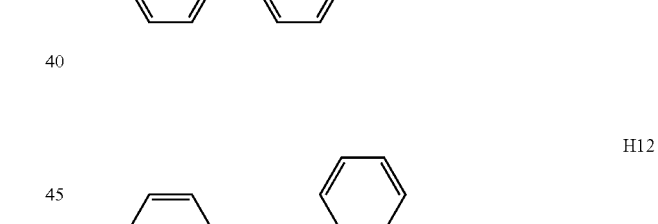
H13
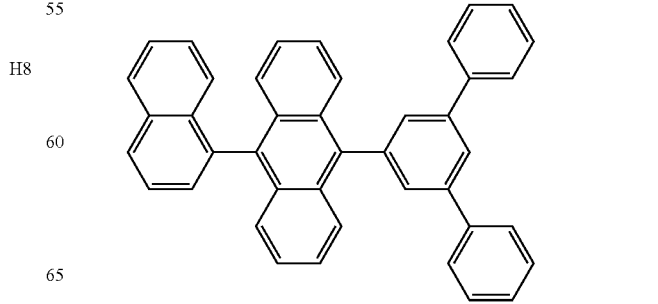

H14
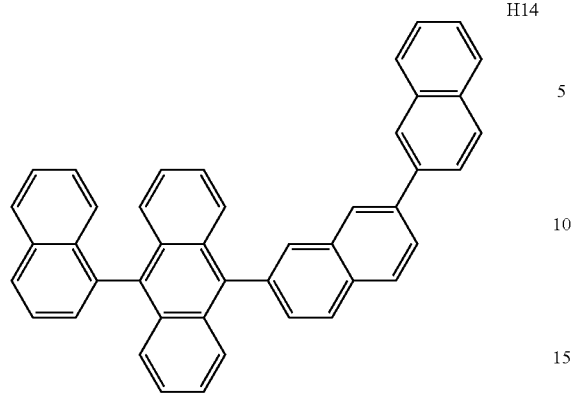
H15
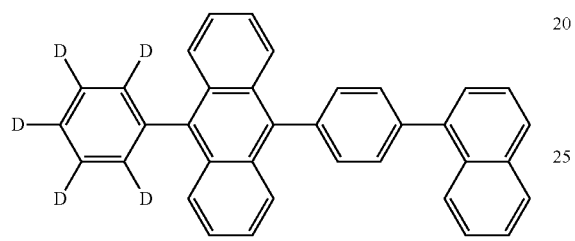
H16
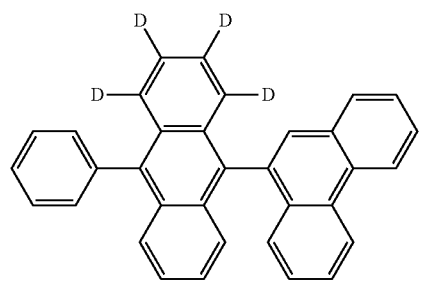
H17
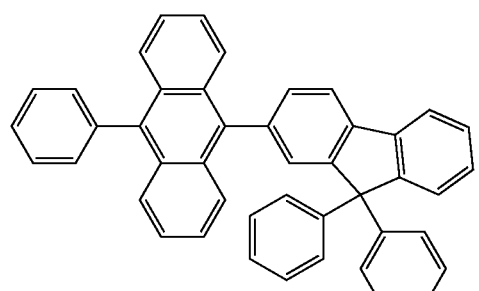
H18
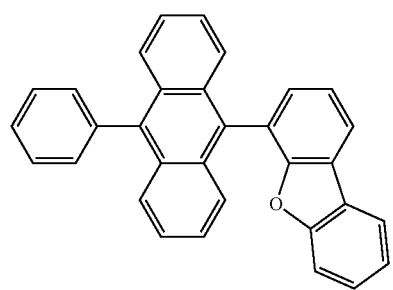
H19
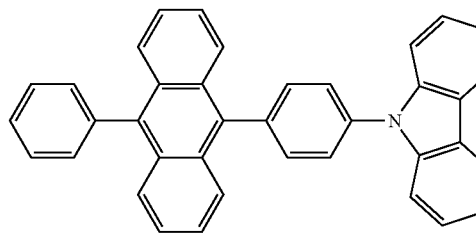
H20
H21
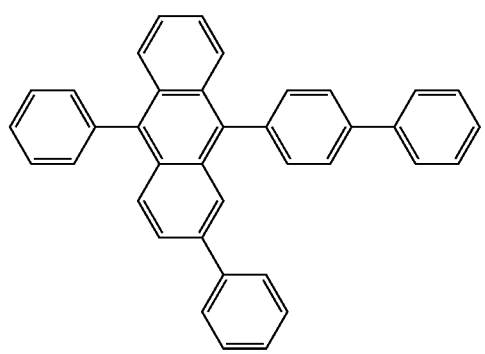
H22

H23
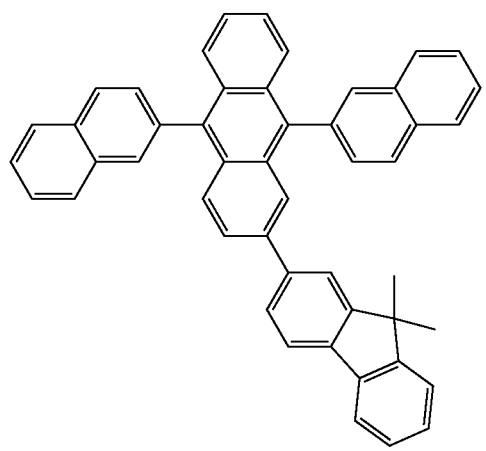
H24
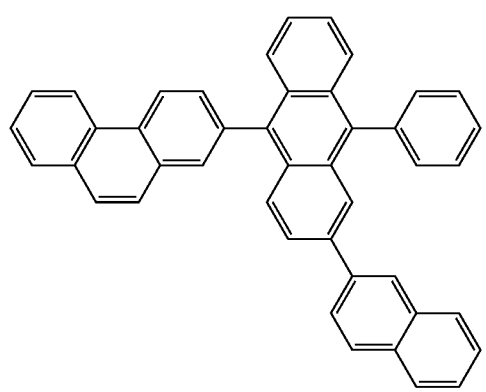
H25
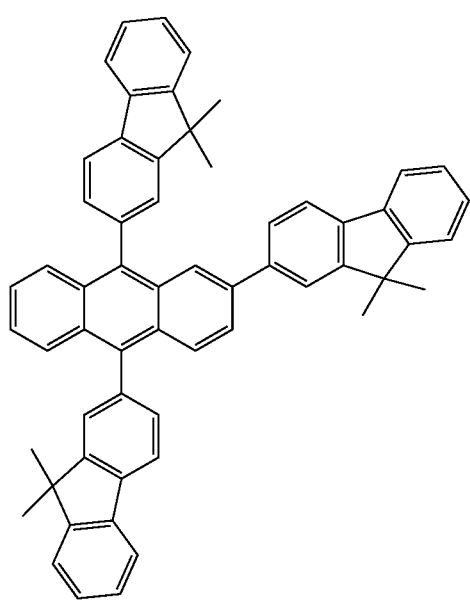
H26
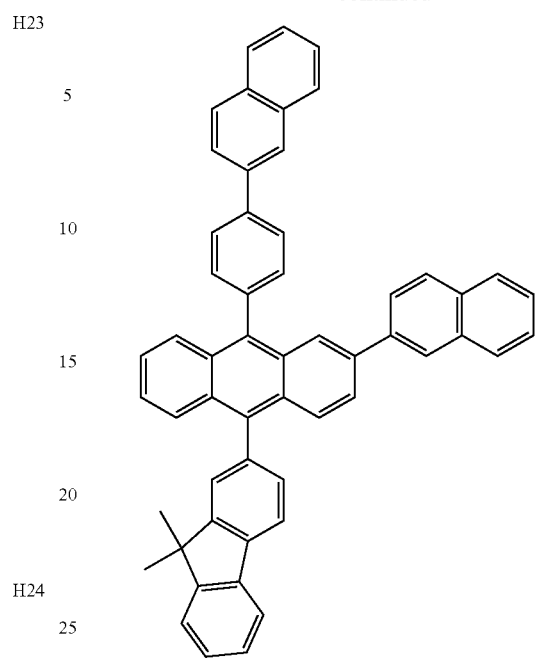
H27
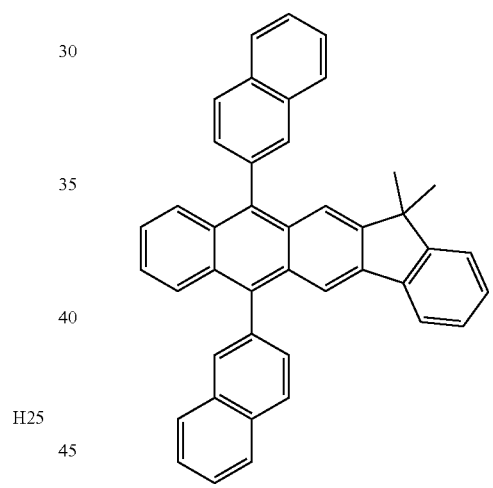
H28
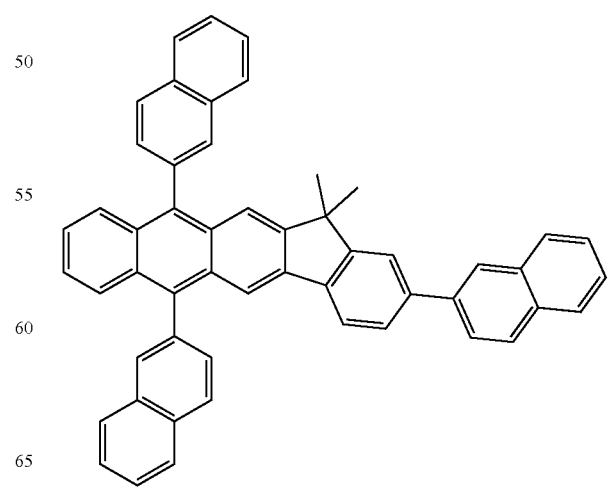

-continued
H29
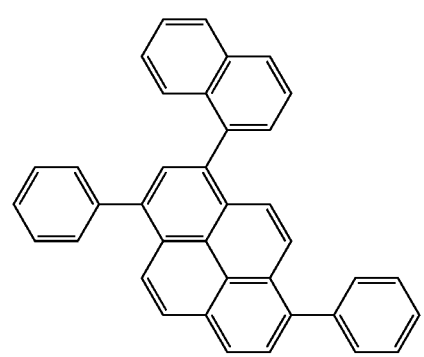
H30
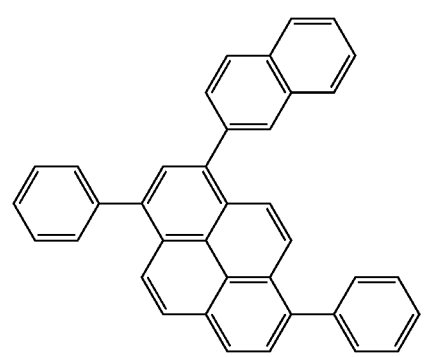
H31
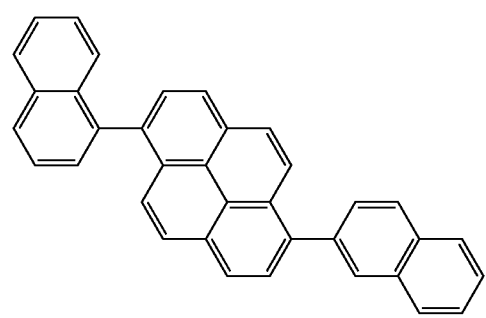
H32
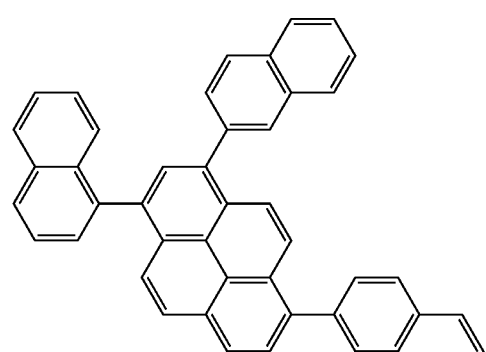
H33
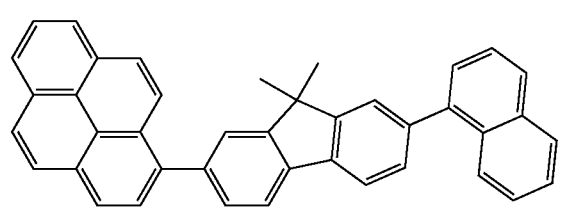
-continued
H34
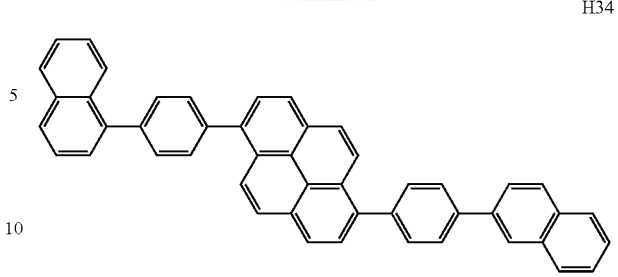
H35
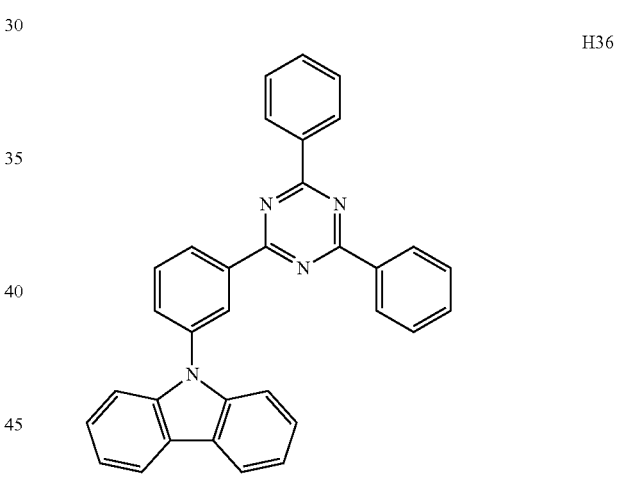
H36
H37
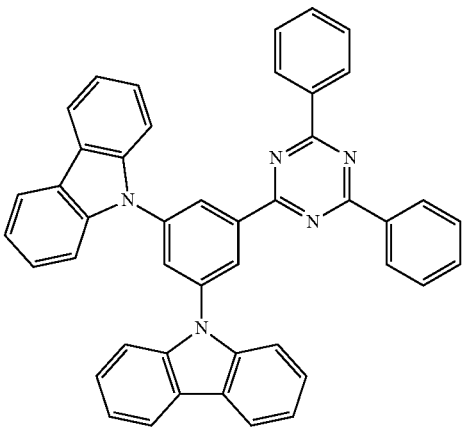

-continued
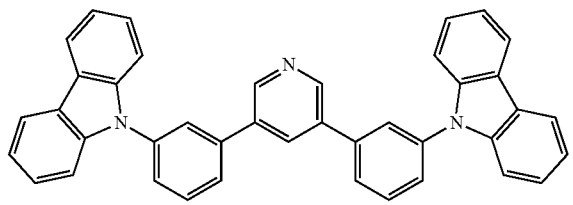
H38
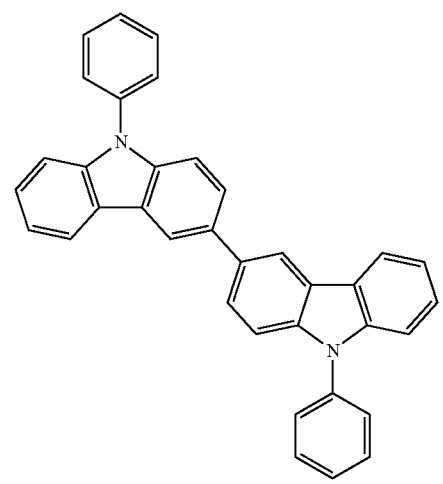
H39
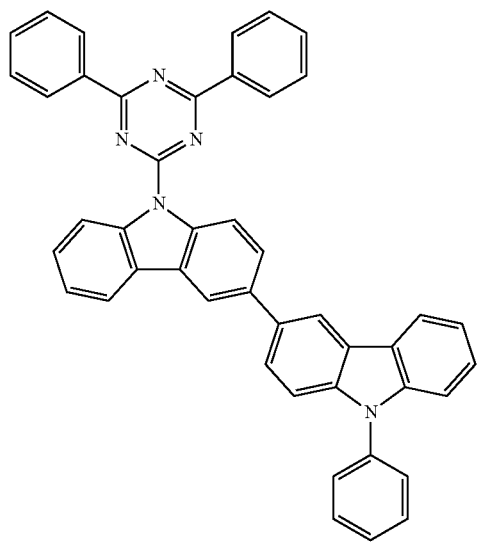
H40
-continued
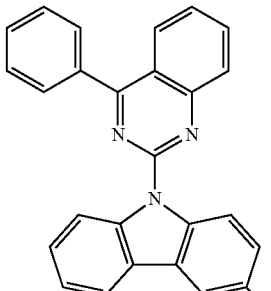
H41
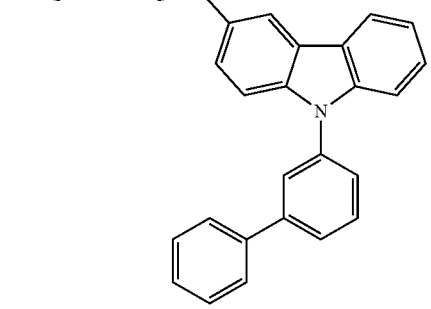
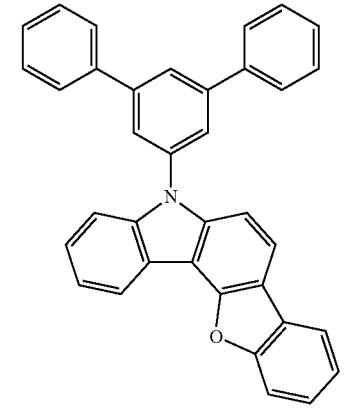
H42
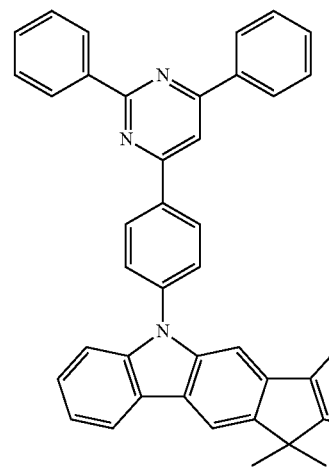
H43

-continued
H44
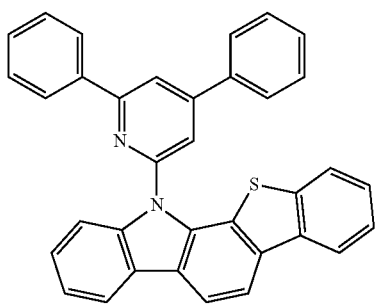
H45
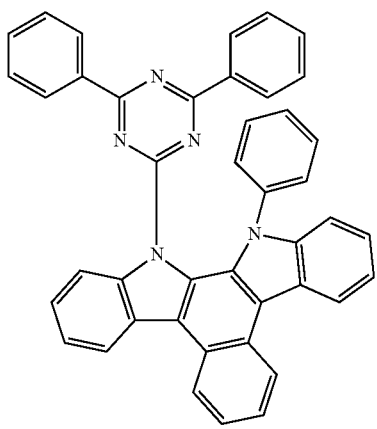
H46
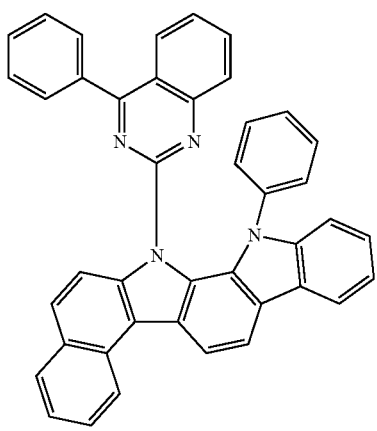
H47
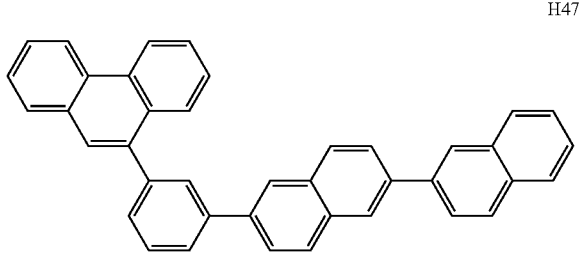
H48
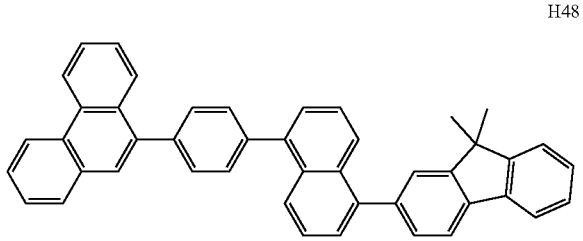
-continued
H49
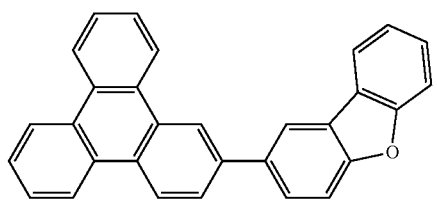
H50
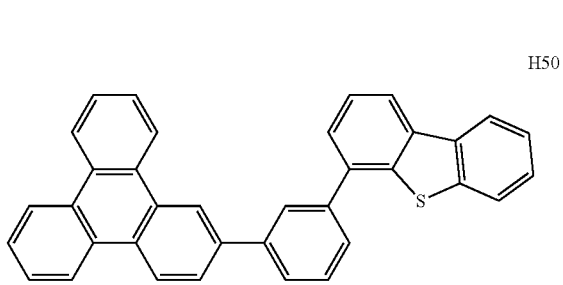
H51
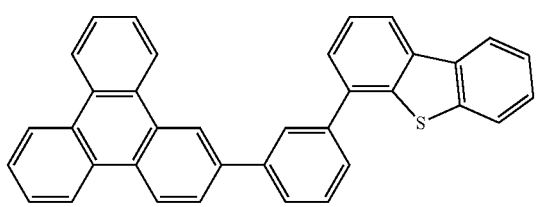
H52
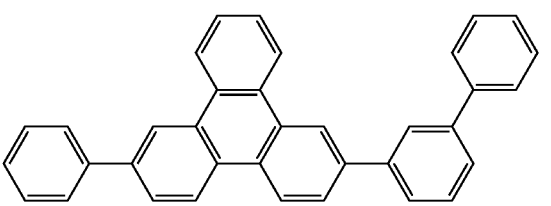
H53
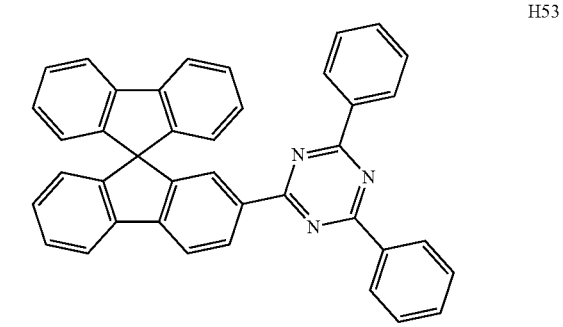

-continued

H54

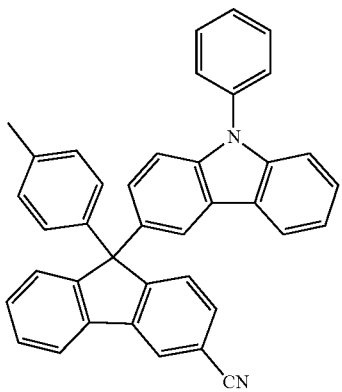

H55

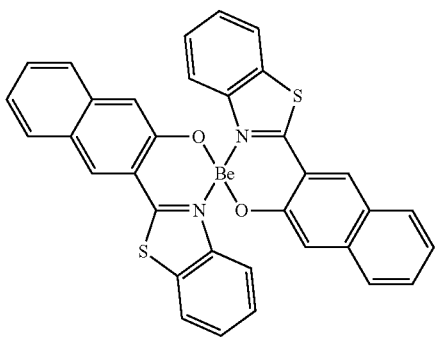

Phosphorescent Dopant Included in Emission Layer in Organic Layer 130

The phosphorescent dopant may include an organometallic complex represented by Formula 401:

$$M(L_{401})_{xc1}(L_{402})_{xc2}$$ Formula 401

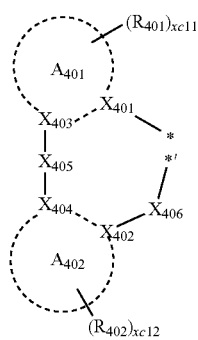

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—C(=O)—*', *—N(Q_{411})—*', *—C(Q_{411})(Q_{412})—*', *—C(Q_{411})=C(Q_{412})—*', *—C(Q_{411})=*', or *=C=*', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a —$C_1$C alkyl $_{10}$ group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen concurrently (e.g., at the same time).

In one or more embodiments, $R_{401}$ and $R_{402}$ in Formula 401 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantly group, a norbornanyl group, and a norbornenyl group;

a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantly group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a —$C_1$C alkyl $_{10}$group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is two or more, two $A_{401}$(s) in two or more $L_{401}$ (S) may optionally be linked via $X_{407}$, which is a linking group, or two $A_{402}$(s) in two or more $L_{401}$ (S) may optionally be linked via $X_{408}$, which is a linking group (see Compounds PD1 to PD4 and PD7). $X_{407}$ and $X_{408}$ may each independently be a single bond, *—N($Q_{413}$)—*', *—C($Q_{413}$)($Q_{414}$)—*', or *—C($Q_{413}$)=C($Q_{414}$)—*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

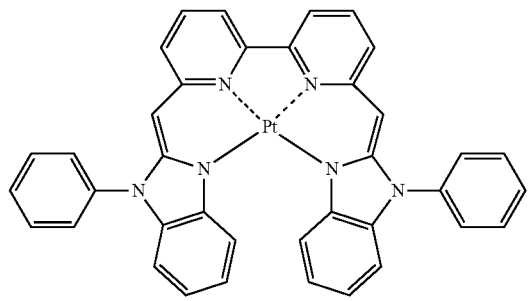

PD1

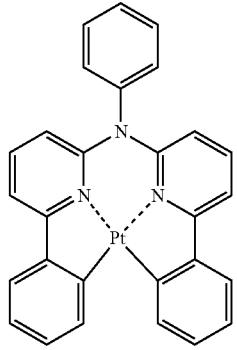

PD2

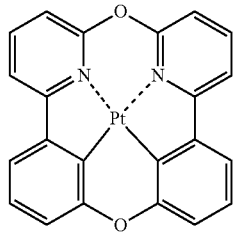

PD3

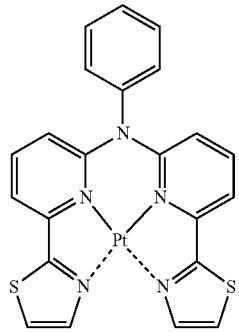

PD4

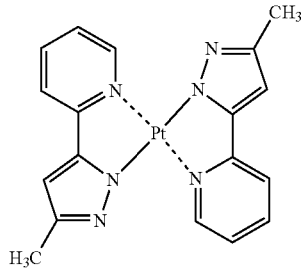

PD5

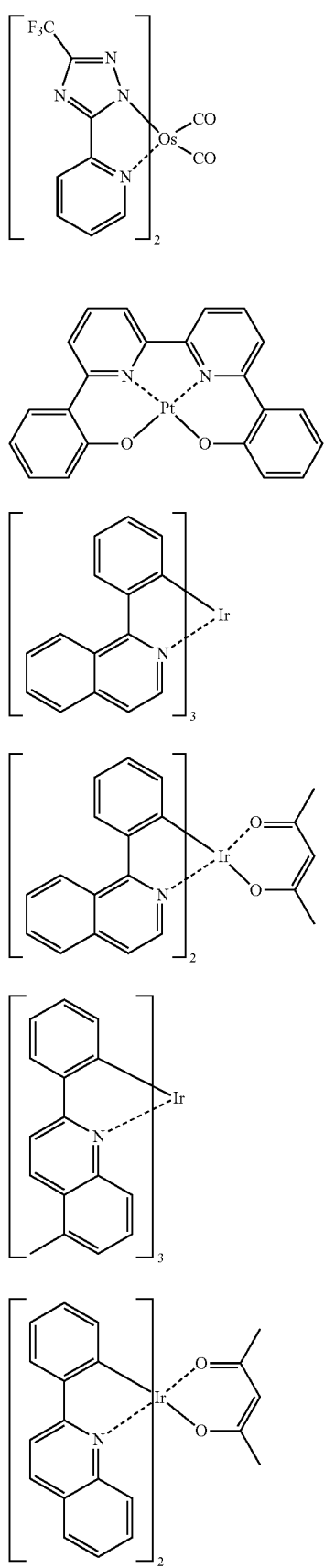

PD17 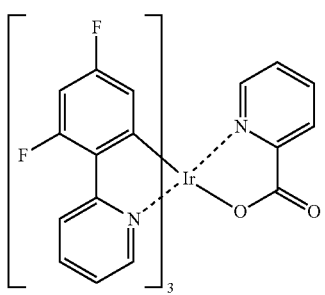
PD18 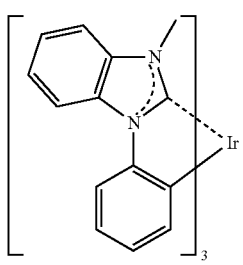
PD19 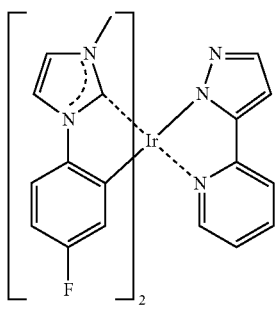
PD20 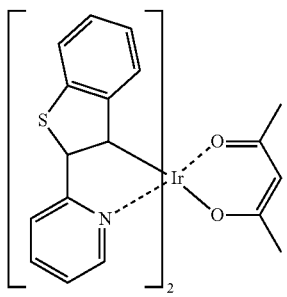
PD21 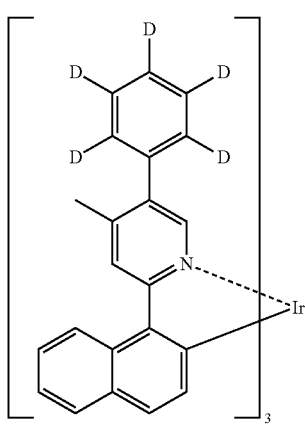
PD22 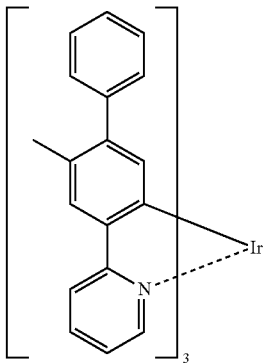
PD23 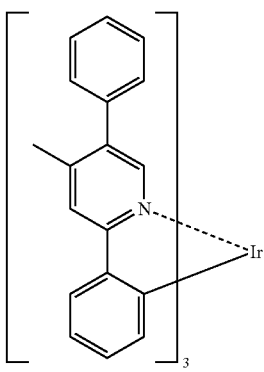
PD24 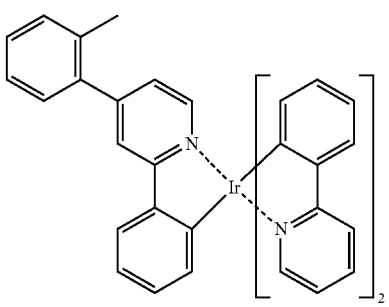
PD25 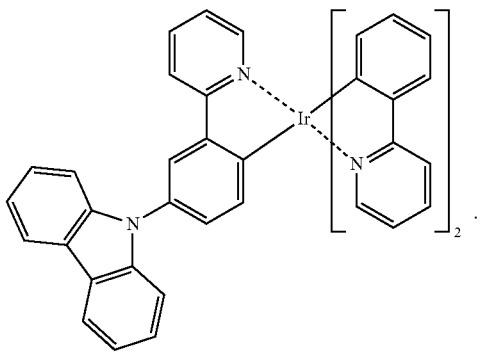
Fluorescent Dopant in Emission Layer
In addition, the fluorescent dopant may include an arylamine compound or a styrylamine compound.
In addition, the fluorescent dopant may include a compound represented by Formula 501:

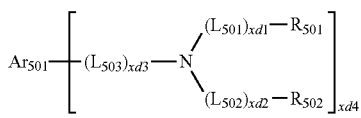

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_6$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, $Ar_{601}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

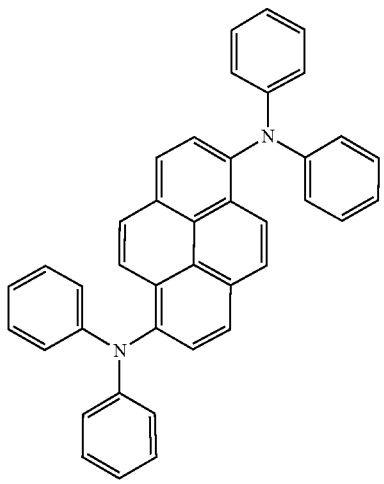

FD1

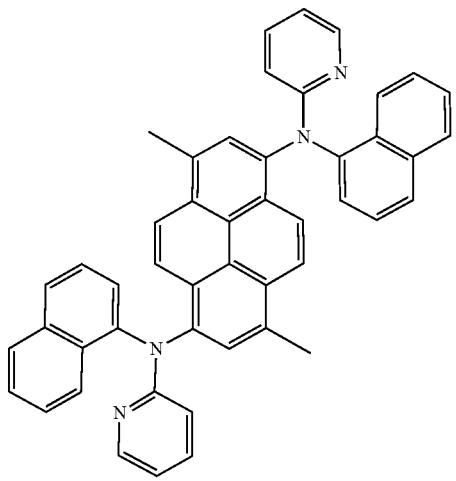

FD2

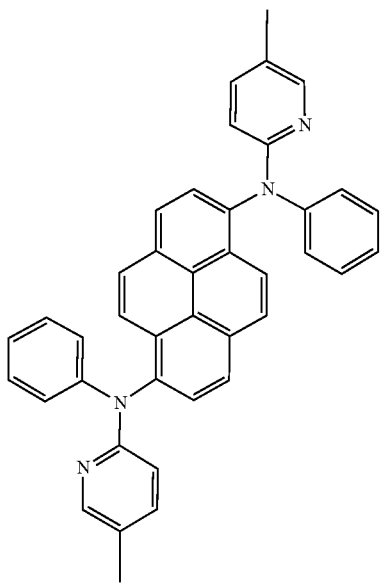

FD3

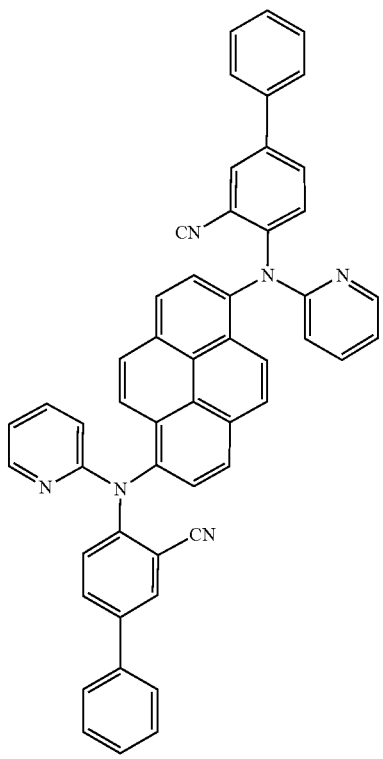

FD4

-continued
FD5
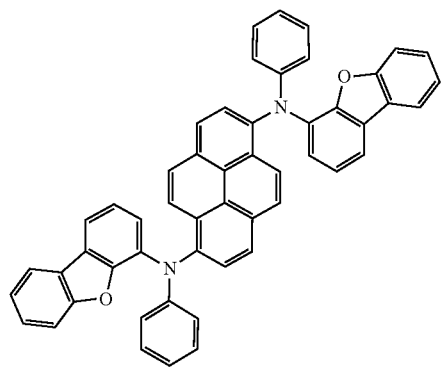
FD6
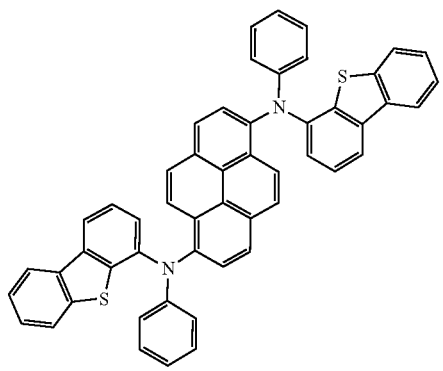
FD7
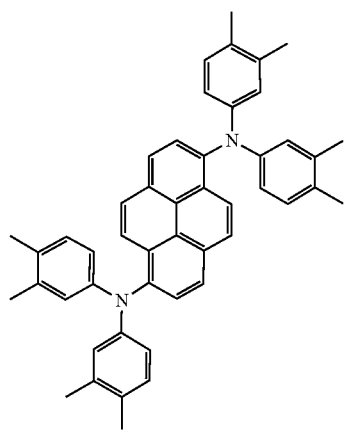
FD8
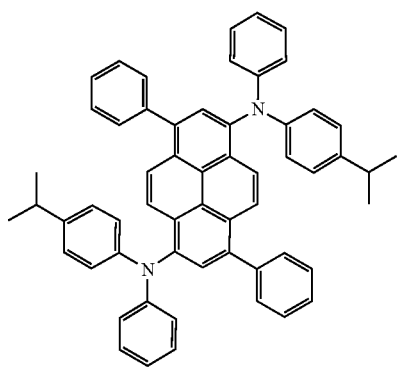
FD9
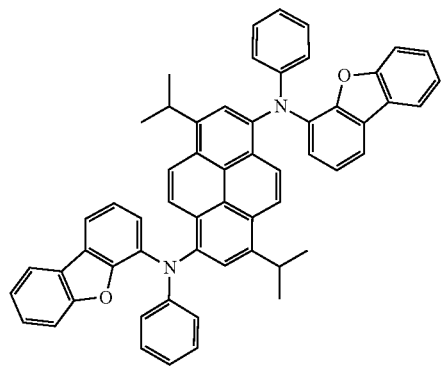
FD10
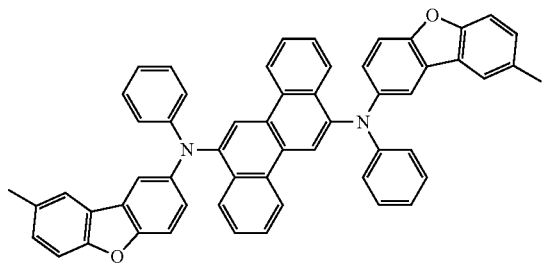
FD11
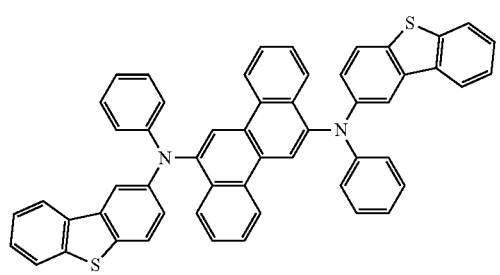
FD12
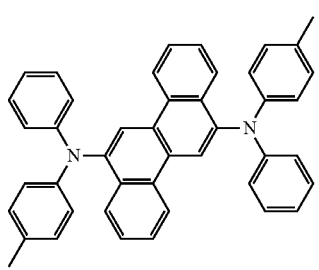

-continued
FD13
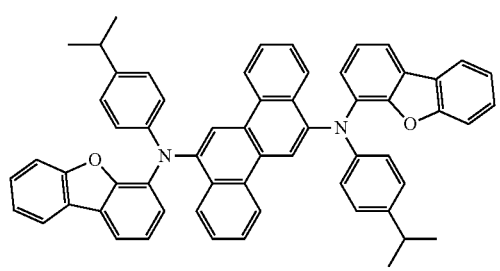
FD14
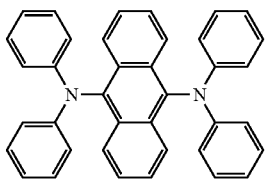
FD15
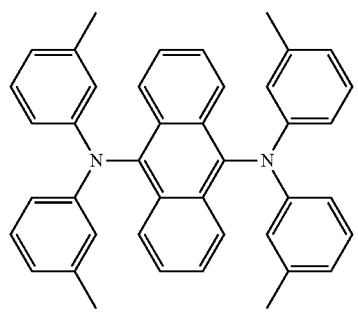
FD16
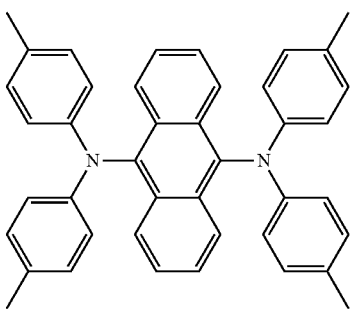
FD17
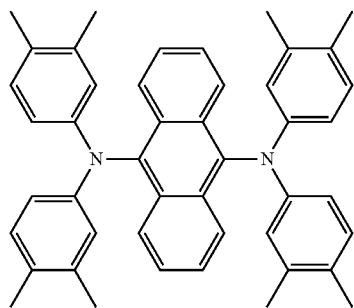
FD18
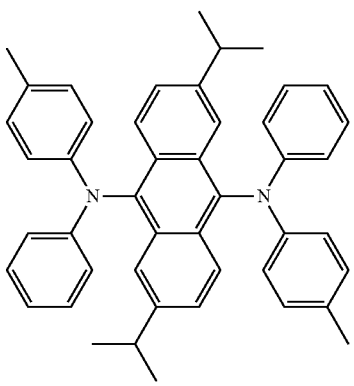
FD19
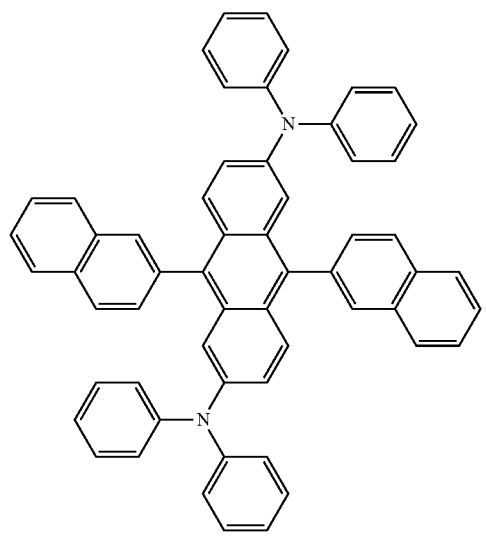
FD20
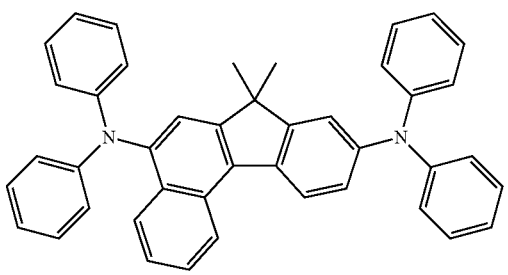

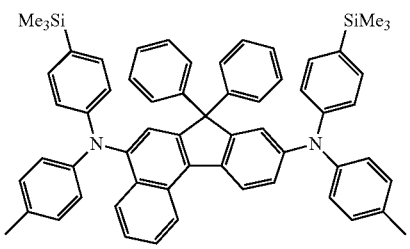
FD21
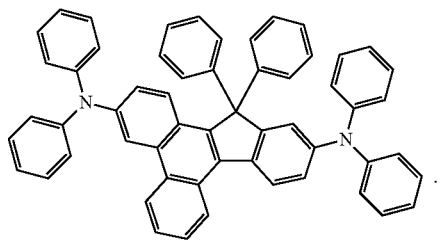
FD22
In one or more embodiments, the fluorescent dopant may be selected from the following compounds, but embodiments of the present disclosure are not limited thereto:
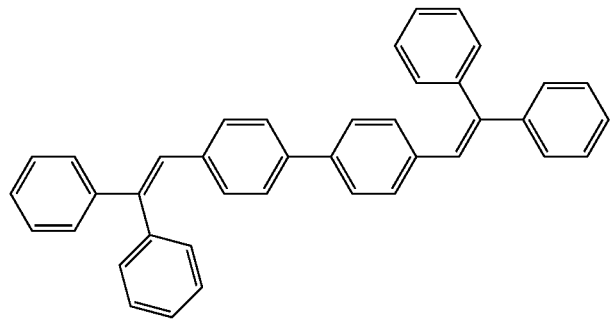
DPVBi
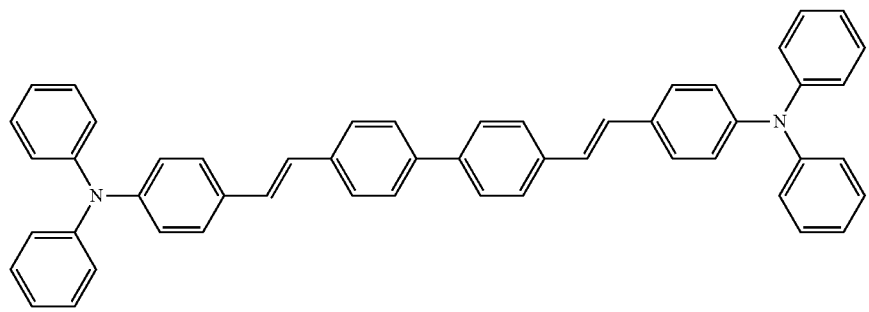
DPAVBi
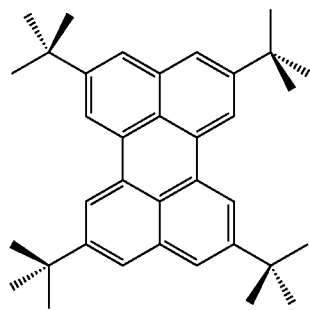
TBPe
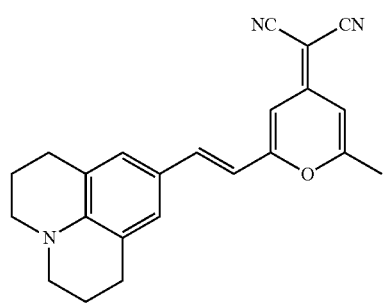
DCM

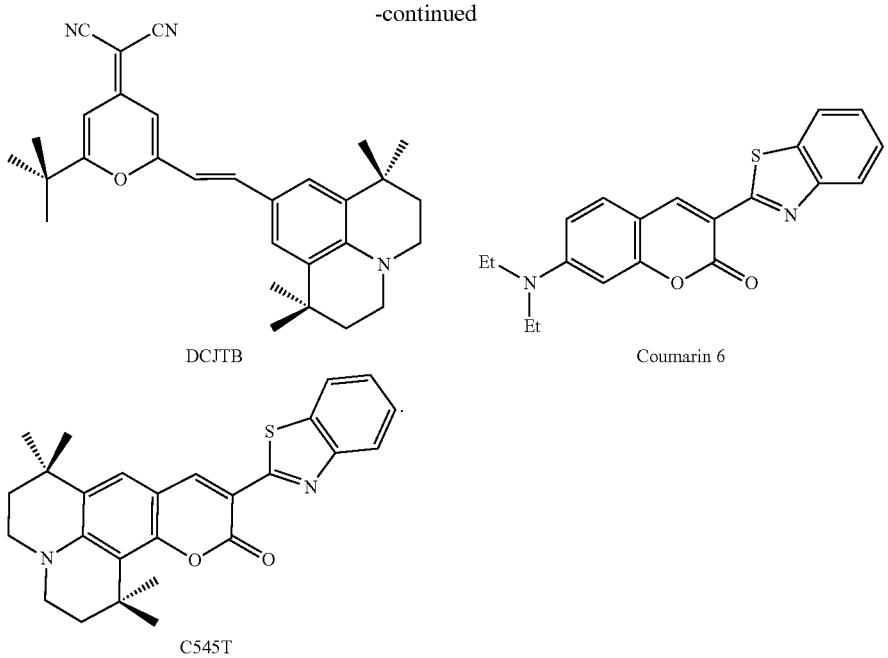

DCJTB

Coumarin 6

C545T

Electron Transport Region in Organic Layer 130

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring," as used herein, indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other (e.g., combined together), or iii) a heteropolycyclic group in which at least one of 5-membered to 7-membered heteromonocyclic groups, each having at least one *—N=*' moiety, is condensed with (e.g., combined with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, a thiadiazole, an imidazopyridine, an imidazopyrimidine, and an azacarbazole, but are not limited thereto.

For example, the electron transport region may include a compound represented by Formula 601:

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(═O) ($Q_{601}$), —S(═O)$_2$($Q_{601}$), and —P(═O)($Q_{601}$)($Q_{602}$), $Q_{601}$ to $Q_{603}$ may each independently be a —$C_1C$ alkyl $_{10}$ group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(s) in the number of xe11 and $R_{601}$(s) in the number of xe21 may include the π electron-depleted nitrogen-containing ring.

In one embodiment, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazinegroup, a benzimidazole group, an isobenzothiazole group, a benzoxazole group, an isobenzoxazole group, a triazole group, a tetrazole group, an oxadiazole group, a triazine group, a thiadiazolegroup, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazinegroup, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), and —P(═O)($Q_{31}$)($Q_{32}$), and $Q_{31}$ to $Q_{33}$ may each independently be selected from a —$C_1C$ alkyl $_{10}$group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, the compound represented by Formula 601 may be represented by Formula 601-1:

Formula 601-1

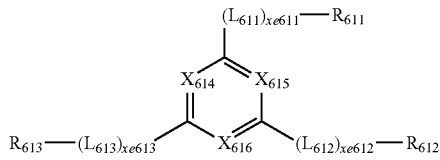

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be the same as defined in connection with $L_{601}$, xe611 to xe613 may each independently be the same as defined in connection with xe1, $R_{611}$ to $R_{613}$ may each independently be the same as defined in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, 8601 and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ are the same as described above.

The electron transport region may include at least one compound selected from Compounds ET1 to ET36, but embodiments of the present disclosure are not limited thereto:

ET1

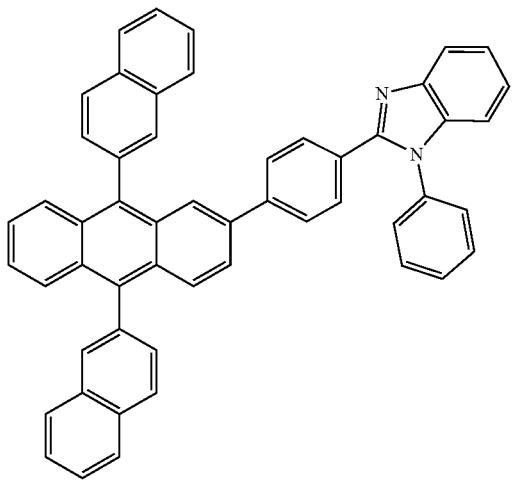

ET2

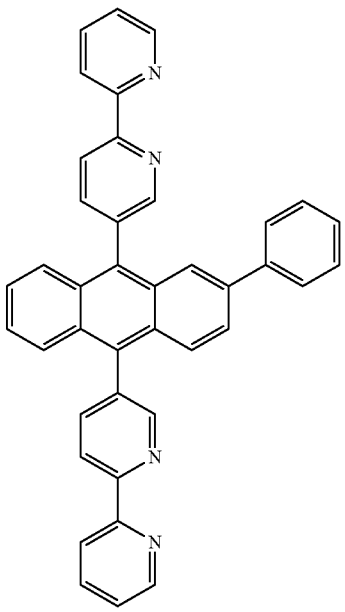

ET3

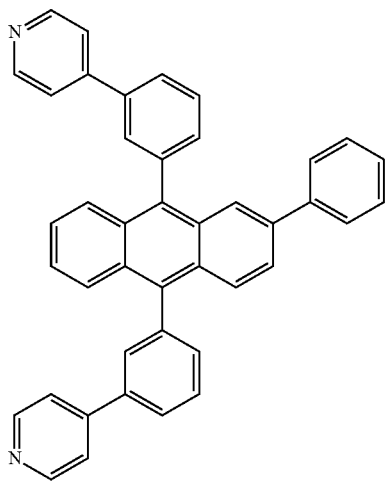

ET4

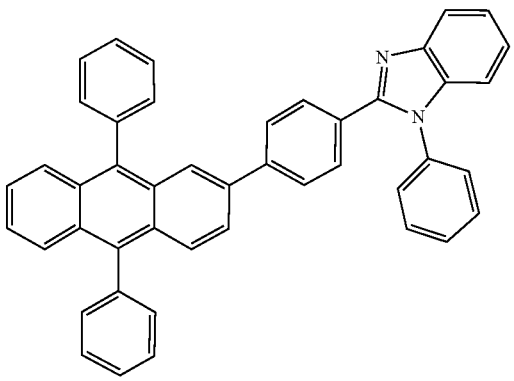

ET5

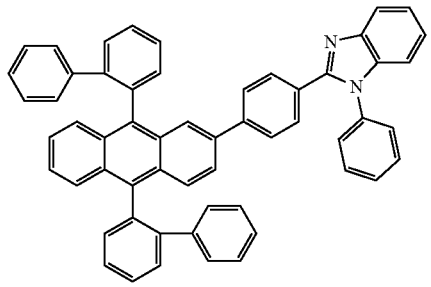

ET6

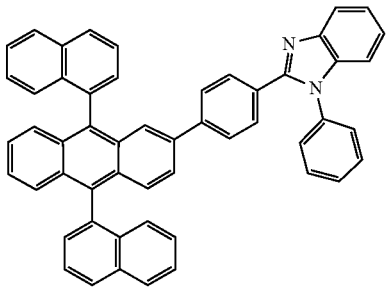

-continued
ET7
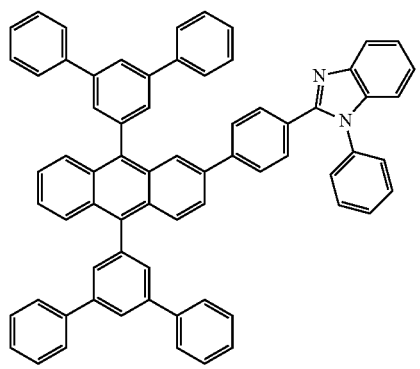
ET8
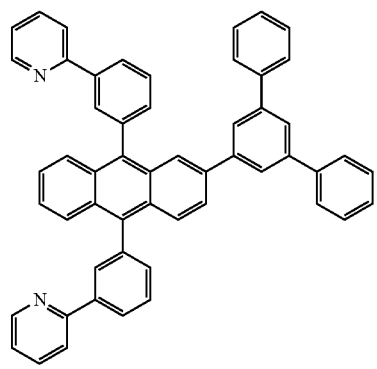
ET9
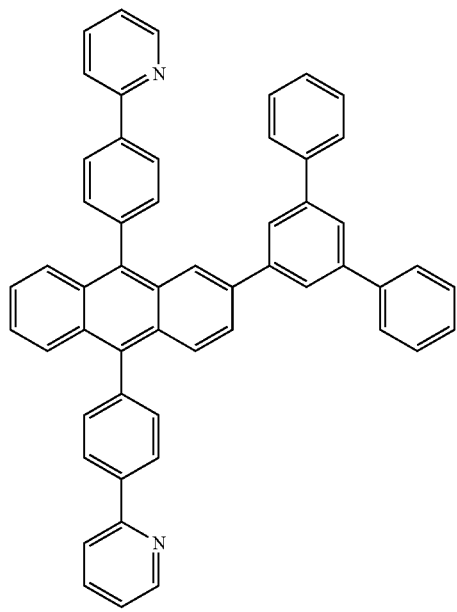
ET10
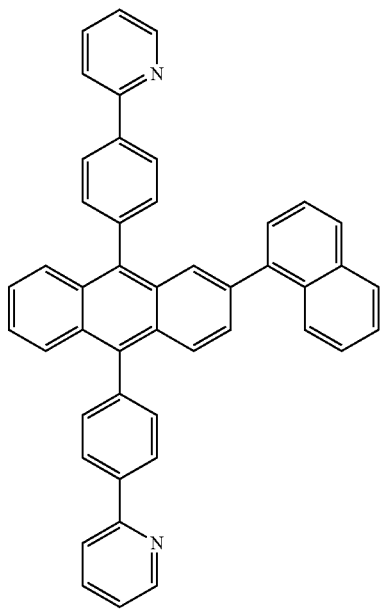
ET11
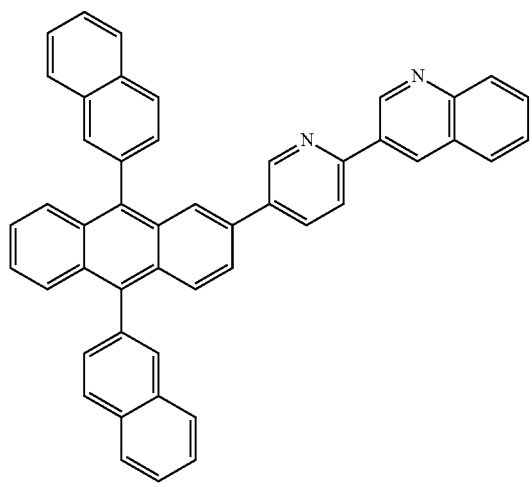
ET12
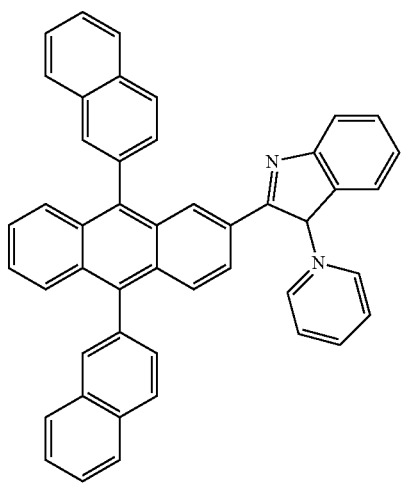

-continued
| ET13 | ET14 |
|---|---|
| 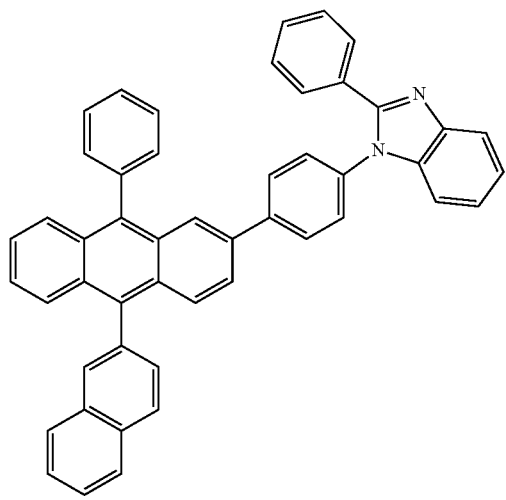 | 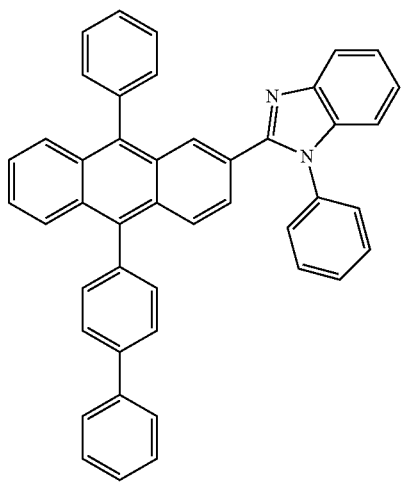 |
| ET15 | ET16 |
| 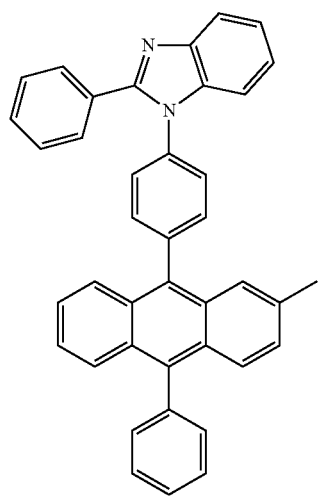 | 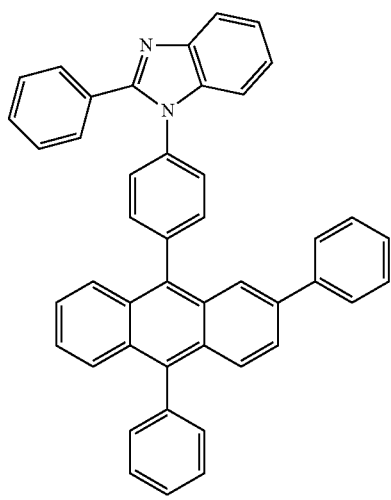 |
| ET17 | ET18 |
| 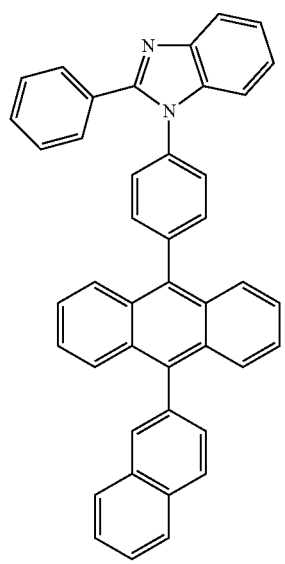 | 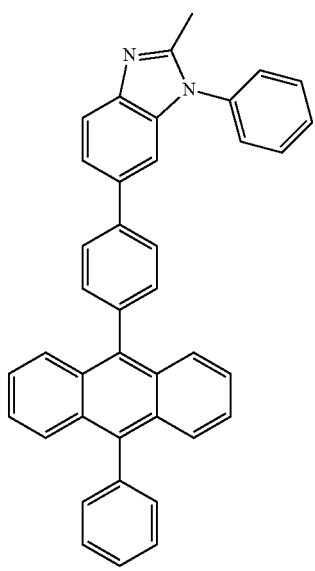 |

-continued
ET19
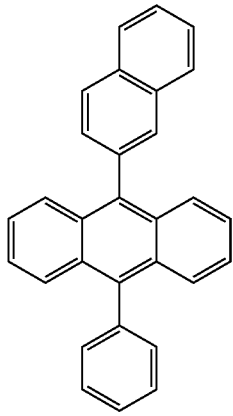
ET20
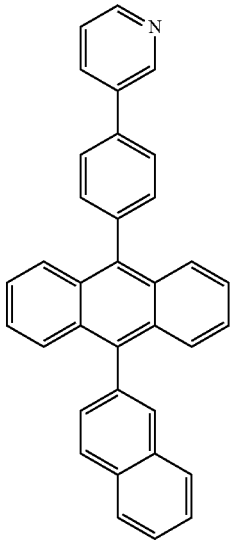
ET21
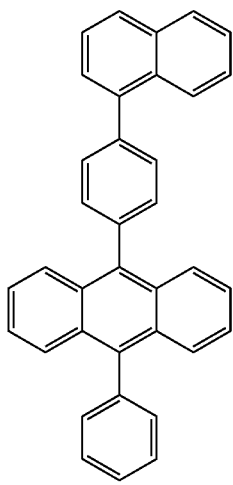
ET22
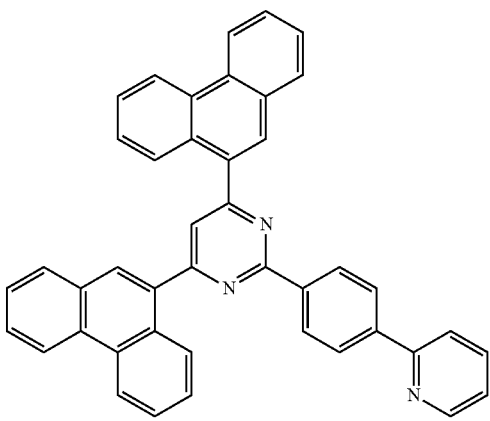
ET23
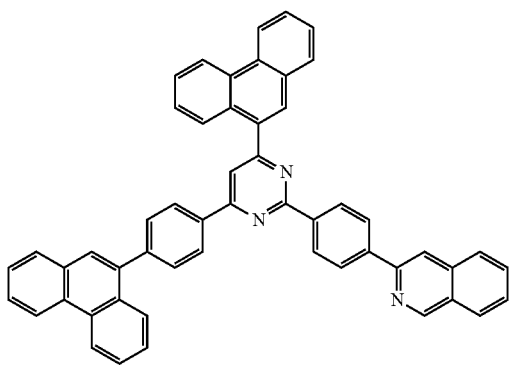
ET24
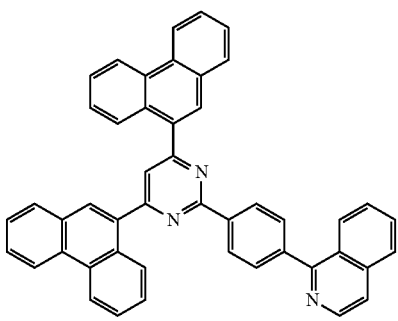

-continued
ET25
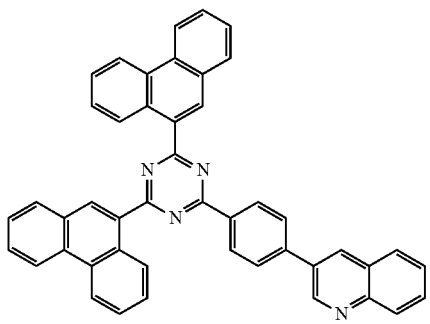
ET26
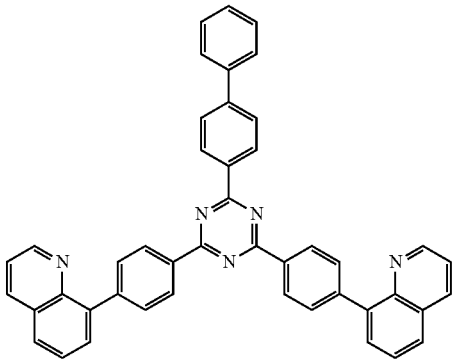
ET27
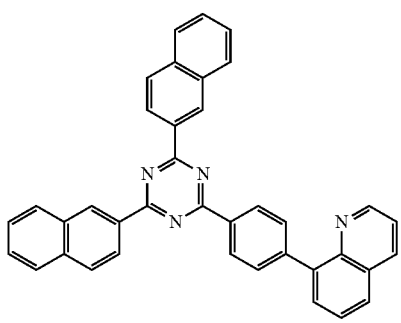
ET28
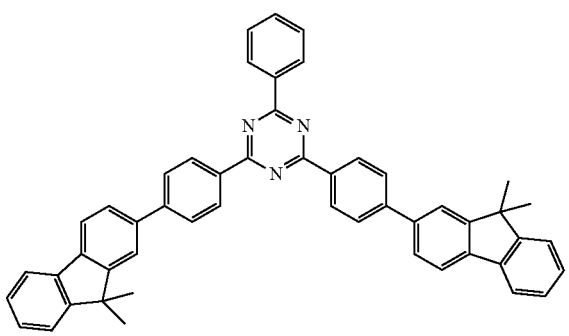
ET29
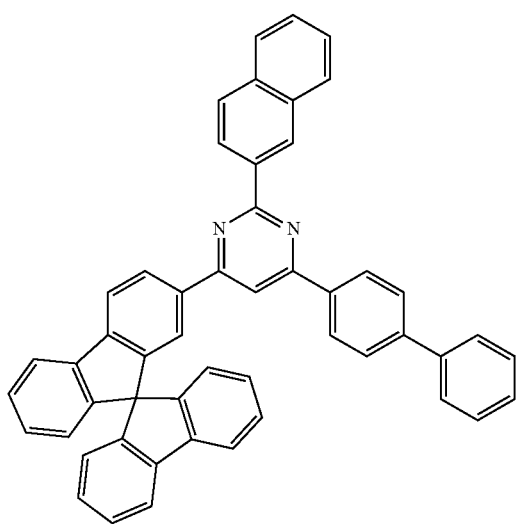
ET30
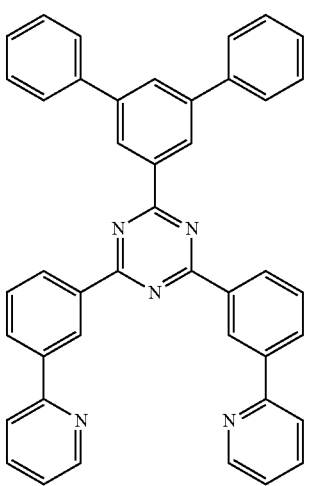

-continued
ET31
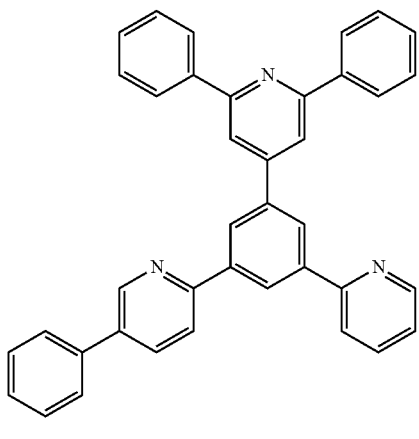
ET32
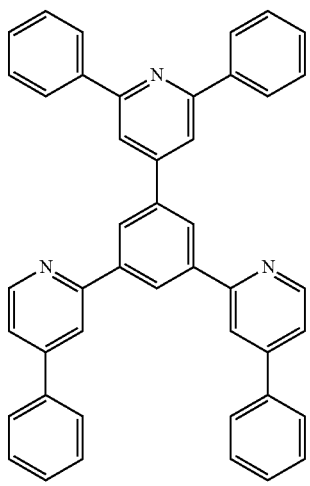
ET33
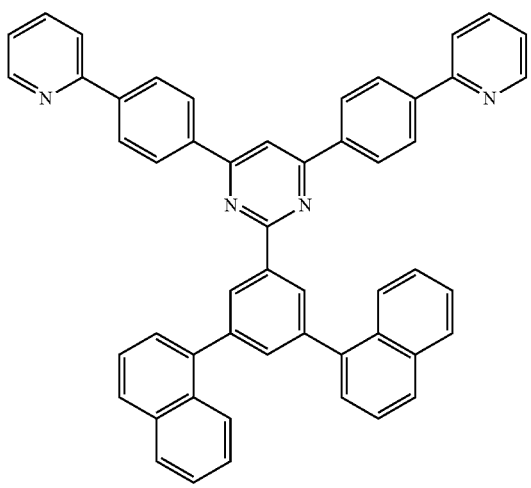
ET34
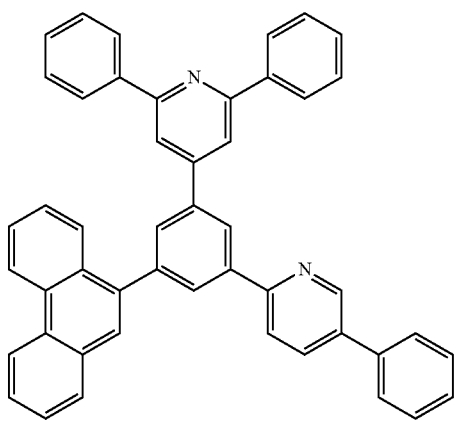
ET35
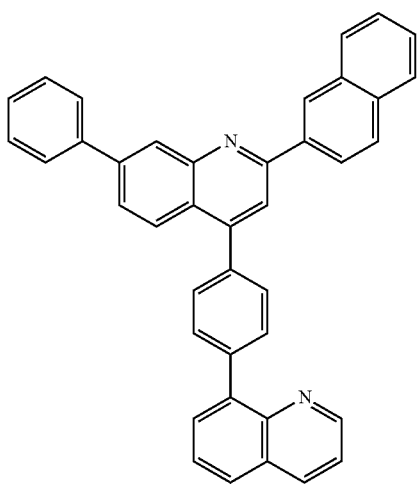
ET36
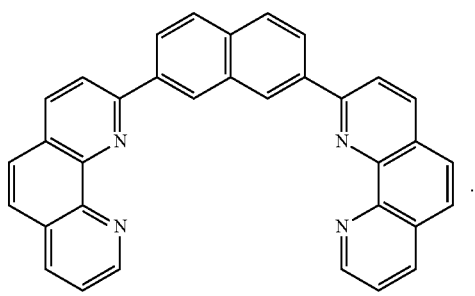
In one or more embodiments, the electron transport region may include at least one compound selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ:

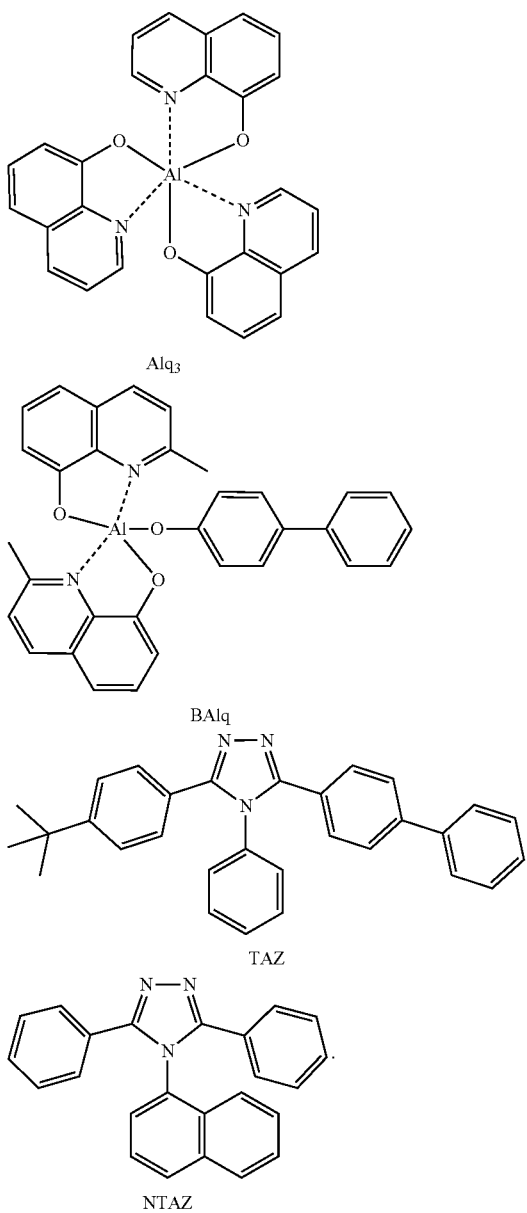

Alq₃

BAlq

TAZ

NTAZ

A thickness of the buffer layer, the hole blocking layer, or the electron control layer may each be in a range of about 20 Å to about 1,000 Å, for example, about 30 Å to about 300 Å. When the thickness of the buffer layer, the hole blocking layer, or the electron control layer are within these ranges, excellent electron blocking characteristics or electron control characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within the range described above, suitable or satisfactory electron transport characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyl oxadiazole, a hydroxy phenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a $L_1$ complex. The Li complex may include, for example, Compound ET-D1 (lithium quinolate, LiQ) or ET-D2:

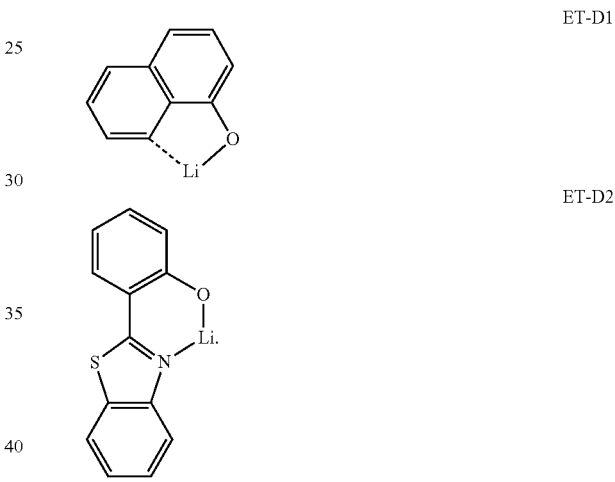

ET-D1

ET-D2

The electron transport region may include an electron injection layer that facilitates electron injection from the second electrode 150. The electron injection layer may directly contact (e.g., physically contact) the second electrode 150.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be $L_1$ or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $Sc_2O_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, suitable or satisfactory electron injection characteristics may be obtained without a substantial increase in driving voltage.

Second Electrode 150

The second electrode 150 may be on the organic layer 130 having such a structure. The second electrode 150 may be a cathode which is an electron injection electrode, and in this regard, a material for forming the second electrode 150 may be selected from metal, an alloy, an electrically conductive compound, and a combination thereof, which have a relatively low work function.

The second electrode 150 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 150 may be a transmissive electrode, a semi-transmissive electrode, or a reflective electrode.

The second electrode 150 may have a single-layered structure, or a multi-layered structure including two or more layers.

Capping Layer 170

In the organic layer 130 of the organic light-emitting device 10, light generated in an emission layer may pass through the first electrode 110 toward the outside, wherein the first electrode 110 may be a semi-transmissive electrode or a transmissive electrode. In the organic layer 130 of the organic light-emitting device 10, light generated in an emission layer may pass through the second electrode 150 and the capping layer 170 toward the outside, wherein the second electrode 190 may be a semi-transmissive electrode or a transmissive electrode.

The capping layer 170 may include the amine-based compound represented by Formula 1 and a radical scavenger.

Hereinbefore, the organic light-emitting device according to an embodiment has been described in connection with FIG. 1.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

Light-Emitting Apparatus

The organic light-emitting device may be included in various suitable light-emitting apparatuses. In one embodiment, a light-emitting apparatus may include: a transistor including a source electrode, a drain electrode, a gate electrode, and an active layer; and the organic light-emitting device, wherein the first electrode of the organic light-emitting device may be electrically coupled to one of the source electrode and the drain electrode of the transistor. The light-emitting apparatus may be used as various suitable displays, light sources, and the like.

Figure 2:
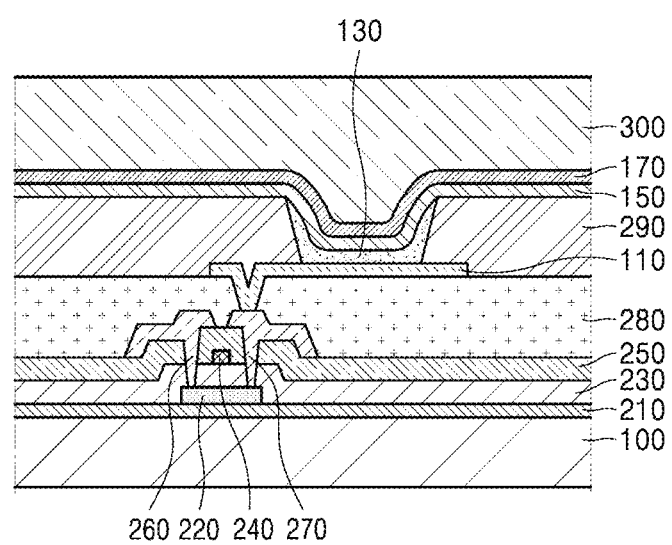
FIG. 2 is a cross-sectional view of a light-emitting apparatus according to an embodiment.

Description of FIG. 2

FIG. 2 is a schematic cross-sectional view of a light-emitting apparatus according to an embodiment.

The light-emitting apparatus includes a substrate 100, a thin film transistor (TFT), an organic light-emitting device, and an encapsulation layer 300 sealing the organic light-emitting device.

The substrate 100 may be a flexible substrate and may include plastic having excellent heat resistance and durability, such as polyimide, polyethylene terephthalate (PET), polycarbonate, polyethylene naphthalate, polyarylate (PAR), and polyetherimide. However, embodiments of the present disclosure are not limited thereto, and the substrate 100 may include various suitable materials such as a metal or glass.

A buffer layer 210 may be formed on the substrate 100. The buffer layer 210 may prevent or reduce penetration of impurities through the substrate 100 and may provide a flat surface on the substrate 100. The buffer layer 210 may include various suitable materials capable of performing such functions.

A TFT may be formed on the buffer layer 210. The TFT may include an active layer 220, a gate electrode 240, a source electrode 260, and a drain electrode 270.

The active layer 220 may include inorganic semiconductor such as silicon or polysilicon, organic semiconductor, or oxide semiconductor, and may include a source region, a drain region, and a channel region.

A gate insulating layer 230 may be formed on the active layer 220 so as to insulate the active layer 220 and the gate electrode 240, and a gate electrode 240 may be formed on the gate insulating layer 230.

An interlayer insulating layer 250 may be formed on the gate electrode 240. The interlayer insulating layer 250 may be between the gate electrode 240 and the source electrode 260 and between the gate electrode 240 and the drain electrode 270 so as to insulate them.

A source electrode 260 and a drain electrode 270 may be formed on the interlayer insulating layer 250. The interlayer insulating layer 250 and the gate insulating layer 230 may be formed so as to expose the source region and the drain region of the active layer 220, and the source electrode 260 and the drain electrode 270 may be formed so as to be in contact (e.g., physical contact) with the exposed source region and the exposed drain region of the active layer 220.

The TFT may be electrically coupled to the organic light-emitting device so as to drive the organic light-emitting device, and may be protected by being covered with a passivation layer 280. The passivation layer 280 may include an inorganic insulating layer and/or an organic insulating layer. An organic light-emitting device may be provided on the passivation layer 280. The organic light-emitting device may include a first electrode 110, an organic layer 130, and a second electrode 150.

The first electrode 110 may be formed on the passivation layer 280. The passivation layer 280 may be formed so as to expose a set or predetermined region without covering the entire drain electrode 270, and the first electrode 110 may be formed so as to be coupled to the exposed drain electrode 270.

A pixel defining layer 290 including an insulating material may be formed on the first electrode 110. The pixel defining layer 290 may expose a set or predetermined region of the first electrode 110, and the organic layer 130 including an emission layer may be formed in the exposed region. The pixel defining layer 290 may include a polyimide-based organic layer or a polyacryl-based organic layer.

The second electrode 150 may be formed on the organic layer 130. A capping layer 170 may be further formed on the second electrode 150. The capping layer 170 may be formed so as to cover the second electrode 150. The capping layer 170 may include an amine-based compound represented by Formula 1 and a radical scavenger.

For example, the pixel defining layer 290 may be an organic layer. When the organic layer is exposed to UV light, out-gassing may occur and radicals may be generated by the out-gassing components. The radicals generated in the pixel defining layer 290 may directly affect the second electrode 150, or may affect the second electrode 150 by penetrating through the organic layer 130. For example, because the radicals react with the second electrode 150 and the second electrode is oxidized, the pixel shrinkage of the organic light-emitting device may occur.

In order to prevent or reduce this phenomenon, the capping layer 170 including a radical scavenger may be on the second electrode 150 so as to effectively remove or reduce the concentration of the radicals moving through the second electrode 150. Therefore, because reaction of the radicals with the second electrode 150 is prevented or reduced, the oxidation of the second electrode 150 may be prevented or reduced. Therefore, the organic light-emitting device according to the embodiment may prevent or reduce the pixel shrinkage caused by the oxidation of the second electrode 150.

An encapsulation layer 300 may be formed on the capping layer 170. The encapsulation layer 300 may be on the organic light-emitting device and may serve to protect the organic light-emitting device from moisture or oxygen. The encapsulation layer 300 may include an inorganic film including silicon nitride (SiNx), silicon oxide (SiOx), indium tin oxide, or indium zinc oxide, or an organic film including polyethylene terephthalate, polyethylene naphthalate, polycarbonate, polyimide, polyethylene sulfonate, polyoxymethylene, polyarylate, hexamethyldisiloxane, an acrylate-based resin (for example, polymethylmethacrylate, polyacrylic acid, or the like), or any combination thereof, or may include both the inorganic film and the organic film.

General Definition of at Least Some of the Substituents

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminal end (e.g., at the terminus) of the $C_2$-$C_{60}$ alkyl group, and examples thereof include an ethenyl group, a propenyl group, and a butenyl group.

The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminal end (e.g., at the terminus) of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the ring and/or group is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group," as used herein, refers to a monovalent group having two or more rings condensed with each other (e.g., combined together), only carbon atoms (for example, having 8 to 60 carbon atoms) as ring-forming atoms, and no aromaticity in its entire molecular structure (e.g., the entire molecular structure is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecular structure is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The term "$C_5$-$C_{60}$ carbocyclic group," as used herein, refers to an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

In the present specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a 01-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "But," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group". In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, an organic light-emitting device according to an embodiment will be described in more detail with reference to Synthesis Examples and Examples. The wording "B was used instead of A" used in describing Synthesis Examples refers to that an identical molar equivalent of B was used in place of A.

SYNTHESIS EXAMPLES

Synthesis Example 1: Synthesis of Compound

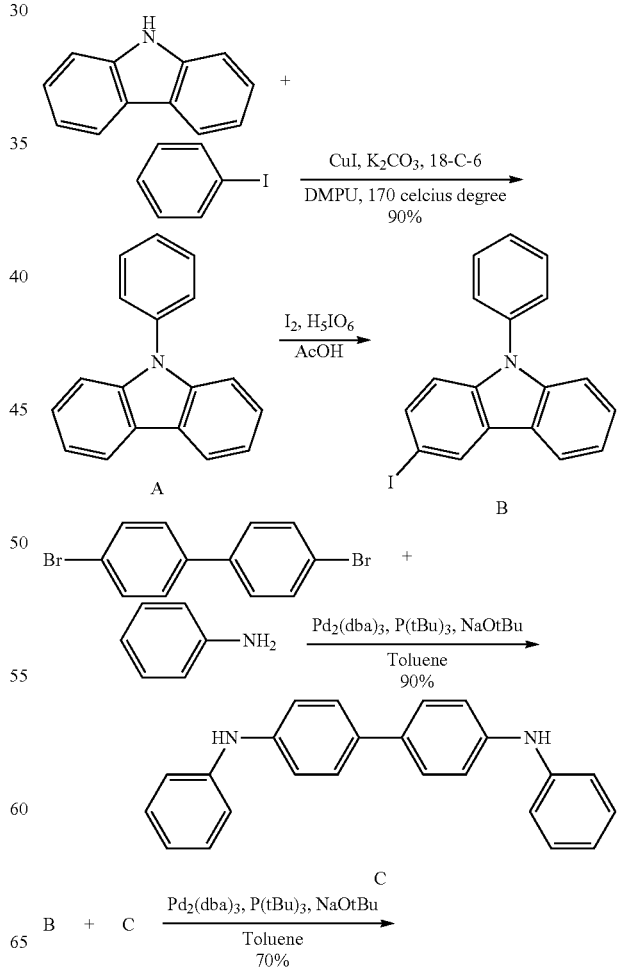

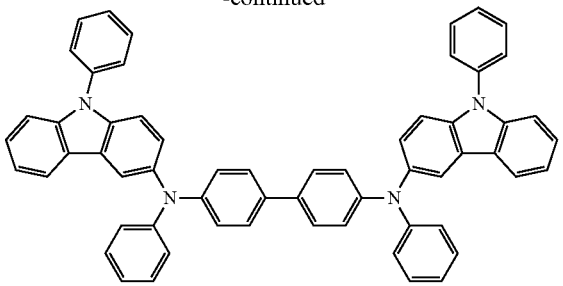

(1) Synthesis of Intermediate A

Carbazole (16.7 g, 100 mmol), iodobenzene (26.5 g, 130 mmol), CuI (1.9 g, 10 mmol), K$_2$CO$_3$ (138 g, 1 mol), and 18-crown-6 (18-C-6) (530 mg, 2 mmol) were dissolved in 1,3-dimethyl-3,4,5,6-tetrahydro-(1H)-pyrimidinone (DMPU) (500 mL) and heated at a temperature of 170° C. for 8 hours.

After the reaction was completed, the reaction mixture was cooled to room temperature. A solid material was filtered, and a small amount of ammonia water was added to the resultant filtrate. Washing was performed thereon three times by using diethyl ether (300 mL). The washed diethyl ether layer was dried by using MgSO$_4$ and dried under reduced pressure to obtain a crude product. The crude product was separated and purified by silica gel column chromatography to obtain 22 g (yield of 90%) of Intermediate A as a white solid.

$^1$H NMR (CDCl$_3$, 400 MHz) δ (ppm) 8.12 (d, 2H), 7.58-7.53 (m, 4H), 7.46-7.42 (m, 1H), 7.38 (d, 4H), 7.30-7.26 (m, 2H)

$^{13}$C NMR (CDCl$_3$, 100 MHz) δ (ppm) 141.0, 137.9, 130.0, 127.5, 127.3, 126.0, 123.5, 120.4, 120.0, 109.9

(2) Synthesis of Intermediate B 2.433 g (10 mmol) of Intermediate A were added to 100 mL of 80% acetic acid (AcOH), and 1.357 g (5.35 mmol) of iodine (I2) and 0.333 g (1.46 mmol) of ortho-periodic acid (H$_5$IO$_6$) were added thereto in a solid state and stirred at a temperature of 80° C. for 2 hours in a nitrogen atmosphere.

After the reaction was completed, an organic layer was extracted therefrom three times by using ethyl ether (50 mL). The collected organic layer was dried by using MgSO$_4$, and a residue obtained by evaporating a solvent therefrom was separated and purified by silica gel column chromatography to obtain 3.23 g (yield of 87%) of Intermediate B as a white solid.

$^1$H NMR (CDCl$_3$, 300 MHz) δ (ppm) 8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

(3) Synthesis of Intermediate C 3.12 g (10 mmol) of 4,4'-dibromodiphenyl, 2.3 mL (25 mmol) of aniline, 2.9 g (30 mmol) of t-BuONa, 183 mg (0.2 mmol) of Pd$_2$(dba)$_3$, and 20 mg (0.1 mmol) of P(t-Bu)$_3$ were dissolved in 30 mL of toluene and stirred at a temperature of 90° C. for 3 hours.

The reaction mixture was cooled to room temperature, and an organic layer was extracted therefrom three times by using 30 mL of distilled water and diethyl ether. A precipitate existing in the organic layer was filtered, washed by using acetone and diethyl ether, and then vacuum-deposited to obtain 0.3 g (yield of 90%) of Intermediate C. The structure of intermediate C was identified by $^1$H NMR.

$^1$H NMR (DMSO-d6, 400 MHz) δ (ppm) 8.22 (s, 2H), 7.48 (d, 4H), 7.23 (t, 4H), 7.10 (dd, 8H), 6.82 (t, 2H)

$^{13}$C NMR (DMSO-d6, 100 MHz) δ (ppm) 145.7, 144.3, 133.7, 131.4, 128.7, 121.2, 119.2, 118.9

(4) Synthesis of Compound 1

912 mg (2.47 mmol) of Intermediate B, 336.4 mg (1 mmol) of Intermediate C, 300 mg (3 mmol) of t-BuONa (NaOtBu), 40 mg (0.02 mmol) of Pd$_2$(dba)$_3$, and 3 mg (0.01 mmol) of P(t-Bu)$_3$ were dissolved in 5 mL of toluene and stirred at a temperature of 90° C. for 3 hours.

After the reaction was completed, the reaction mixture was cooled to room temperature, and an organic layer was extracted therefrom three times by using 30 mL of distilled water and diethyl ether. The collected organic layer was dried by using MgSO$_4$, and a residue obtained by evaporating a solvent therefrom was separated and purified by silica gel column chromatography to obtain 570 mg (yield of 70%) of Compound 1 as a yellow solid.

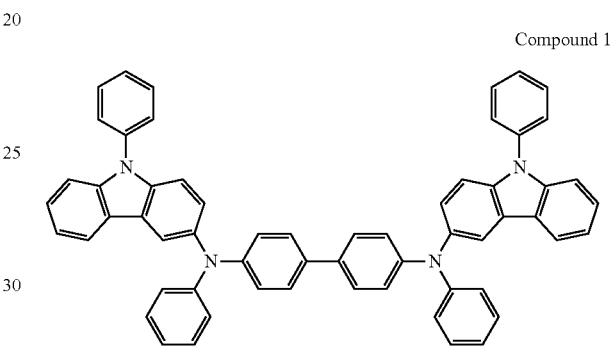

Compound 1

$^1$H NMR (CDCl$_3$, 300 MHz) δ (ppm) 7.99 (d, 2H), 7.95 (s, 2H), 7.61-7.57 (m, 8H), 7.48-7.32 (m, 12H), 7.27-7.19 (m, 8H), 7.18-7.10 (m, 8H), 6.96 (t, 2H)

$^{13}$C NMR (CDCl$_3$, 100 MHz) δ (ppm) 148.4, 147.3, 141.3, 140.4, 138.0, 137.6, 133.9, 129.9, 129.1, 127.4, 127.1, 127.0, 126.1, 125.6, 124.3, 123.0, 122.9, 122.8, 121.7, 120.5, 119.9, 118.5, 110.7, 109.9

Synthesis Example 2: Synthesis of HALS-1

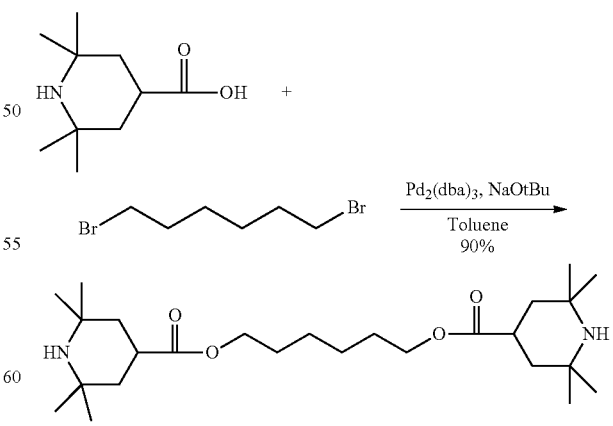

0.1 g (1 mmol) of 1,6-dibromohexane, 7.8 g (2.5 mmol) of 2,2,6,6-tetramethylpiperidine-4-carboxylic acid, and 183 mg (0.2 mmol) of Pd$_2$(dba)$_3$ were dissolved in 80 mL of toluene and stirred at a temperature of 90° C. for 5 hours.

The reaction mixture was cooled to room temperature, and an organic layer was extracted therefrom three times by using 30 mL of distilled water and diethyl ether. A precipitate existing in the organic layer was filtered, washed by using by using acetone and diethyl ether, and then vacuum-deposited to obtain 3.02 g (yield of 90%) of hexane-1,6-diyl bis(2,2,6,6-tetramethylpiperidine-4-carboxylate (HALS-1).

EXAMPLES

Figure 3A:
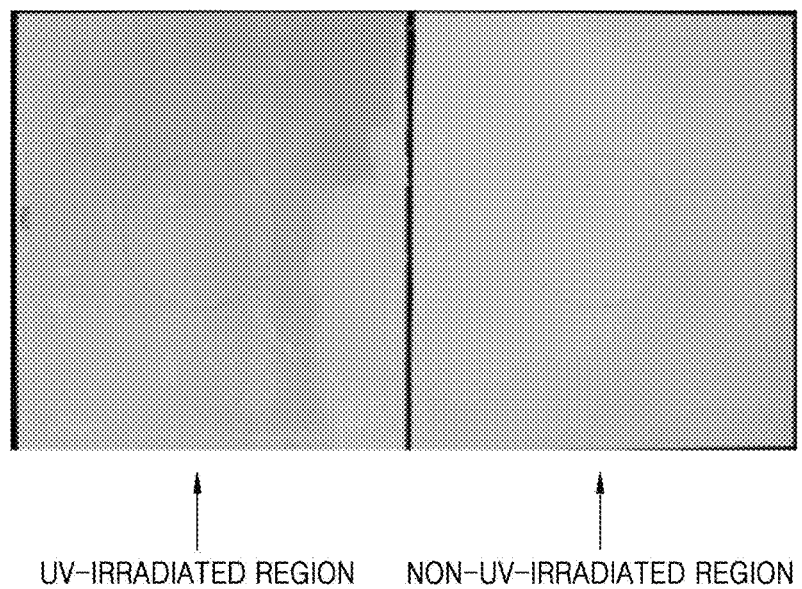
FIGS. 3A and 3B are images showing a change in color temperature after UV light irradiation of a light-emitting apparatus of Comparative Example 1.
Figure 3B:
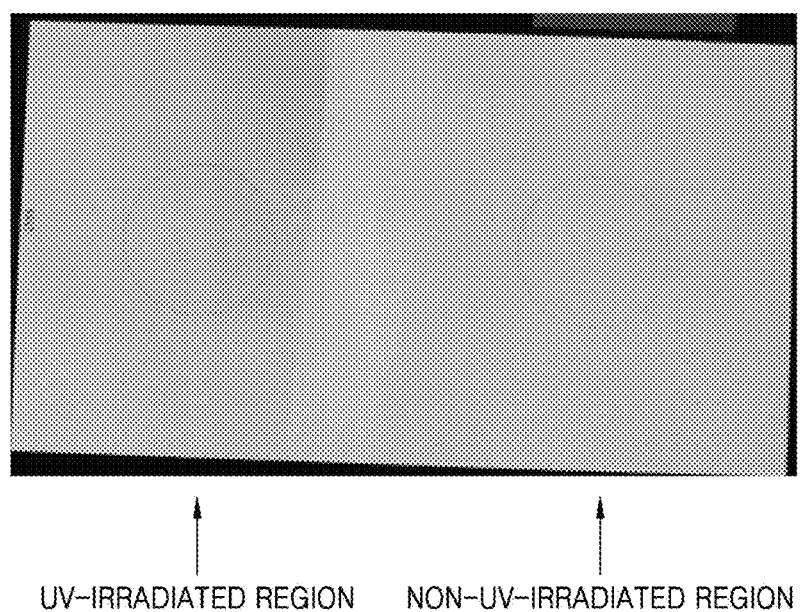
Figure 4:
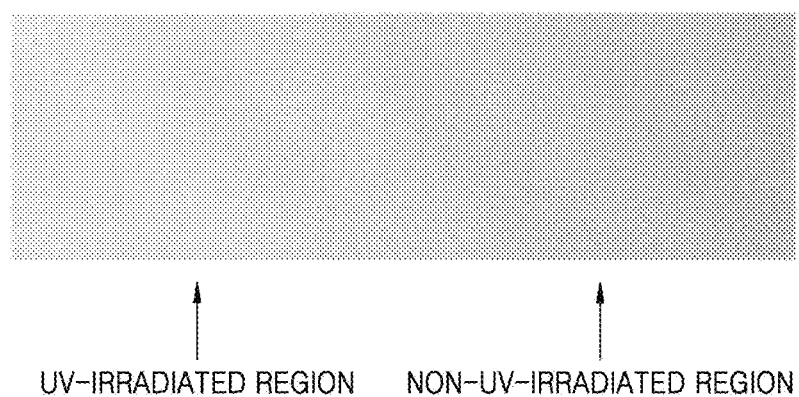
FIG. 4 is an image showing a change in color temperature after UV light irradiation of a light-emitting apparatus of Example 1.

FIGS. 3A, 3B, and 4 are images showing a change in color temperature before and after UV light irradiation of a light-emitting apparatus irradiation of UV light according to a material for a capping layer.

In Example 1, Compound 1 and HALS-1 (radial scavenger) were co-deposited to a weight ratio of 99:1 to form a capping layer. In Comparative Example 1, only Compound 1 was deposited to form a capping layer. In Comparative Example 2, an acrylic resin A1 and HALS-1 were used at a weight ratio of 99:1 to form a capping layer.

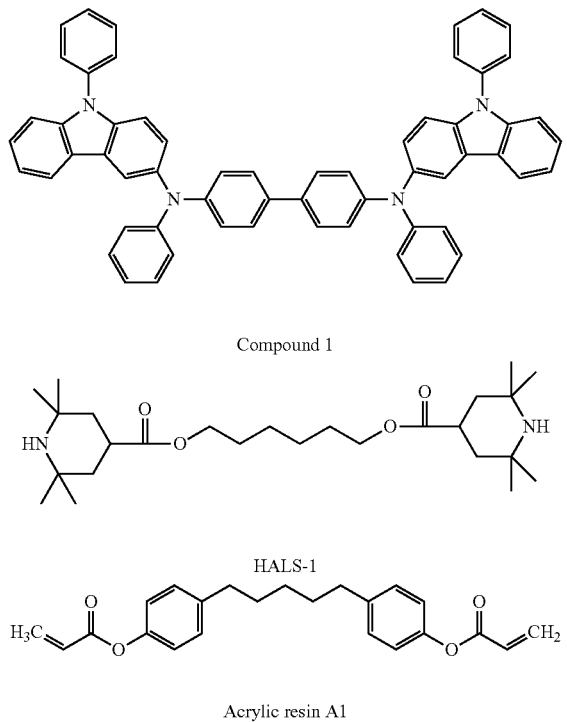

Compound 1

HALS-1

Acrylic resin A1

Evaluation Example: Evaluation of Solar Test

The color temperature and change in emission regions of red, green, and blue sub-pixels before and after irradiation of UV light with respect to the light-emitting apparatuses of Example 1 and Comparative Examples 1 and 2 were confirmed and evaluated.

The experiment was performed by exposing each apparatus to UV light in a state in which a UV lamp was turned on. A half region of each apparatus was irradiated with UV light, and the other half region of each apparatus was not irradiated with UV light. Then, the change in color temperature before and after the irradiation of the UV light was confirmed.

FIGS. 3A and 3B are images showing the change in color temperature after UV light irradiation of a light-emitting apparatus of Comparative Example 1, respectively, and FIG. 4 is an image showing the change in color temperature after UV light irradiation of a light-emitting apparatus of Example 1.

When comparing the UV light irradiation region with the UV non-irradiation region in FIGS. 3A and 3B, it is confirmed that the color temperature of the UV light irradiation region after the irradiation of the UV light was changed and spots were generated. In contrast, when comparing the UV light irradiation region with the UV non-irradiation region in FIG. 4, it is confirmed that there was no substantial difference in color temperature between the UV light irradiation region and the UV non-irradiation region. The change in color temperature of each sample is shown in Table 1 as a percentage based on Example 1.

Figure 5A:
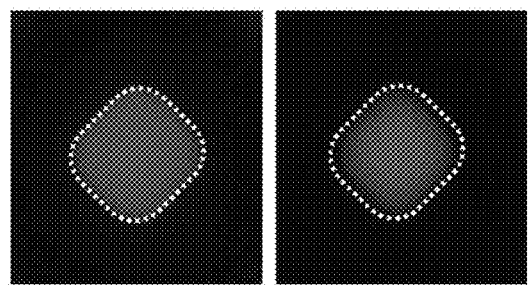
FIGS. 5A to 5C are images showing shrinkage of emission regions of red, green, and blue sub-pixels before and after UV light irradiation of the light-emitting apparatus of Comparative Example 1.
Figure 5B:
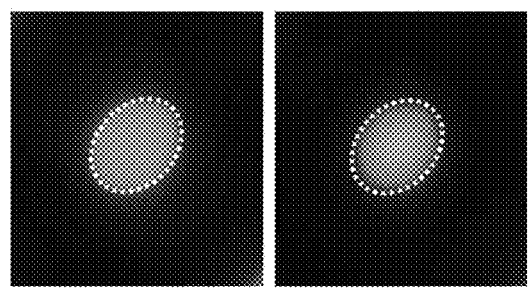
Figure 5C:
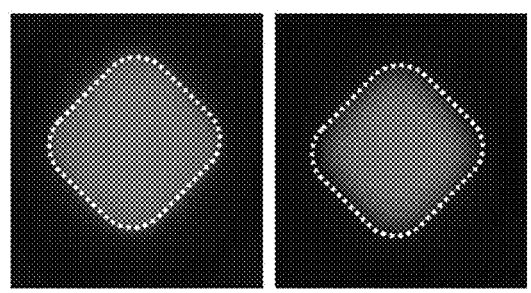
Figure 6A:
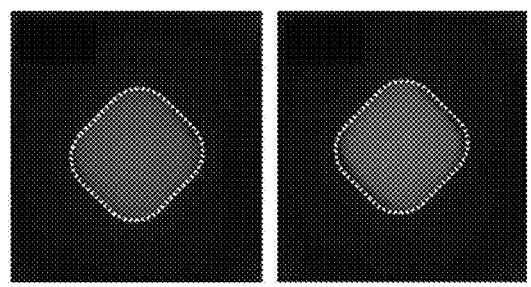
FIGS. 6A to 6C are images showing shrinkage of emission regions of red, green, and blue sub-pixels before and after UV light irradiation of the light-emitting apparatus of Example 1.
Figure 6B:
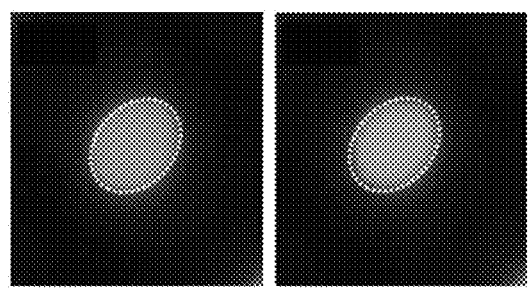
Figure 6C:
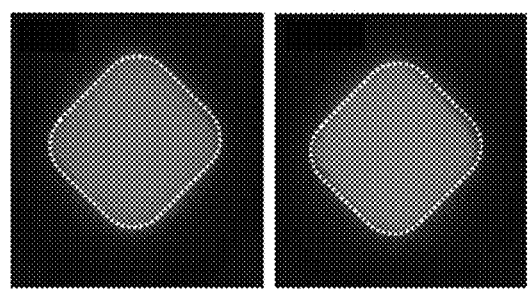

FIGS. 5A to 5C are images showing the change in emission regions of red, green, and blue sub-pixels before and after the UV light irradiation of the light-emitting apparatus of Comparative Example 1, and FIGS. 6A to 6C are images showing the change in emission regions of red, green, and blue sub-pixels before and after the UV light irradiation of the light-emitting apparatus of Example 1. In each drawing, the left side is an image observing the size of the emission region before the UV light irradiation, and the right side is an image observing the size of the emission region after the UV light irradiation.

When comparing the emission regions before and after the irradiation of the UV light, it is confirmed that in the case of Comparative Example 1, the boundary of the emission region becomes blurred and the size of the emission region is reduced, as compared with the case of Example 1. In the case of Example 1, it is confirmed that there is no substantial change in the size of the emission region.

Figure 7A:
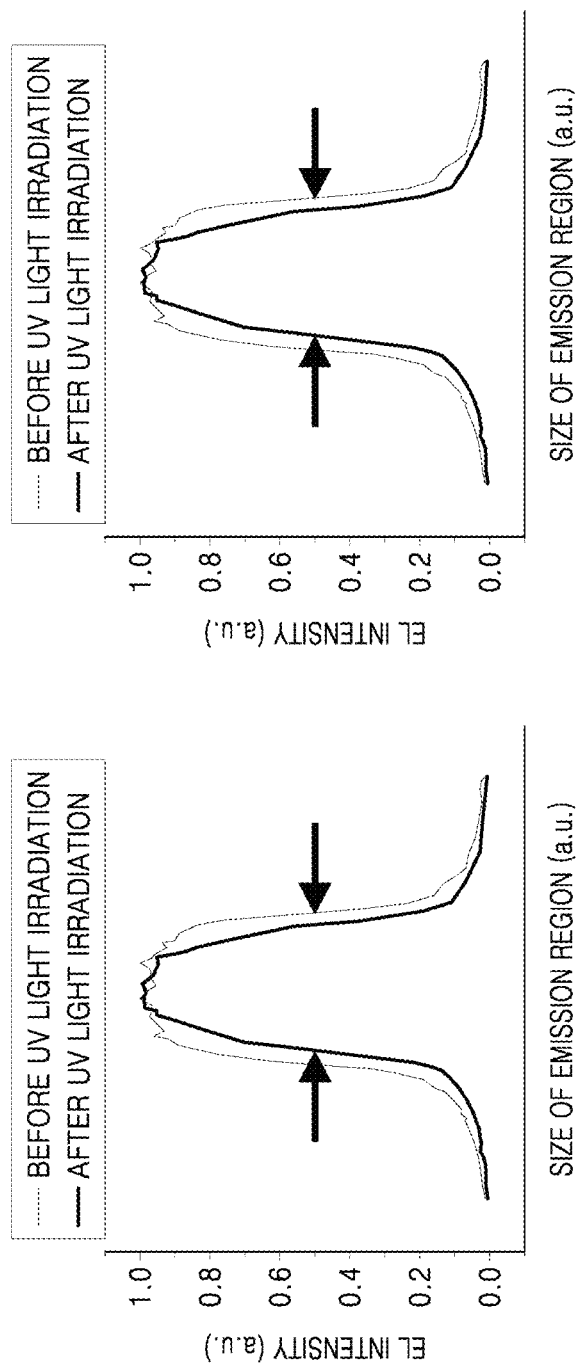
FIGS. 7A to 7C are graphs showing a change in size of emission regions of red, green, and blue sub-pixels before and after UV light irradiation of the light-emitting apparatus of Comparative Example 1.
Figure 7B:
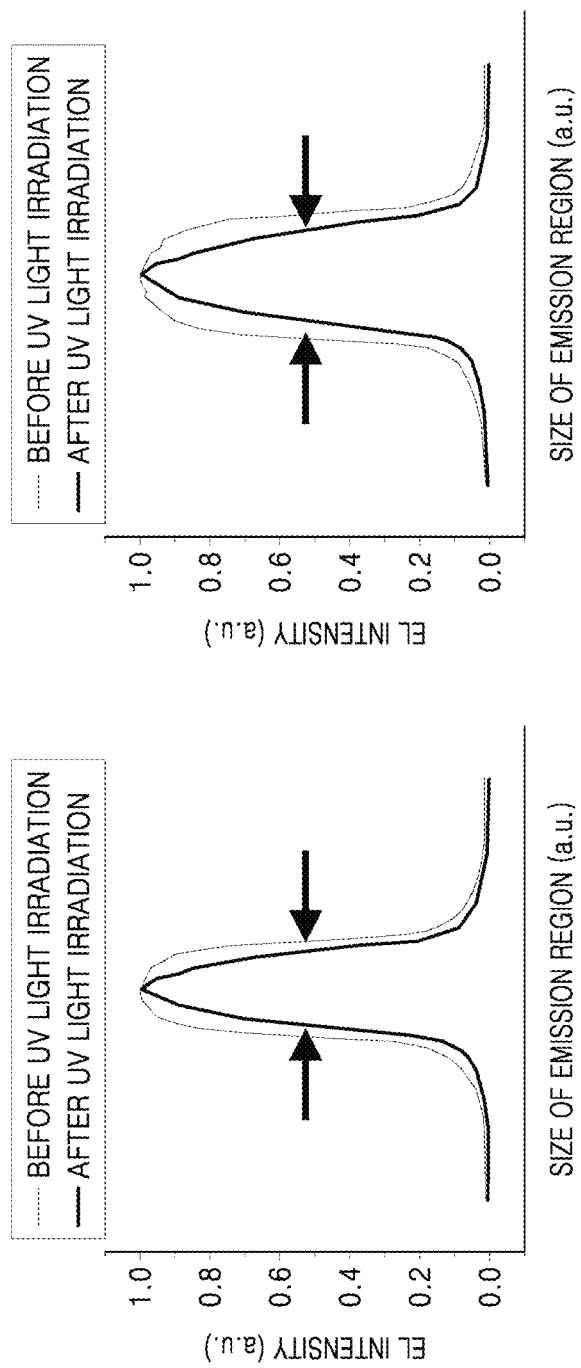
Figure 7C:
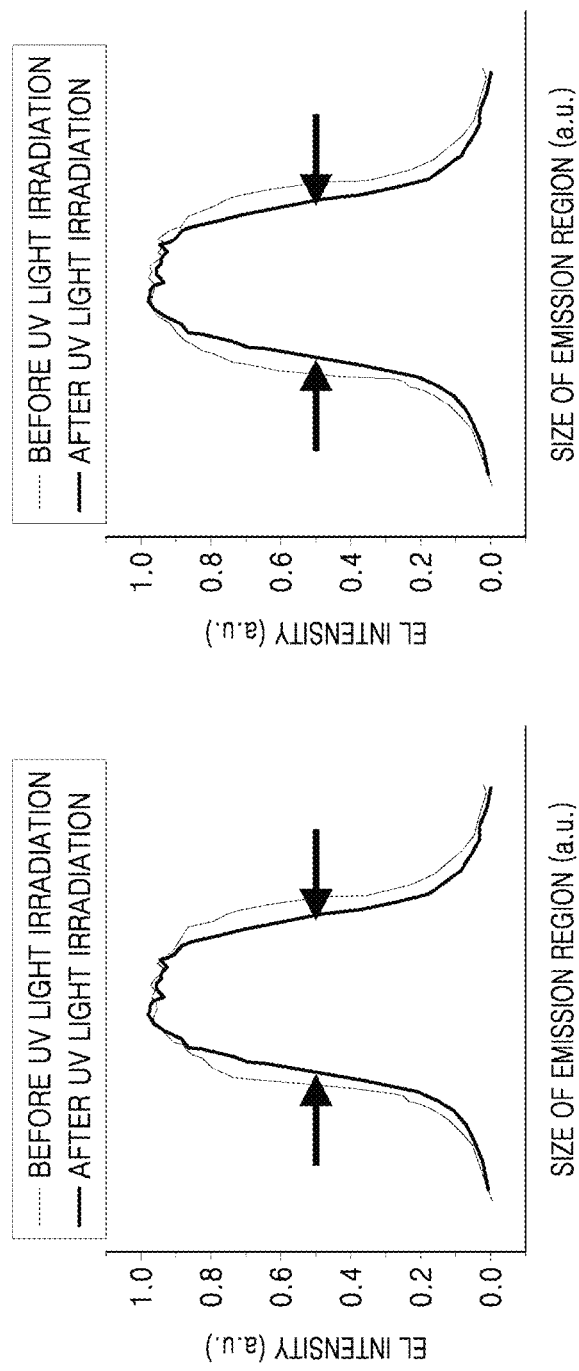
Figure 8A:
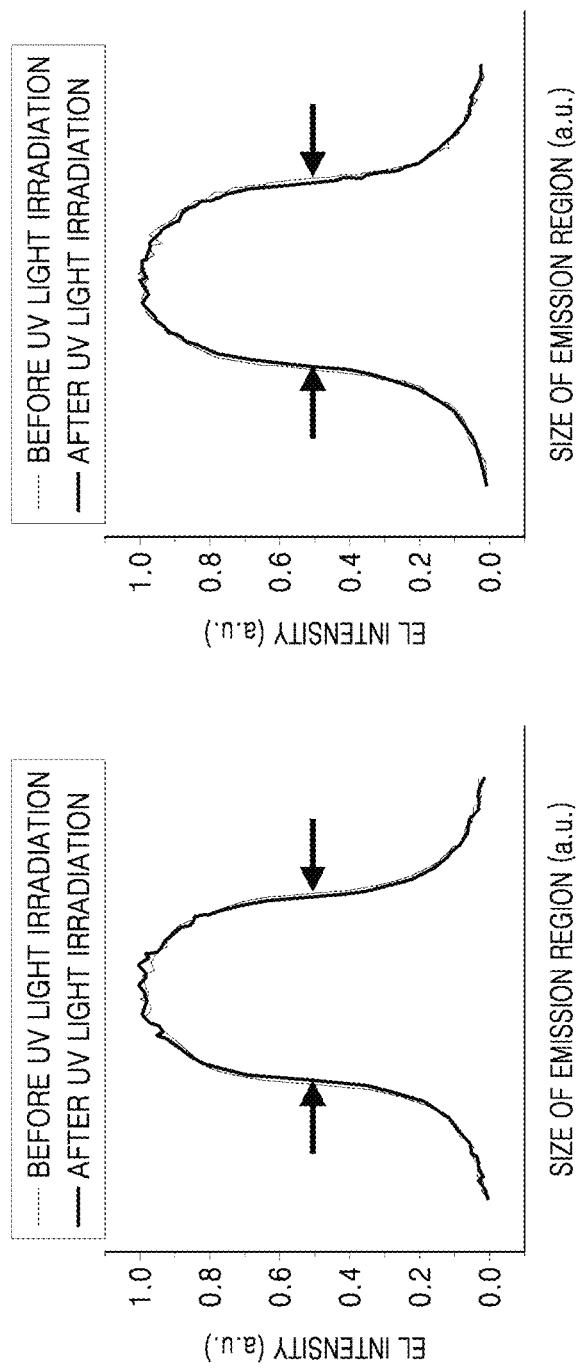
FIGS. 8A to 8C are graphs showing a change in size of emission regions of red, green, and blue sub-pixels before and after UV light irradiation of the light-emitting apparatus of Example 1.
Figure 8B:
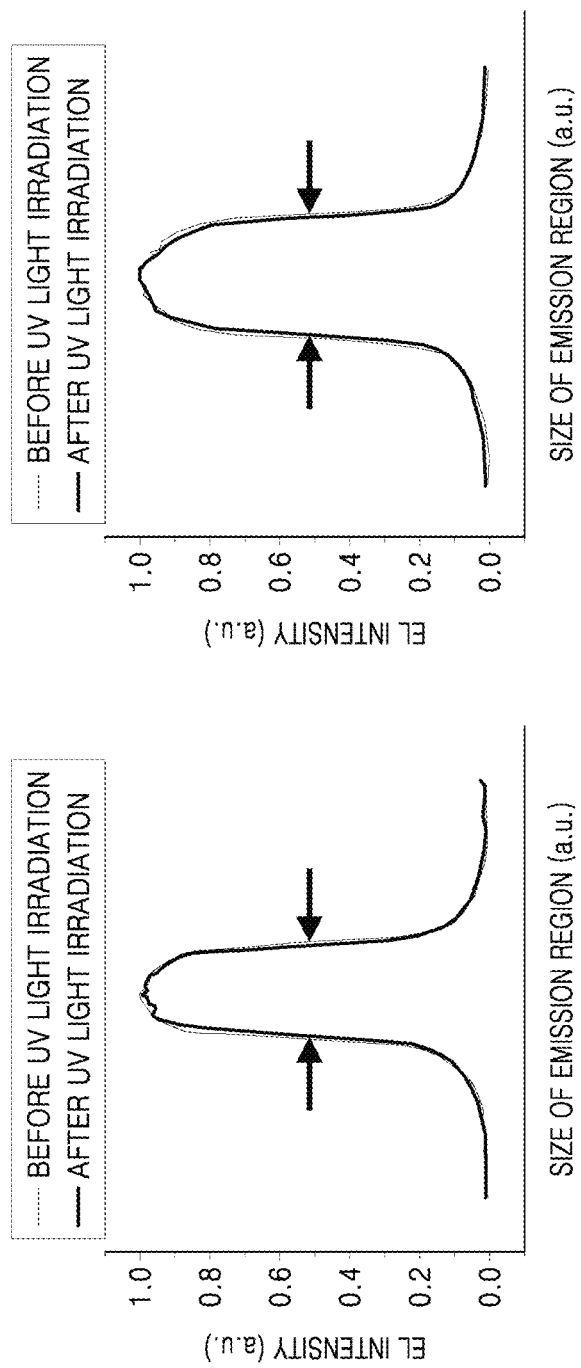
Figure 8C:
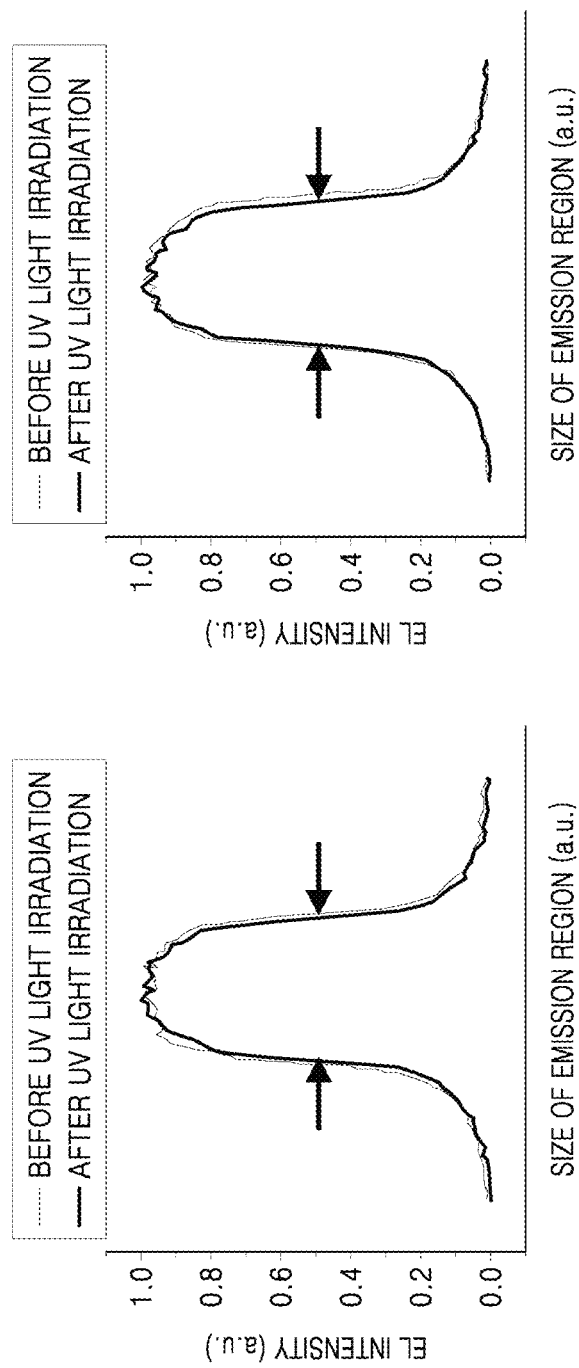

FIGS. 7A to 7C are graphs showing the change in the size of the emission region before and after the irradiation of the UV light with respect to two red, green, and blue sub-pixels positioned in the light-emitting apparatus of Comparative Example 1. FIGS. 8A to 8C are graphs showing the change in the size of the emission region before and after the irradiation of the UV light with respect to two red, green, and blue sub-pixels positioned in the light-emitting apparatus of Example 1. In FIGS. 7A to 7C and 8A to 8C, the scales of the horizontal axes are the same as each other.

It is confirmed that in the case of Example 1, the pixel shrinkage of each sub-pixel is reduced by 60% or more, as compared with the case of Comparative Example 1.

The degree of pixel shrinkage of each sample is shown in Table 1 as a percentage based on Example 1.

TABLE 1

|  | Change in color temperature (%) | Maximum pixel shrinkage (%) | Minimum pixel shrinkage (%) |
|---|---|---|---|
| Example 1 | 100% | 100% | 100% |
| Comparative Example 1 | 526% | 345% | 345% |
| Comparative Example 2 | 511% | 610% | 262% |

Because the organic light-emitting device minimizes or reduces the influence of the organic light-emitting device on ultraviolet (UV) light, the organic light-emitting device may prevent or reduce a pixel shrinkage phenomenon and may have high efficiency and a long lifespan.

It should be understood that embodiments described herein should be considered in a descriptive sense only and not for purposes of limitation. Descriptions of features or aspects within each embodiment should be considered as available for other similar features or aspects in other embodiments.

As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An organic light-emitting device, comprising:
a first electrode;
a second electrode facing the first electrode;
an organic layer between the first electrode and the second electrode and comprising an emission layer; and
a capping layer on the second electrode,
wherein the capping layer comprises an amine-based compound represented by Formula 1 and a radical scavenger:

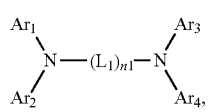

Formula 1 wherein, in Formula 1,
$L_1$ is selected from a substituted or unsubstituted $C_5$-$C_{60}$ carbocyclic group, a substituted or unsubstituted $C_1$-$C_{60}$ heterocyclic group, a substituted or unsubstituted $C_1$-$C_{60}$ alkylene group, *—O—*', *—N($R_1$)—*', *—(C=O)—O—*', and *—O—(C=O)—*',
n1 is an integer from 1 to 5, $Ar_1$ to $Ar_4$ are each independently selected from groups represented by Formulae 2A to 2C, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $Ar_1$ to $Ar_4$ is selected from groups represented by Formulae 2A to 2C:

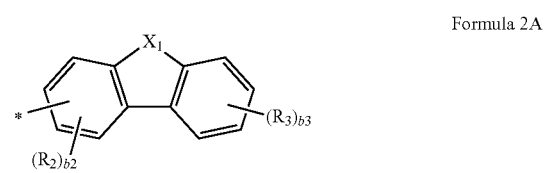

Formula 2A

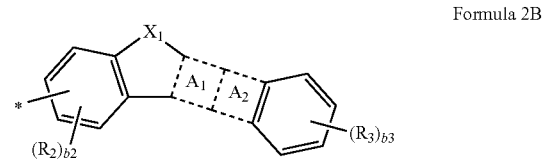

Formula 2B

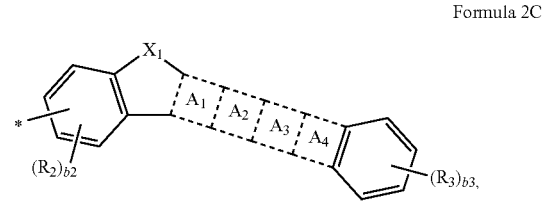

Formula 2C wherein, in Formulae 2A to 2C,
$X_1$ is selected from $C(R_4)(R_5)$, $Si(R_4)(R_5)$, $N(R_4)$, O, and S,
ring $A_1$ and ring $A_3$ are each independently a substituted or unsubstituted benzene ring,
ring $A_1$ is condensed with a neighboring 5-membered ring, and ring $A_3$ is condensed with a neighboring 5-membered ring, and
ring $A_2$ is a 5-membered ring represented by Formula 3A, and ring $A_4$ is a 5-membered ring represented by Formula 3B:

Formula 3A

Formula 3B wherein, in Formulae 3A and 3B,
$X_2$ is selected from $C(R_6)(R_7)$, $Si(R_6)(R_7)$, $N(R_6)$, O, and S,
$X_3$ is selected from $C(R_8)(R_9)$, $Si(R_8)(R_9)$, $N(R_8)$, O, and S,
in Formulae 1, 2A to 2C, 3A, and 3B,
$R_1$ to $R_9$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b2 is an integer from 1 to 3, b3 is an integer from 1 to 4, at least one substituent of the substituted $C_5$-$C_{60}$ carbocyclic group, the substituted $C_1$-$C_{60}$ heterocyclic group, the substituted $C_1$-$C_{60}$ alkylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *[1] each indicate a binding site to a neighboring atom.

2. The organic light-emitting device of claim 1, wherein:

$L_1$ is selected from a cyclobutylene group, a cyclopentylene group, a cyclohexylene group, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, and a dibenzosilolylene group;

a cyclobutylene group, a cyclopentylene group, a cyclohexylene group, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pyridinylene group, a pyrazinylene group, a pyrimidinylene group, a quinolinylene group, an isoquinolinylene group, a benzoquinolinylene group, a naphthyridinylene group, a quinoxalinylene group, a quinazolinylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, and a dibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$); and a substituted or unsubstituted $C_1$-$C_{60}$ alkylene group, *—(C=O)—O—*', and *—O—(C=O)—*', and $Q_{31}$ to $Q_{33}$ and $R_1$ are each independently selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

3. The organic light-emitting device of claim 1, wherein: $L_1$ is selected from groups represented by Formulae 4-1 to 4-26, a substituted or unsubstituted $C_1$-$C_{20}$ alkylene group, *—O—*', *—(C=O)—O—*', and *—O—(C=O)—*':

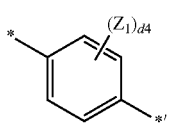

4-1

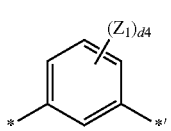

4-2

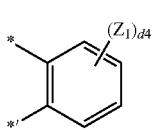

4-3

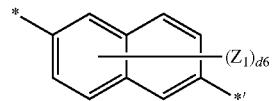

4-4

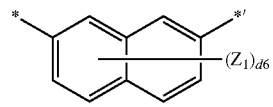

4-5

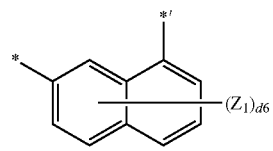

4-6

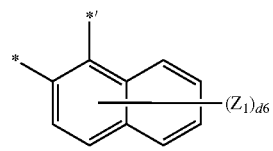

4-7

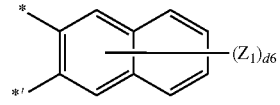

4-8

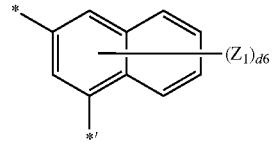

4-9

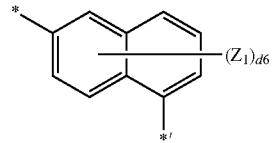

4-10

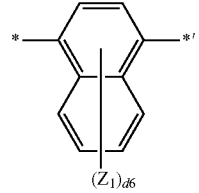

4-11

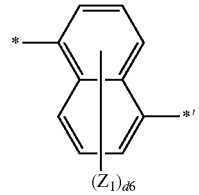

4-12

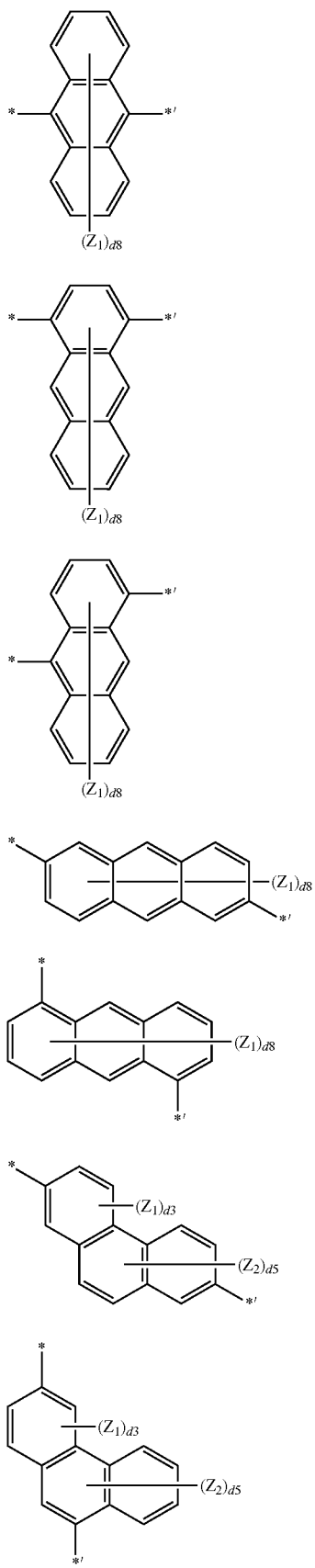

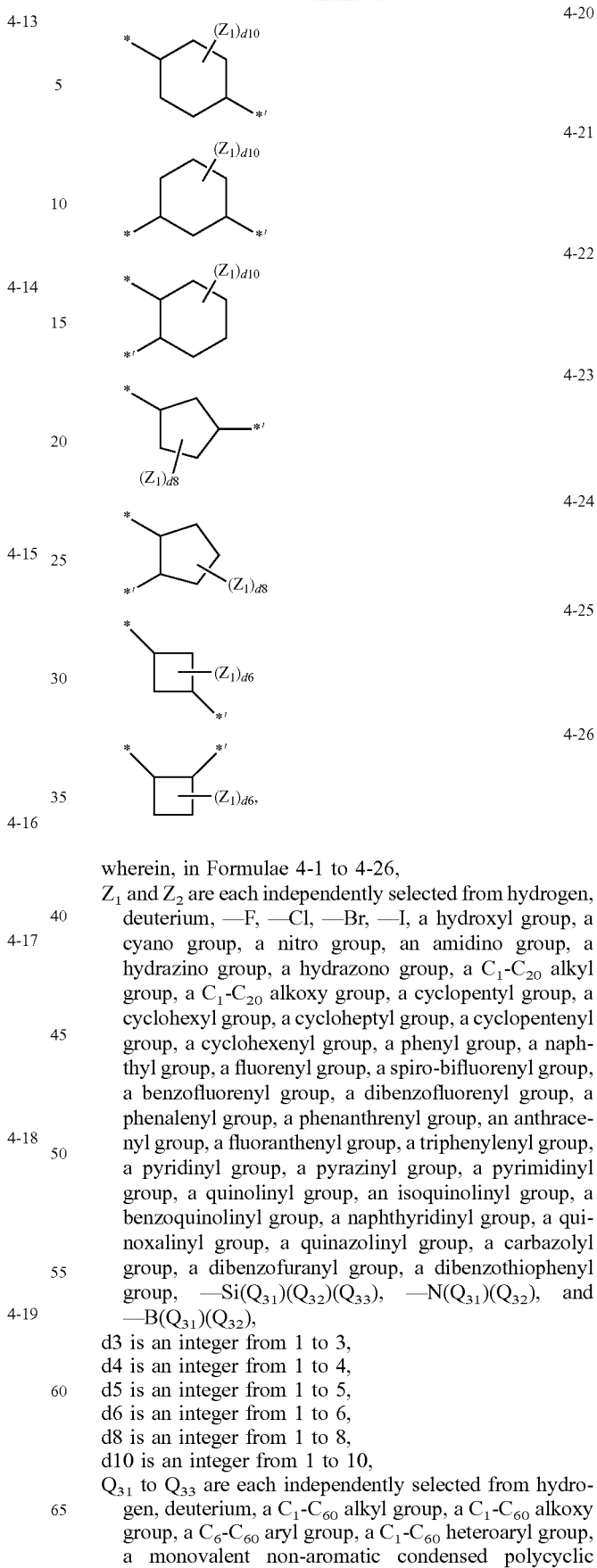

wherein, in Formulae 4-1 to 4-26,

Z₁ and Z₂ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a dibenzofuranyl group, a dibenzothiophenyl group, —Si(Q₃₁)(Q₃₂)(Q₃₃), —N(Q₃₁)(Q₃₂), and —B(Q₃₁)(Q₃₂), d3 is an integer from 1 to 3,
d4 is an integer from 1 to 4,
d5 is an integer from 1 to 5,
d6 is an integer from 1 to 6,
d8 is an integer from 1 to 8,
d10 is an integer from 1 to 10, Q₃₁ to Q₃₃ are each independently selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *¹ each indicate a binding site to a neighboring atom.

4. The organic light-emitting device of claim 1, wherein: n1 is an integer from 1 to 3.

5. The organic light-emitting device of claim 1, wherein:
$Ar_1$ to $Ar_4$ are each independently selected from groups represented by Formulae 2A to 2C, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a furanyl group, a benzofuranyl group, a thiophenyl group, a benzothiophenyl group, a thiazolyl group, an isothiazolyl group, a benzothiazolyl group, an oxazolyl group, an isoxazolyl group, a benzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, —Si($Q_{31}$)($Q_{32}$)($Q_{33}$), —N($Q_{31}$)($Q_{32}$), and —B($Q_{31}$)($Q_{32}$), and $Q_{31}$ to $Q_{33}$ are each independently selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

6. The organic light-emitting device of claim 1, wherein:
at least one selected from $Ar_1$ to $Ar_4$ is selected from groups represented by Formulae 2A, 2B-1 to 2B-6, and 2C-1 to 2C-36:

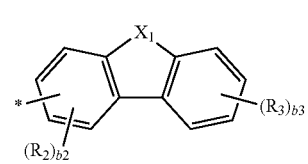

2A

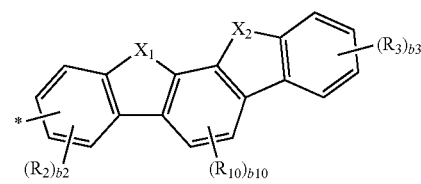

2B-1

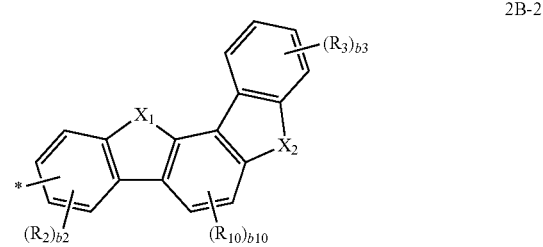

2B-2

2B-3
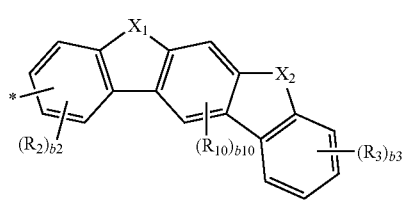
2B-4
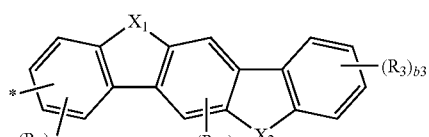
2B-5
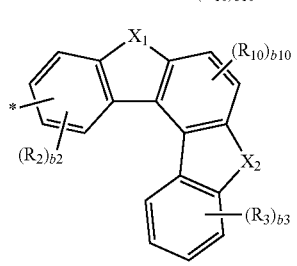
2B-6
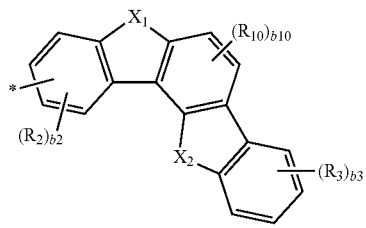
2C-1
2C-2
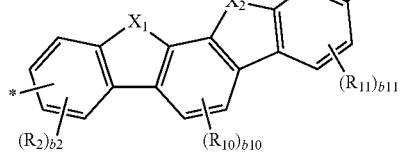
2C-3
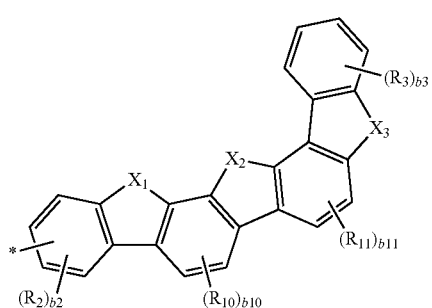
2C-4
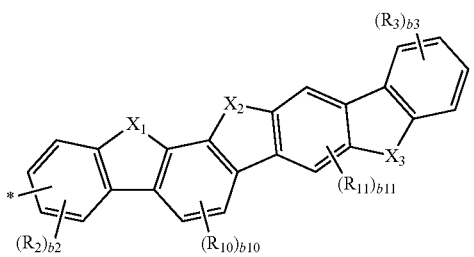
2C-5
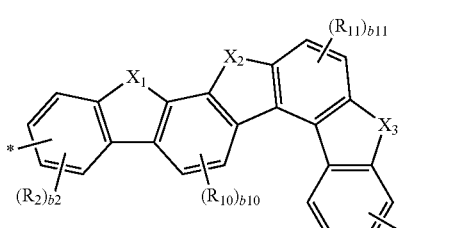
2C-6
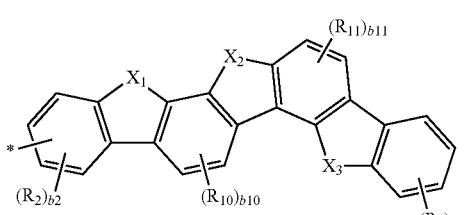
2C-7
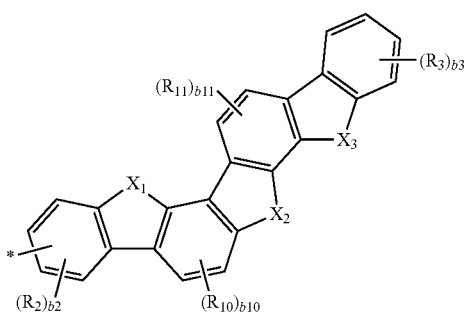
2C-8
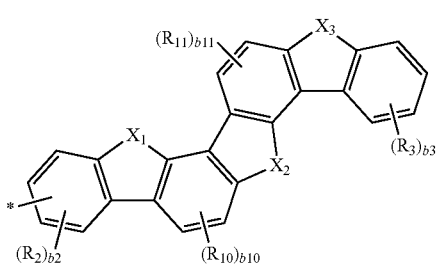
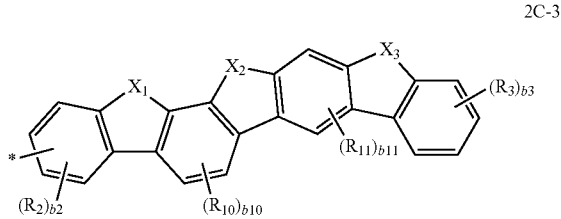

-continued
2C-9
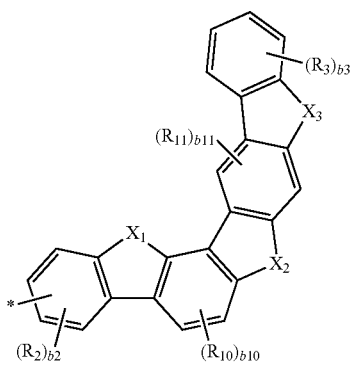
2C-10
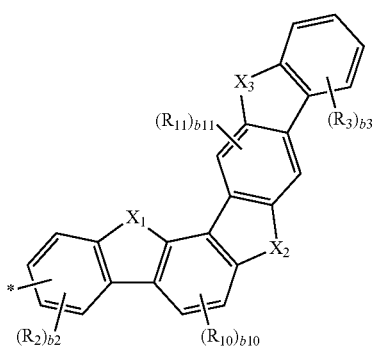
2C-11
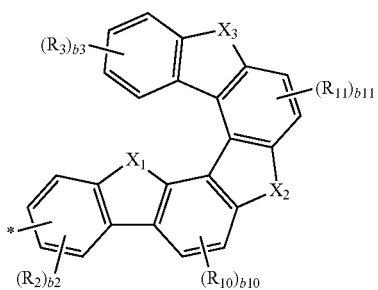
2C-12
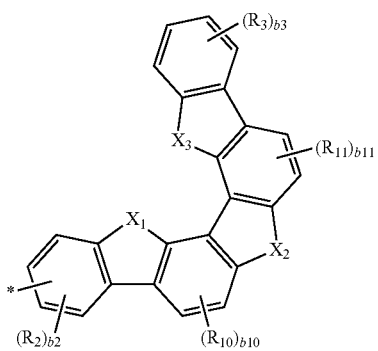
2C-13
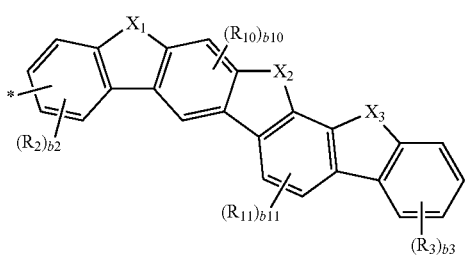
-continued
2C-14
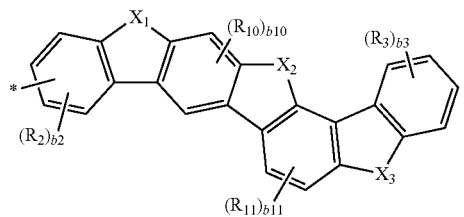
2C-15
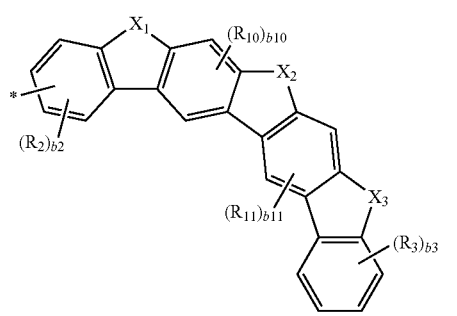
2C-16
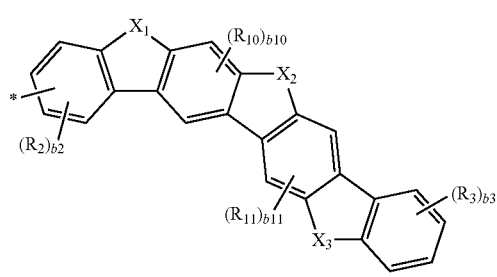
2C-17
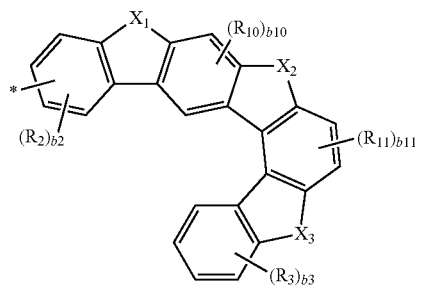
2C-18
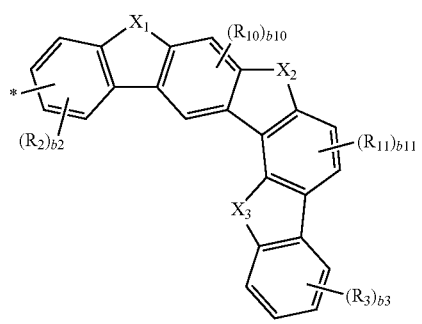

-continued
2C-19
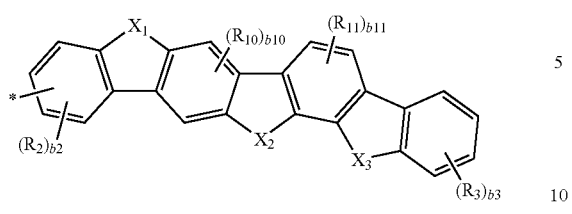
2C-20
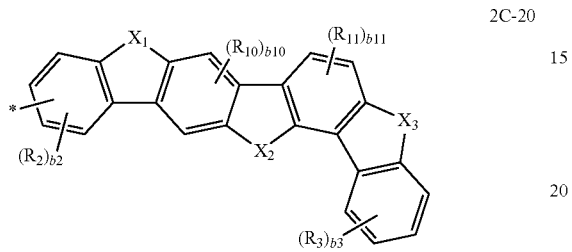
2C-21
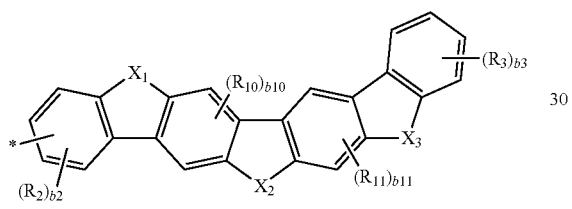
2C-22
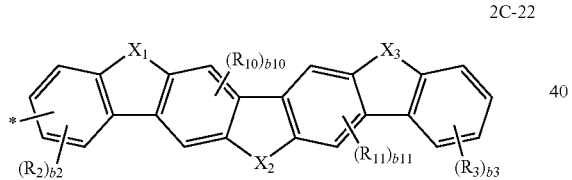
2C-23
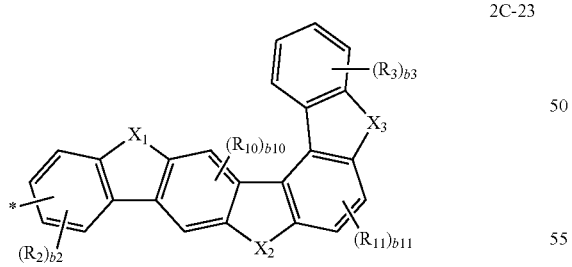
2C-24
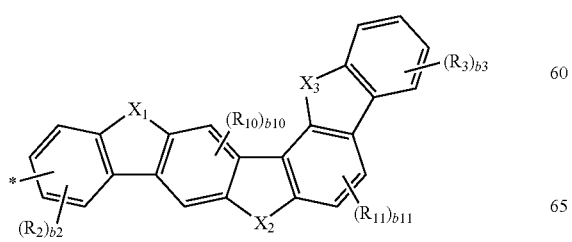
2C-25
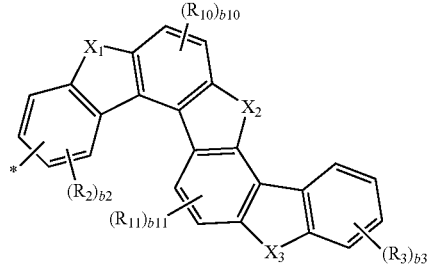
2C-26
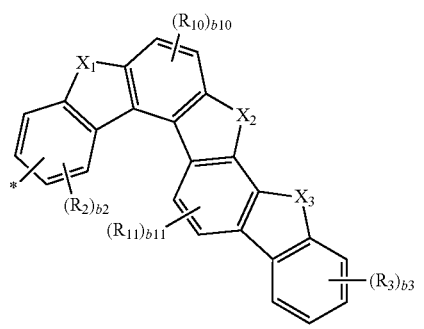
2C-27
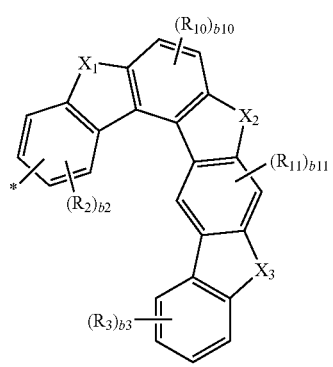
2C-28
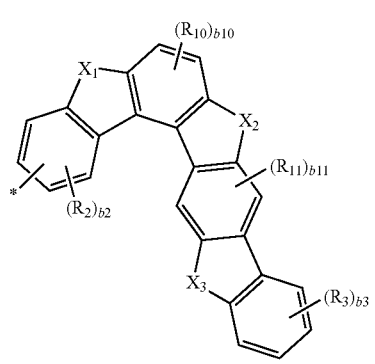
2C-29
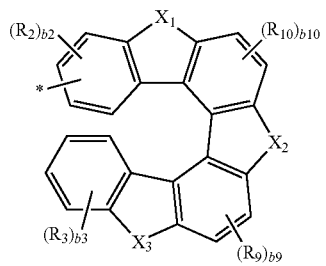

wherein, in Formulae 2A, 2B-1 to 2B-6, and 2C-1 to 2C-36,

R$_{10}$ and R$_{11}$ are each independently the same as defined in connection with R$_1$, b10 and b11 are each independently 1 or 2, and X$_1$ to X$_3$, R$_2$, R$_3$, b2, and b3 are each independently the same as described in Formulae 2A to 2C.

7. The organic light-emitting device of claim 1, wherein:

in Formulae 2A to 2C,

X$_1$ is selected from N(R$_4$), O, and S,

X$_2$ is selected from C(R$_6$)(R$_7$), N(R$_6$), O, and S, and

X$_3$ is selected from C(R$_8$)(R$_0$), N(R$_8$), 0, and S.

8. The organic light-emitting device of claim 1, wherein:

the radical scavenger comprises at least one selected from a first compound represented by Formula 10A and a second compound represented by Formula 10B:

Formula 10A

Formula 10B wherein, in Formulae 10A and 10B,

L$_2$ and L$_3$ are each independently selected from a substituted or unsubstituted C$_5$-C$_{60}$ carbocyclic group, a substituted or unsubstituted C$_1$-C$_{60}$ heterocyclic group, a substituted or unsubstituted C$_1$-C$_{60}$ alkylene group, a substituted or unsubstituted C$_2$-C$_{60}$ alkenylene group, a substituted or unsubstituted $C_3$-$C_{10}$ cycloalkylene group, *—O—*', *—N($R_{39}$)—*', *—(C=O)—O—*', and *—O—(C=O)—*', n2 and n3 are each independently an integer from 1 to 5, $Y_1$ to $Y_4$ are each independently selected from *—O—*', *—(C=O)—O—*', *—O—(C=O)—*', and *—O—(C=O)—O—*I, $R_{21}$ to $R_{28}$ and $R_{31}$ to $R_{39}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_8$-$C_{80}$ aryl group, a substituted or unsubstituted $C_8$-$C_{80}$ aryloxy group, a substituted or unsubstituted $C_8$-$C_{80}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), at least one substituent of the substituted $C_5$-$C_{60}$ carbocyclic group, the substituted $C_1$-$C_{60}$ heterocyclic group, the substituted $C_1$-$C_{60}$ alkylene group, the substituted $C_2$-$C_{60}$ alkenylene group, the substituted $C_3$-$C_{10}$ cycloalkylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{ii}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, O— indicates an oxygen radical, and

* and *$^1$ each indicate a binding site to a neighboring atom.

9. The organic light-emitting device of claim 8, wherein:

$L_2$ and $L_3$ are each independently selected from groups represented by Formulae 4-1 to 4-26, a substituted or unsubstituted $C_1$-$C_{20}$ alkylene group, *—N($R_{39}$)—*', *—(C=O)—O—*', and *—O—(C=O)—*':

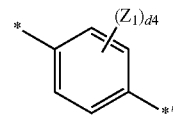

4-1

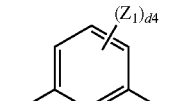

4-2

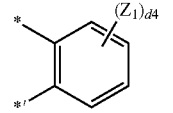

4-3

-continued
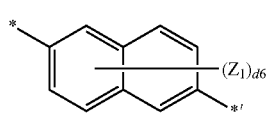
4-4
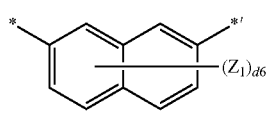
4-5
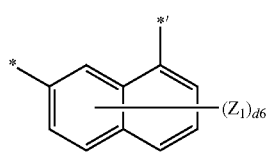
4-6
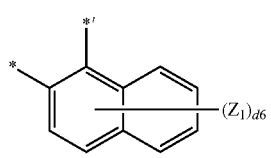
4-7
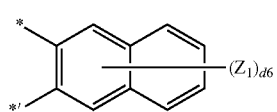
4-8
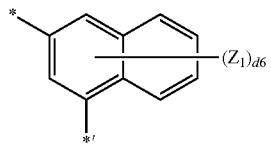
4-9
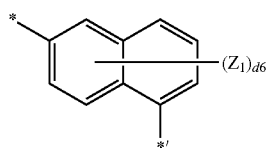
4-10
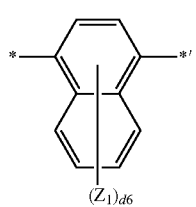
4-11
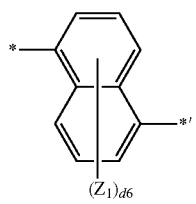
4-12
-continued
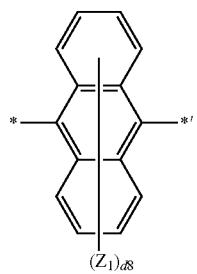
4-13
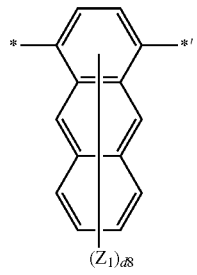
4-14
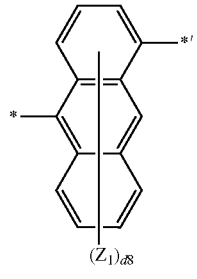
4-15
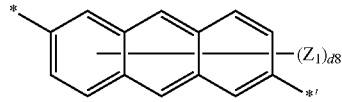
4-16
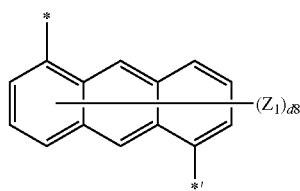
4-17
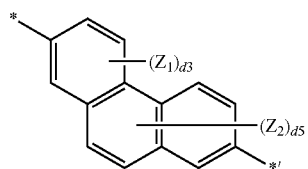
4-18
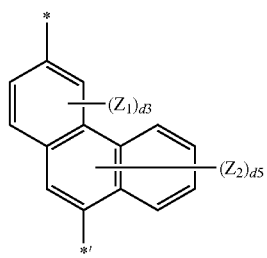
4-19

-continued

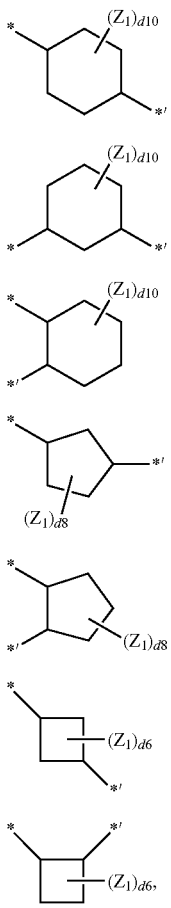

4-20

4-21

4-22

4-23

4-24

4-25

4-26 wherein, in Formulae 4-1 to 4-26, $Z_1$ and $Z_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$), d3 is an integer from 1 to 3,
d4 is an integer from 1 to 4,
d5 is an integer from 1 to 5,
d6 is an integer from 1 to 6,
d8 is an integer from 1 to 8,
d10 is an integer from 1 to 10, $Q_{31}$ to $Q_{33}$ are each independently selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *[1] each indicate a binding site to a neighboring atom.

10. The organic light-emitting device of claim 8, wherein:
$L_2$ and $L_3$ are each independently selected from:
a $C_1$-$C_{10}$ alkylene group; and
a $C_1$-$C_{10}$ alkylene group substituted with at least one selected from —F, —Cl, —Br, —I, a cyano group, a $C_1$-$C_5$ alkyl group, and a $C_1$-$C_5$ alkoxy group.

11. The organic light-emitting device of claim 8, wherein:
$Y_1$ to $Y_4$ are each independently selected from *—(C=O)—O—*[1] and *—O—(C=O)—*[1].

12. The organic light-emitting device of claim 8, wherein:
$R_{21}$ to $R_{28}$ and $R_{31}$ to $R_{39}$ are each independently selected from:
a $C_1$-$C_{10}$ alkyl group; and
a $C_1$-$C_{10}$ alkyl group substituted with at least one selected from —F, —Cl, —Br, —I, a cyano group, a $C_1$-$C_5$ alkyl group, and a $C_1$-$C_5$ alkoxy group.

13. The organic light-emitting device of claim 8, wherein:
the first compound is represented by Formula 10A-1, and the second compound is represented by Formula 10B-1:

Formula 10A-1

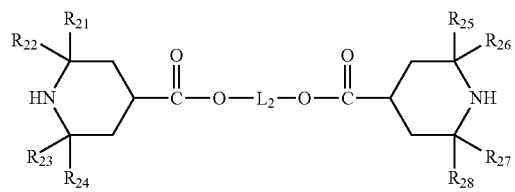

Formula 10B-1

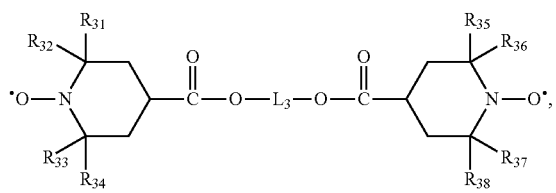

wherein, in Formulae 10A-1 and 10B-1,
$L_2$, $L_3$, $R_{21}$ to $R_{28}$, and $R_{31}$ to $R_{38}$ are each independently the same as described in Formulae 10A and 10B.

14. The organic light-emitting device of claim 8, wherein:
i) the radical scavenger comprises only the first compound;
ii) the radical scavenger comprises only the second compound; or
iii) the radical scavenger comprises the first compound and the second compound at a weight ratio of about 1:9 to about 9:1.

15. The organic light-emitting device of claim 1, wherein:
an amount of the radical scavenger is in a range of about 0.01 parts by weight to about 5 parts by weight based on 100 parts by weight of the capping layer.

16. The organic light-emitting device of claim 1, wherein:
the capping layer is in contact with the second electrode.

17. The organic light-emitting device of claim 1, wherein:
the first electrode is an anode,
the second electrode is a cathode, and
the capping layer is in contact with the cathode.

18. The organic light-emitting device of claim 1, wherein:
the first electrode is an anode,
the second electrode is a cathode,
the organic layer further comprises a hole transport region between the first electrode and the emission layer and an electron transport region between the emission layer and the second electrode,
the hole transport region comprises a hole injection layer, a hole transport layer, an emission auxiliary layer, an electron blocking layer, or any combination thereof, and
the electron transport region comprises a buffer layer, a hole blocking layer, an electron transport layer, an electron injection layer, or any combination thereof.

19. The organic light-emitting device of claim 18, wherein:
the hole transport region comprises a p-dopant, and
the p-dopant has a lowest unoccupied molecular orbital (LUMO) energy level of −3.5 eV or less.

20. A light-emitting apparatus comprising:
a transistor comprising a source electrode, a drain electrode, a gate electrode, and an active layer; and
the organic light-emitting device of claim 1,
wherein the first electrode of the organic light-emitting device is electrically coupled to one selected from the source electrode and the drain electrode.

\* \* \* \* \*